(12) United States Patent
Benvenisty et al.

(10) Patent No.: US 8,945,847 B2
(45) Date of Patent: Feb. 3, 2015

(54) METHODS AND KITS FOR ASCERTAINING BIOSAFETY OF AN AGENT

(75) Inventors: Nissim Benvenisty, Jerusalem (IL); Yoav Mayshar, Jerusalem (IL); Ofra Yanuka, Givat Zeev (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 606 days.

(21) Appl. No.: 13/114,102

(22) Filed: May 24, 2011

(65) Prior Publication Data

US 2011/0287974 A1 Nov. 24, 2011

Related U.S. Application Data

(60) Provisional application No. 61/347,619, filed on May 24, 2010.

(51) Int. Cl.
 *C12Q 1/68* (2006.01)
 *G01N 33/50* (2006.01)

(52) U.S. Cl.
 CPC ........ *G01N 33/5014* (2013.01); *G01N 33/5023* (2013.01); *G01N 33/5073* (2013.01); *C12Q 2600/142* (2013.01); *C12Q 2600/158* (2013.01)
 USPC .......... 435/6.13; 435/6.11; 435/32; 435/7.21; 435/91.3

(58) Field of Classification Search
 None
 See application file for complete search history.

(56) References Cited

U.S. PATENT DOCUMENTS

| | | | | |
|---|---|---|---|---|
| 7,829,336 | B2 * | 11/2010 | Fuchs et al. | 435/378 |
| 2004/0219563 | A1 * | 11/2004 | West et al. | 435/6 |
| 2007/0248947 | A1 | 10/2007 | Cezar | |
| 2009/0220996 | A1 | 9/2009 | Mehtal et al. | |

* cited by examiner

*Primary Examiner* — Jim Ketter

(57) ABSTRACT

A method of ascertaining the bio-safety of an agent is disclosed. The method comprises:
 (a) contacting the agent with differentiating human pluripotent stem cells;
 (b) analyzing a level of gene expression of a plurality of genes in the differentiating human pluripotent stem cells, wherein the agent is qualified as being safe if at least one of the following qualification parameters are fulfilled:
  (i) the agent causes a difference in the level of gene expression below a predetermined number of genes as compared to control differentiating human pluripotent stem cells that have not been contacted with the agent;
  (ii) the agent causes a difference in gene expression below a predetermined number of tissue-specific genes of a tissue as compared to control differentiating human pluripotent stem cells that have not been contacted with the agent; or
  (iii) the agent causes a difference in gene expression below a predetermined number of genes involved in fetal development as compared to control differentiating human pluripotent stem cells that have not been contacted with the agent.

19 Claims, 7 Drawing Sheets
(7 of 7 Drawing Sheet(s) Filed in Color)

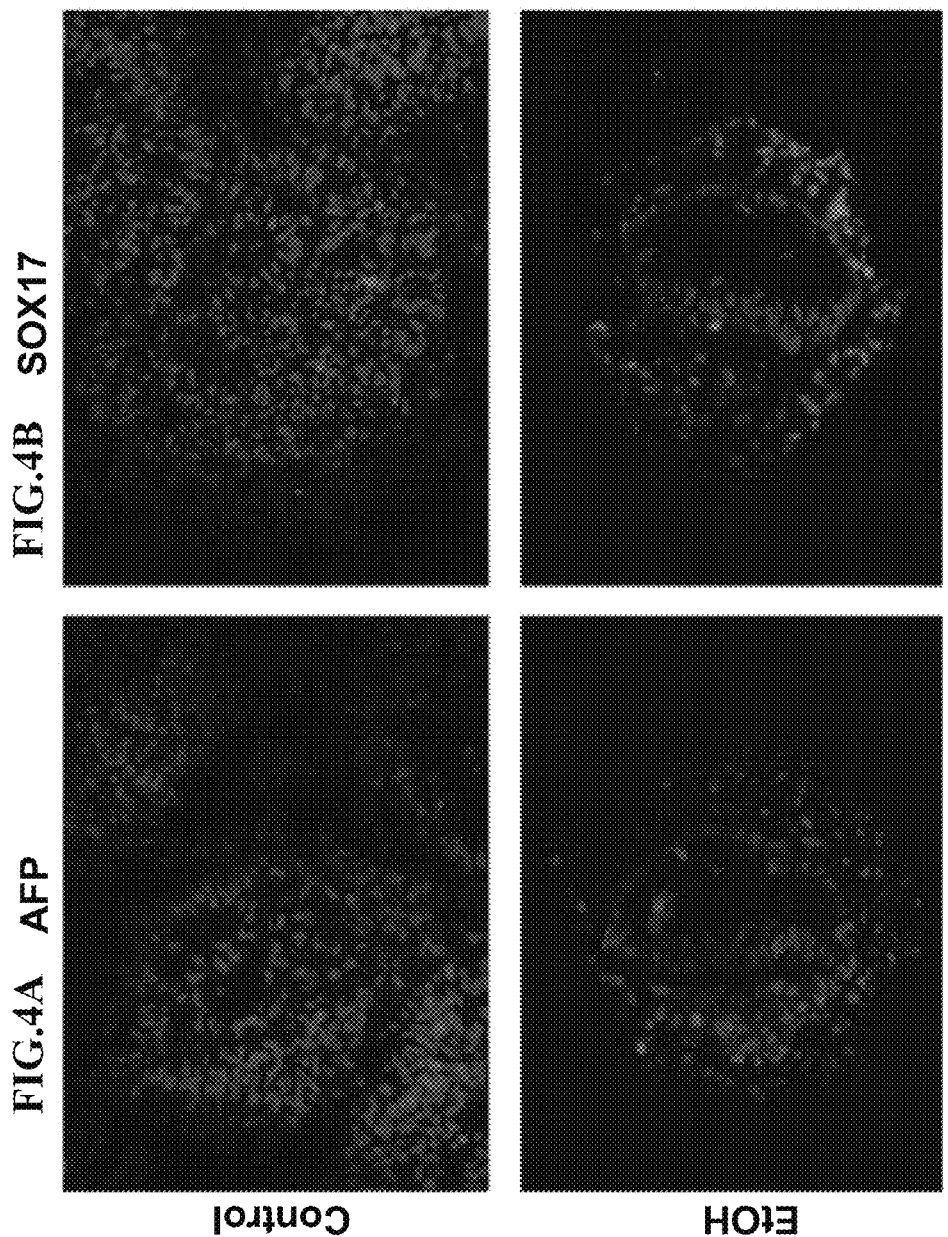

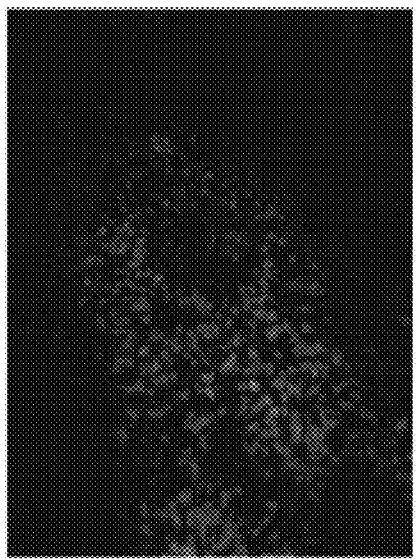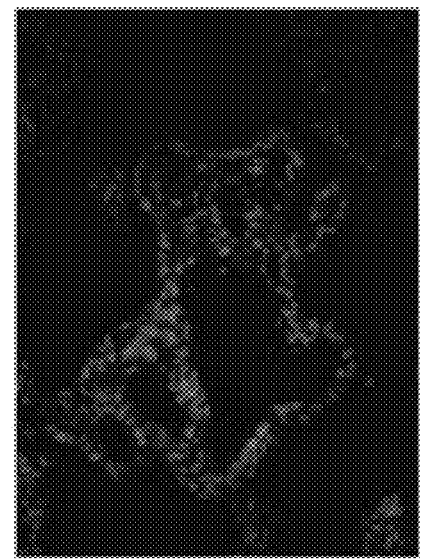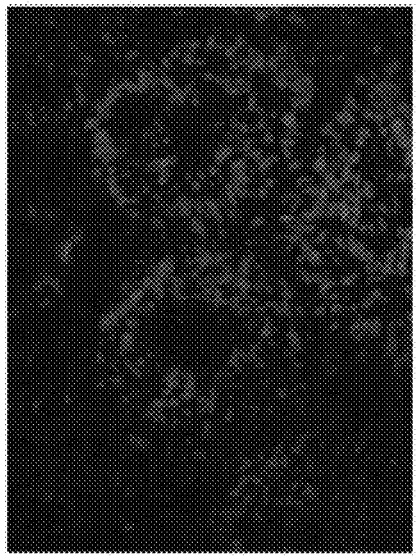

METHODS AND KITS FOR ASCERTAINING BIOSAFETY OF AN AGENT

RELATED APPLICATION/S

This application claims the benefit of priority under 35 USC 119(e) of U.S. Provisional Patent Application No. 61/347,619 filed May 24, 2010, the contents of which are incorporated herein by reference in their entirety.

FIELD AND BACKGROUND OF THE INVENTION

The present invention, in some embodiments thereof, relates to methods and kits for ascertaining biosafety of an agent.

Toxicity testing is currently one of the major hurdles for many drug discovery processes. Currently, the main methods for identifying teratogens are either through epidemiological studies in human populations or by controlled exposure of animal models. Specifically, in order to test chemicals for developmental toxicity, OECD (Organization for Economic Co-operation and Development) guidelines require approximately 20 pregnant animals for the control group and each test group, in a minimum of three doses. Following gestation pregnant animals are sacrificed and the litter examined thoroughly for abnormalities [1]. Thus, in vivo screening for teratogenic potential requires the use of a large number of laboratory animals and is very labor intensive and costly. Moreover, there are significant disparities between humans and animal models in their response to chemical substances. Notably, thalidomide is a strong human teratogen that causes many severe congenital defects but was not identified prospectively as such in the mouse [2]. On the other hand, aspirin and caffeine are teratogenic in rodents but not in humans [3,4]. For many of the most prominent teratogens known, the in vivo 'no observed adverse effect level' (NOAEL) for mouse and rat, are more than two orders of magnitude higher than the lowest reported teratogenic dose in human. Thus, inferring teratogenicity from in vivo systems (other than primates) is problematic [2]. When a "safe" margin from the animal NOAEL is often considered to be 1/100 or 1/1000 it is difficult in many cases to separate between actual teratogenic effects of compounds and non-specific effects, such as maternal toxicity. In this study we examined the potential of differentiating human embryonic stem cells (HESCs) and induced-pluripotent stem cells (HiPSCs) as an in vitro model for teratogen screening in a human developmental setting, using physiologically relevant doses.

HESCs are cells derived from blastocyst stage embryos and have the unique traits of virtually limitless propagation in culture while retaining their inherent potential to differentiate into cells from the three embryonic germ layers and extraembryonic tissue. When detached from the dish, HESCs aggregate to form embryoid bodies (EBs). They thus begin a process of spontaneous differentiation that closely mimics early human embryogenesis [5,6]. Previous studies using mouse [7-9] and human [10-12] ES cells have mainly focused on cytotoxicity assays to determine developmental toxicity. Mehta et al [11] used, in addition to the cytotoxicity test, also a test for the determination of 12 genetic markers (three for each of: ectoderm, mesoderm endoderm and un-differentiated cells) in order to evaluate the potential of the tested hESCs to differentiate.

U.S. Application No. 20090220996 discloses an embryotoxicity test used in order to replace pre clinical toxicity studies. While this application mainly discloses viability testing in differentiated, partially differentiated and non differentiated cells, it also mentions testing of expression of specific linage markers for the ectoderm, endoderm and mesoderm.

U.S. Application No. 20070248947 discloses testing the toxicity and teratogenicity of compounds on non-differentiated embryonic stem cells by following the metabolome, and testing protein changes in metabolic pathways.

SUMMARY OF THE INVENTION

According to an aspect of some embodiments of the present invention there is provided a method of ascertaining the bio-safety of an agent, the method comprising:

(a) contacting the agent with differentiating human pluripotent stem cells;

(b) analyzing a level of gene expression of a plurality of genes in the differentiating human pluripotent stem cells, wherein the agent is qualified as being safe if at least one of the following qualification parameters are fulfilled:

(i) the agent causes a difference in the level of gene expression below a predetermined number of genes as compared to control differentiating human pluripotent stem cells that have not been contacted with the agent;

(ii) the agent causes a difference in gene expression below a predetermined number of tissue-specific genes of a tissue as compared to control differentiating human pluripotent stem cells that have not been contacted with the agent; or (iii) the agent causes a difference in gene expression below a predetermined number of genes involved in fetal development as compared to control differentiating human pluripotent stem cells that have not been contacted with the agent.

According to an aspect of some embodiments of the present invention there is provided a kit for ascertaining the bio-safety of an agent comprising an array which detects expression levels of a plurality of genes, wherein a minimum of genes is about 20 and a maximum number of genes is about 1000, wherein at least 30% of the genes are tissue specific genes selected from the group consisting of those listed in Table I.

According to some embodiments of the invention, the human pluripotent stem cells comprise human embryonic stem cells.

According to some embodiments of the invention, the agent is qualified as being safe when the qualification parameter (i) is fulfilled.

According to some embodiments of the invention, the tissue is selected from the group consisting of heart, blood, liver, skeletal muscle and brain.

According to some embodiments of the invention, the agent is qualified as being safe when both the qualification parameter (i) and the qualification parameter (ii) is fulfilled.

According to some embodiments of the invention, the agent is qualified as being safe when both the qualification parameter (i) and the qualification parameter (iii) is fulfilled.

According to some embodiments of the invention, the agent is qualified as being safe when both the qualification parameter (ii) and the qualification parameter (iii) is fulfilled.

According to some embodiments of the invention, the agent is qualified as being safe when each of the qualification parameter (i), the qualification parameter (ii) and the qualification parameter (iii) is fulfilled.

According to some embodiments of the invention, the analyzing gene expression is effected by quantifying a level of a protein product of the genes in the differentiating human pluripotent stem cells.

According to some embodiments of the invention, the quantifying a level of the protein is effected by using an antibody.

According to some embodiments of the invention, the analyzing gene expression is effected by detecting the presence in the differentiating human pluripotent stem cells of transcribed polynucleotides of the genes or portions thereof.

According to some embodiments of the invention, the transcribed polynucleotides are mRNA.

According to some embodiments of the invention, the transcribed polynucleotides or portions thereof are detected via labeled probes which specifically hybridize with the transcribed polynucleotides or portions thereof.

According to some embodiments of the invention, the labeled probes are conjugated to a solid support.

According to some embodiments of the invention, the solid support is selected from the group consisting of a nylon membrane, glass slide, glass beads and a silicon chip.

According to some embodiments of the invention, the differentiating human pluripotent stem cells are comprised in embryoid bodies.

According to some embodiments of the invention, the contacting is effected following generation of the embryoid bodies.

According to some embodiments of the invention, the contacting is effected concomitant with generation of the embryoid bodies.

According to some embodiments of the invention, the plurality of genes is a random set of genes.

According to some embodiments of the invention, at least 10% of the plurality of genes comprises tissue specific genes.

According to some embodiments of the invention, at least 20% of the plurality of genes comprises tissue specific genes.

According to some embodiments of the invention, at least 40% of the plurality of genes comprises tissue specific genes.

According to some embodiments of the invention, at least 80% of the plurality of genes comprise tissue specific genes.

According to some embodiments of the invention, the plurality of genes comprises at a minimum 4000 genes.

According to some embodiments of the invention, the plurality of genes comprises at a maximum 30,000 genes.

According to some embodiments of the invention, when less than 1% of the random set of genes is differentially expressed, the agent may be qualified as safe.

According to some embodiments of the invention, when less than 5% of the tissue specific genes of a tissue of the random set of genes is differentially expressed, the agent may be qualified as safe.

According to some embodiments of the invention, when less than 4% of the differentially expressed genes of the random set of genes are fetal development associated genes, the agent may be qualified as safe.

According to some embodiments of the invention, a differential expression of a minimum of 5 tissue specific genes establishes toxicity.

According to some embodiments of the invention, a differential expression of a minimum of 20 fetal development associated genes establishes toxicity.

According to some embodiments of the invention, the method further comprises when the agent is qualified as being safe, testing the agent on an animal model to ascertain biosafety.

According to some embodiments of the invention, the method further comprises documenting results of the testing.

According to some embodiments of the invention, the agent is selected from the group consisting of a pharmaceutical agent, a food additive, an industrial chemical, a cosmetic agent and a pesticide.

According to some embodiments of the invention, wherein at least 40% of the genes are tissue specific genes.

According to some embodiments of the invention, at least an additional 30% of the genes are genes involved in fetal development.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
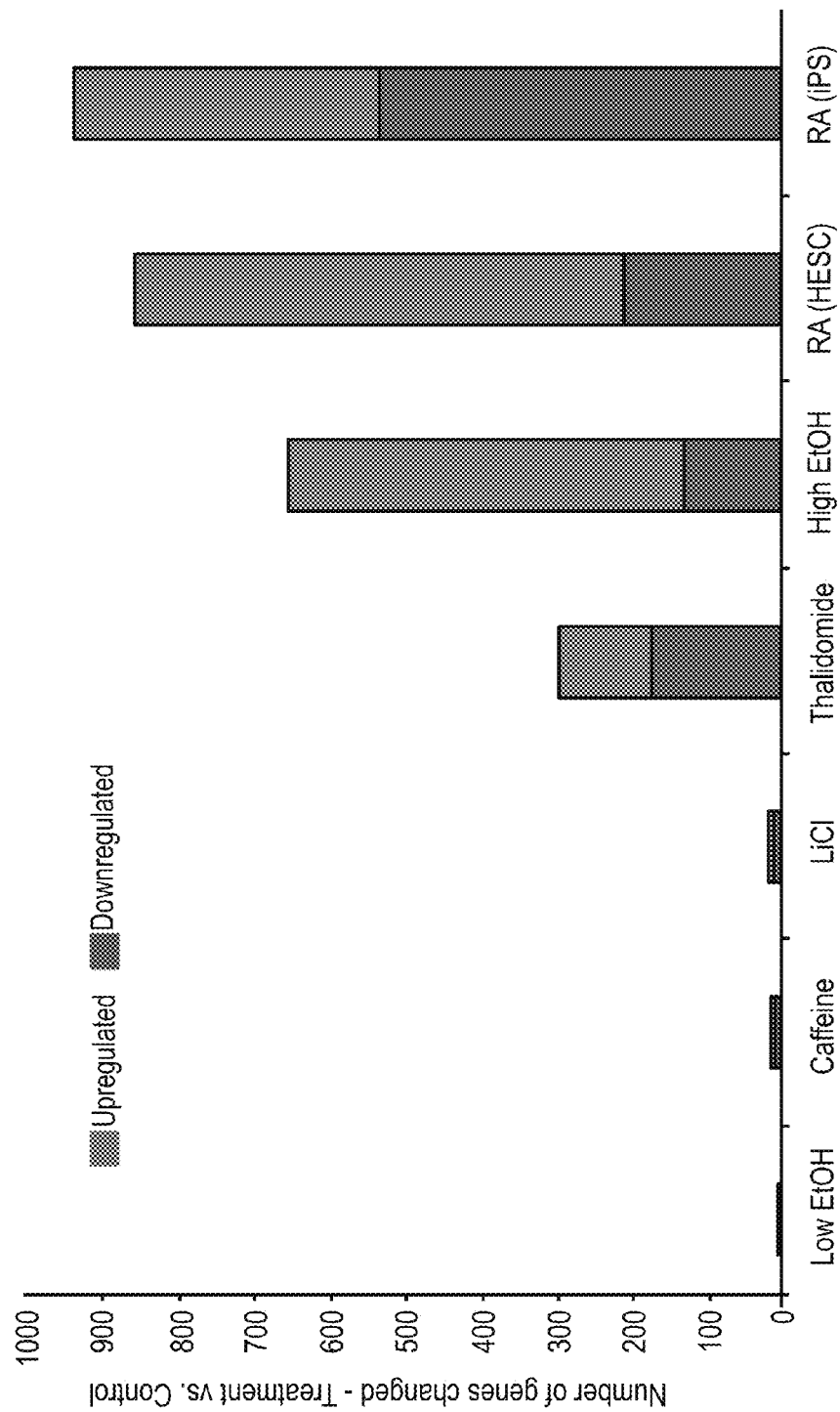
Figure 1B:
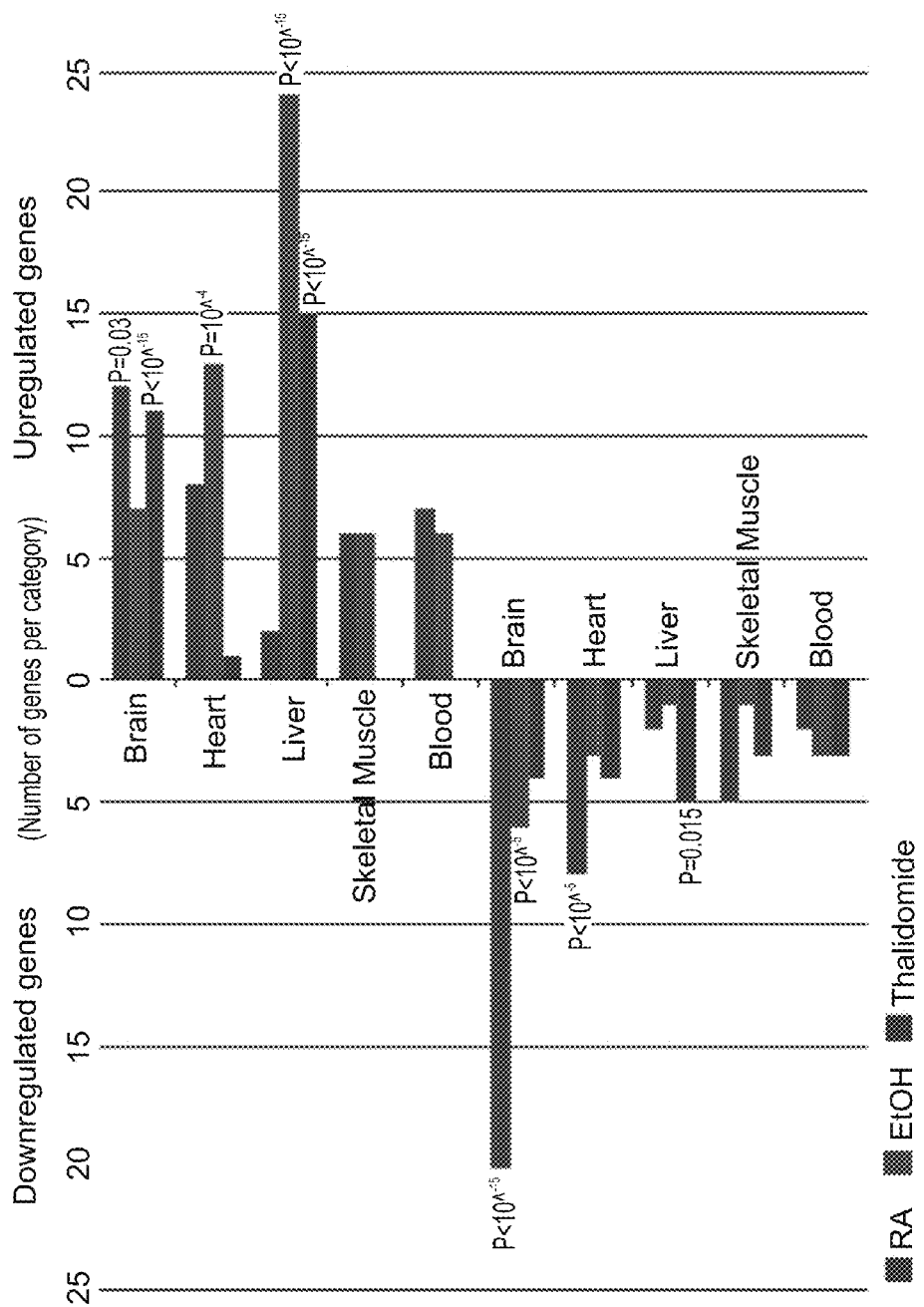

FIGS. 1A-B are graphs illustrating that ethanol, retinoic acid (RA) and thalidomide treatments lead to major global gene expression changes in human embryoid bodies. (FIG. 1A) Histogram of the total number of upregulated (blue) and downregulated (red) genes induced by each of the treatments in the study. (FIG. 1B) Tissue classification of the affected genes. Shown separately are the upregulated and downregulated genes from those treatments showing significant expression changes, classified according to tissue specific genes (as described in Materials and Methods). Significance was calculated relative to the expected number of tissue specific genes using a Chi-Square independence test and corrected for multiple testing (Bonferroni correction).

Figure 2:
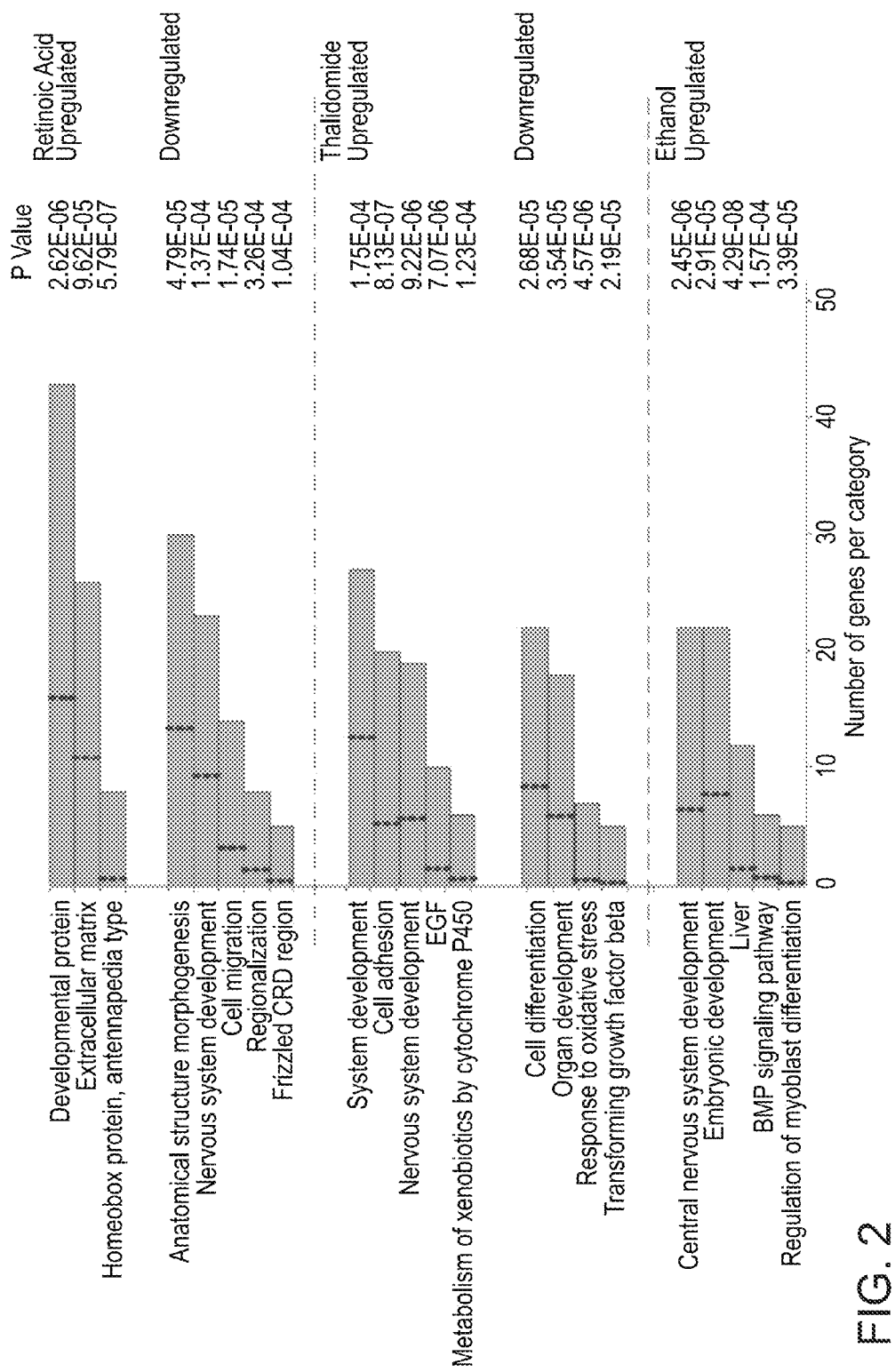

FIG. 2 is a bar graph illustrating that functional analysis of RA, thalidomide, and ethanol affected genes. Bars represent the observed number of genes per category. The internal dashed line indicates the expected number of genes, representing the frequency on the array. Shown are the top ranking non-redundant annotations for each category by p-value, with a cutoff of two-fold enrichment. Classification and significance were performed using the DAVID online functional annotation tool (http://david.abcc.ncifcrf.gov/). There were no significantly enriched functional annotations for the genes downregulated by ethanol.

Figure 3A:
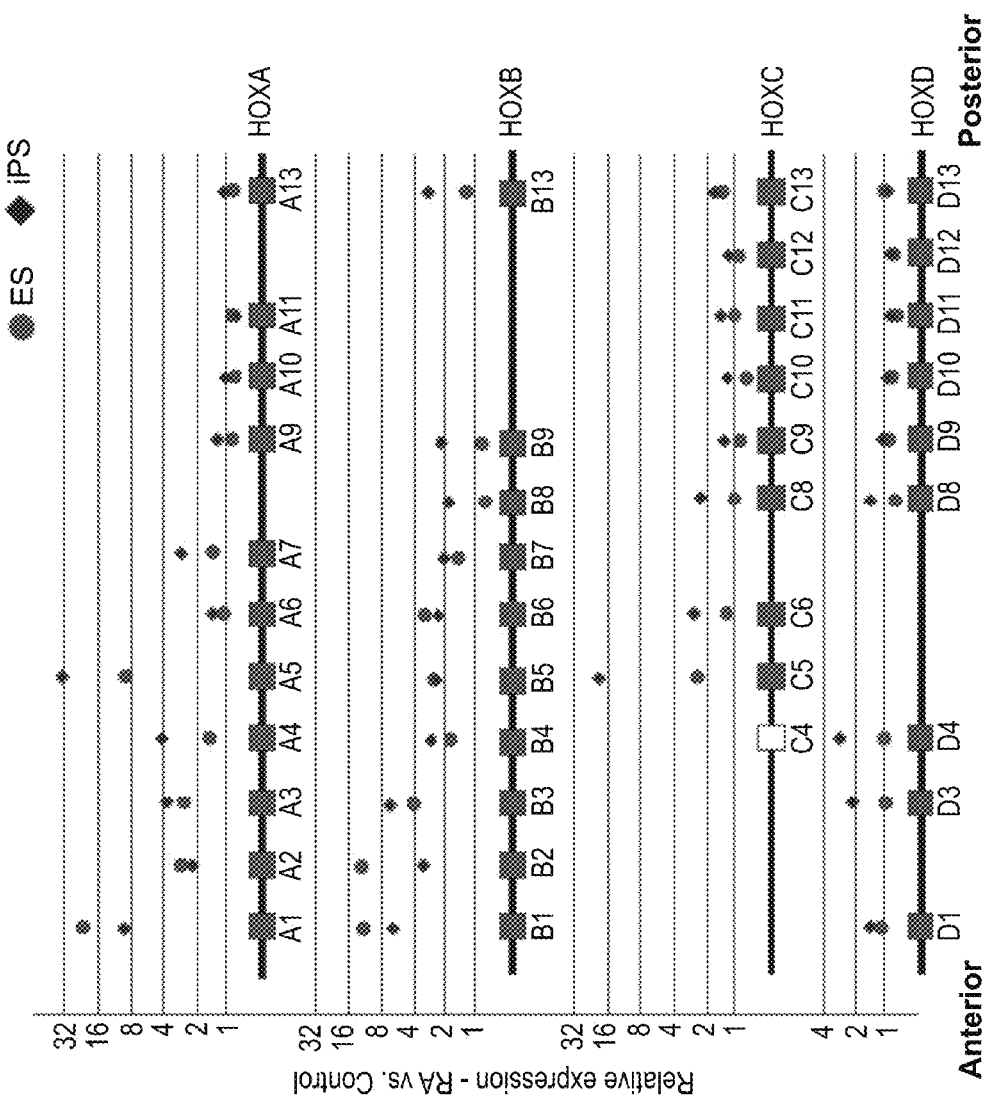
Figure 3B:
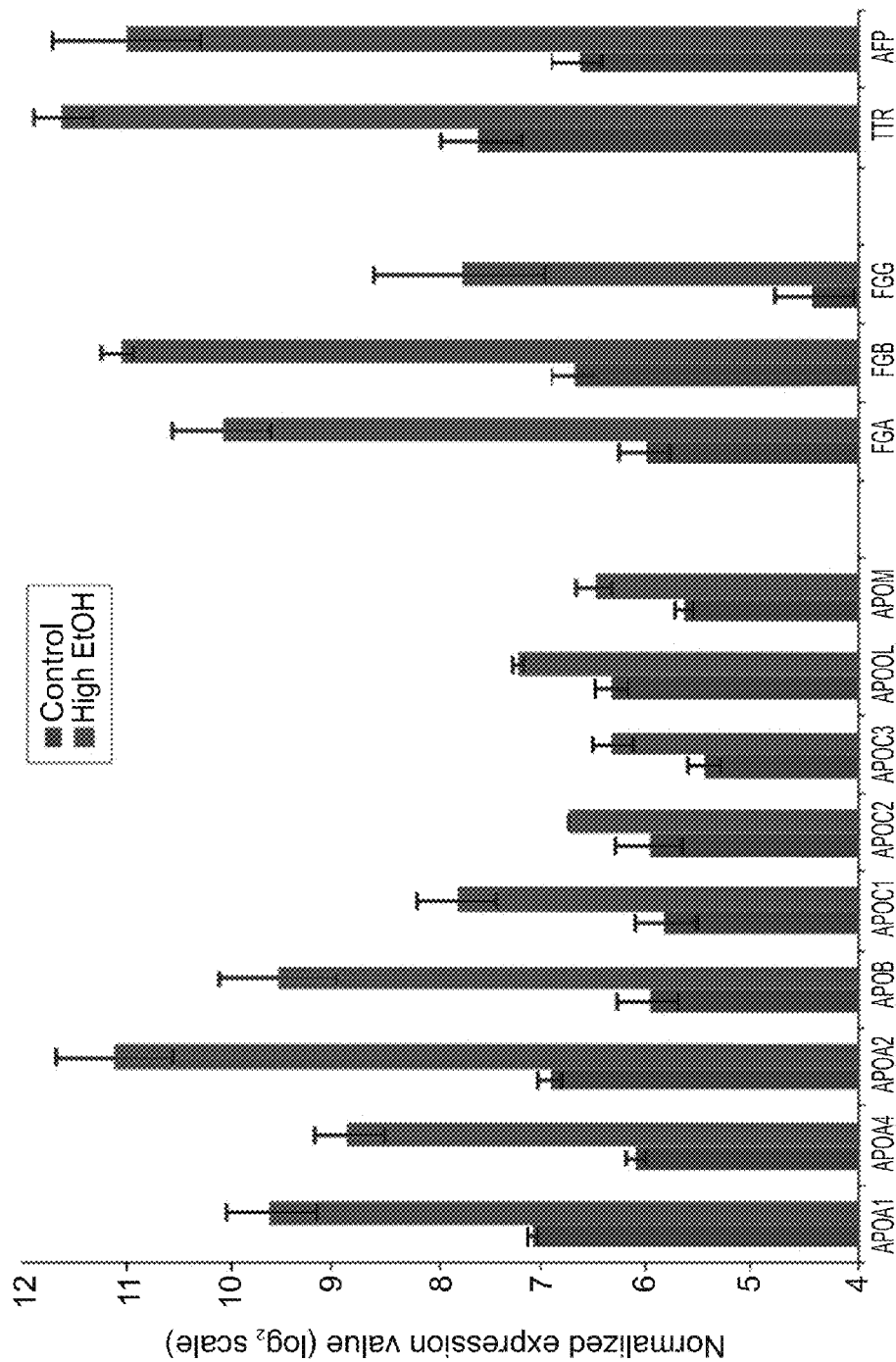

FIGS. 3A-B are graphs illustrating the effect of RA (FIG. 3A) and ethanol (FIG. 3B) on particular genes. (FIG. 3A) Anterior homeobox genes are upregulated by RA. Shown is a schematic representation of the homeobox gene clusters and fold induction by retinoic acid relative to control, in both HESC and HiPSC EBs. Red boxes indicate significance of $p<0.05$ in HESC as judged by two-tailed Student's t-test.

(FIG. 3B) Early hepatic markers are specifically upregulated following ethanol treatment. Shown are the expression levels of the alpha-fetoprotein (AFP) and transthyretin (TTR) genes as well as genes from the apolipoprotein and fibrinogen gene families that have been found to be significantly ($p<0.05$) upregulated by high ethanol (1.5% and 2%) using two-tailed Student's t-test, error bars represent standard deviation (s.d).

FIGS. 4A-H are photographs illustrating that RA and ethanol treatment affect the differentiation of EBs. (FIGS. 4A-D) Immunofluorescent labeling of the endodermal lineage shows dramatic increase in AFP and SOX17 positive cells as a result of ethanol treatment. (FIGS. 4E-H) Immunofluorescent labeling of the Hox family member HOXA1 and neuronal specific protein NCAM1 demonstrate higher differentiation into the neuronal lineage as a result of RA treatment.

DESCRIPTION OF SPECIFIC EMBODIMENTS OF THE INVENTION

The present invention, in some embodiments thereof, relates to methods and kits for ascertaining biosafety of an agent.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Exposure of the public to inadequately tested drugs or environmental agents has resulted in several notable disasters. Examples include: severe toxicity from the use of arsenic to treat syphilis, deaths from a solvent (ethylene glycol) used in sulfanilamide preparations (one of the first antibiotics); and thousands of children born with severe birth defects resulting from pregnant women using thalidomide, an anti-nausea medicine.

As such, most chemicals are now subject to stringent government requirements for safety testing before they can be marketed. This is especially true for pharmaceuticals, food additives, pesticides, and industrial chemicals. Animal testing has long been considered the gold standard for evaluating toxicology. However, animal testing takes a long time and entails the deaths of animals to acquire data. Even more, the results can't always be extrapolated to humans. Accordingly, toxicologists are now turning to high-throughput methods as alternatives to the traditional methods and as ways to prioritize chemicals for more in-depth testing.

The present inventors propose a new method for toxicology testing based on a study which examined the global developmental effects of teratogenic compounds, which can be used as an initial screen for ascertaining the biosafety of an agent.

Using a non-biased expression profiling approach the present inventors were able to identify and characterize the teratogenic effects of retinoic acid (RA), thalidomide and high levels of ethanol.

The present inventors found that they were able to qualify such known test agents as being safe or unsafe based on the number of genes which were differentially expressed in differentiating human embryonic stem cells following exposure thereto. The lower the number of genes that showed a significant change in expression following exposure to the test agent—the higher the likelihood that test agent could be qualified as being safe. Conversely, the higher the number of genes that showed a significant change in expression following exposure to the test agent—the lower the likelihood that test agent could be qualified as being safe.

The present inventors also found that changes in some genes should be considered as more significant in evaluating the safety of a test agent than changes in other genes. Thus, for example, changes in tissue-specific genes should be considered as more significant in the establishment of toxicity than changes in genes that are not tissue specific. Further, changes in genes involved in fetal development should also be considered as more significant in the establishment of toxicity.

Thus, according to one aspect of the present invention there is provided a method of ascertaining the bio-safety of an agent, the method comprising:

(a) contacting the agent with differentiating human pluripotent stem cells;

(b) analyzing a level of gene expression of a plurality of genes in the differentiating human pluripotent stem cells, wherein the agent is qualified as being safe if at least one of the following qualification parameters are fulfilled:

(i) the agent causes a difference in the level of gene expression below a predetermined number of genes as compared to control differentiating human pluripotent stem cells that have not been contacted with the agent;

(ii) the agent causes a difference in gene expression below a predetermined number of tissue-specific genes of a tissue as compared to control differentiating human pluripotent stem cells that have not been contacted with the agent; or (iii) the agent causes a difference in gene expression below a predetermined number of genes involved in fetal development as compared to control differentiating human pluripotent stem cells that have not been contacted with the agent.

As used herein, the phrase "pluripotent stem cells" refers to cells which are capable of differentiating into the three embryonic germ cell layers, i.e., endoderm, ectoderm and mesoderm; and which are capable of remaining in an undifferentiated state for extended periods of time in culture until induced to differentiate into other cell types having a particular, specialized function (e.g., fully differentiated cells).

The phrase "embryonic stem cells" refers to embryonic cells which are capable of differentiating into cells of all three embryonic germ layers (i.e., endoderm, ectoderm and mesoderm), or remaining in an undifferentiated state.

The embryonic stem cells of some embodiments of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Feral. Steril. 69: 84, 1998].

It will be appreciated that commercially available stem cells can also be used with this aspect of some embodiments of the invention. Human ES cells can be purchased from the NIH human embryonic stem cells registry (http://escr.nih.gov). Non-limiting examples of commercially available embryonic stem cell lines are BG01, BG02, BG03, BG04, CY12, CY30, CY92, CY10, TE03 and TE32.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation which re-program the cell to acquire embryonic stem cells characteristics. According to some embodiments of the invention, the induced pluripotent stem cells are formed by inducing the expression of Oct-4, Sox2, Kfl4 and c-Myc in a somatic stem cell.

It will be appreciated that the pluripotent stem cells of this aspect of the present invention have begun their initial stages of differentiation but are not terminally differentiated. Typically, the cells are not differentiated for more than 30 days. Any method for differentiation of pluripotent stem cells is appropriate for this aspect of the present invention so long as the cells do not lose their potential to differentiate into derivatives of all three germ layers. Thus, the cells may be differentiated in suspension (e.g. generation of embryoid bodies) or via adherent culture (e.g. as monolayers).

Thus, according to one embodiment, the cells are differentiated into embryoid bodies. As used herein the phrase "embryoid bodies" (EBs) refers to three dimensional multicellular aggregates of differentiated and undifferentiated cell derivatives of all three embryonic germ layers.

Embryoid bodies are formed upon the removal of ES cells (or iPS cells) from feeder layers or feeder cells-free culture systems. ES cells removal can be effected using type IV Collagenase treatment for a limited time. Cell aggregation is imposed by hanging drop, plating upon non-tissue culture treated plates or spinner flasks; either method prevents cells from adhering to a surface to form the typical colony growth. Upon aggregation, differentiation is initiated and the cells begin to a limited extent to recapitulate embryonic development.

Exemplary agents that may be tested for safety include, but are not limited to pharmaceutical agents, food products (e.g. food additives), industrial chemicals, cosmetic agents and pesticides. The agents may be known agents or may be possible candidate agents undergoing safety screening prior to marketing. The agent may comprise one agent or a combination of more than one agent. It will be appreciated that the agent may also be a physical condition, such as a radiation exposure (such as, gamma radiation, UV radiation, Xray-radiation).

Contacting the differentiating cells with the agent can be performed by any in vitro conditions including for example, adding or incubating the agent to the differentiating cells such that the agent is in direct contact with the cells. The conditions used for incubating the cells are selected for a time period/concentration of cells/concentration of agent/ratio between cells and agent and the like which enable the agent to induce changes in gene expression.

It will be appreciated that the agent may be contacted during the initial stages of differentiation (e.g. concomitant with the generation of embryoid bodies) or following the initial stages of differentiation (e.g. following the generation of embryoid bodies). The exact amount of contact time will depend on amongst other variables, the exact stage of differentiation the embryonic stem cells are at.

Thus, for example embryoid bodies may be contacted with the agent for at least 3 days, more preferably for at least 5 days and even more preferably for at least 7 days.

According to one embodiment, the concentration of the test agent should be a concentration that mimics the concentration commonly present in the serum of the mother and therefore, the concentration to which the fetus may be exposed to in the womb.

For example, prescribed levels of retinoic acid are 0.5-1.5 mg/kg/day while the present study examined the effect of 0.3 mg/kg.

As mentioned, in order to ascertain safety of an agent, the gene expression of the differentiating cells is analyzed in the presence and absence of the agent.

Briefly, measurement of gene expression may be effected on the RNA or protein level by any method known in the art (see, e.g., Sambrook, J., Fritsh, E. F., and Maniatis, T. Molecular Cloning: A Laboratory Manual. 2nd, ed, Cold Spring Harbor Laboratory, Cold Spring Harbor Laboratory Press, Cold Spring Harbor, N.Y., 1989; and Current Protocols in Molecular Biology, eds. Ausubel et al. John Wiley & Sons: 1992).

Typical methodologies for RNA detection include RNA extraction from the differentiating cells (using e.g., a TRI-ZOL solution, Gibco BRL, USA), followed by one of the following methods: Northern Blot analysis, RT-PCR analysis, RNA in situ hybridization stain, in situ RT-PCR stain, DNA microarrays/DNA chips and oligonucleotide microarray.

Methods of detecting expression of proteins include protein extraction from the differentiating cells followed by Western blot analysis, radio-immunoassay (RIA), Fluorescence activated cell sorting (FACS) and immunohistochemical analysis.

Detection of RNA or proteins is typically effected using a labeled probe, in the case of RNA, a labeled polynucleotide sequence which is capable of hybridizing to the RNA and in the case of a protein, a labeled antibody or antibody fragment capable of recognizing the protein. The label group can be a radioisotope ($^{125}$I, $^{131}$I, $^{35}$S or $^3$H), a fluorescent compound (umbelliferone, fluorescein, fluorescein isothiocyanate, rhodamine, dichlorotriazinylamine fluorescein, dansyl chloride or phycoerythrin) a bioluminescent compound (e.g. luciferase, luciferin, and aequorin), a prosthetic group complex (e.g. biotin/strepavidin and avidin/biotin), an enzyme (e.g. horseradish peroxidase, alkaline phosphatase, -galactosidase, or acetylcholinesterase), or an enzyme co-factor.

Detection of specific polypeptide and nucleic acid molecules may also be assessed by gel electrophoresis, column chromatography, direct sequencing (in the case of nucleic acid molecules) among many other techniques well known to those skilled in the art.

In cases where the method involves analyzing expression of more than about 20 genes, the detection method of the present invention preferably employs marker probes which are conjugated to a solid support (e.g., a glass wafer, a nylon membrane, a glass slide, glass beads or a silicon chip). For detection of RNA oligonucleotides probes may be used. Typically, each oligonucleotide probe is of approximately 20-25 nucleic acids in length. Hybridization can take place using either labeled oligonucleotide probes (e.g., 5'-biotinylated probes) or labeled fragments of complementary DNA (cDNA) or RNA (cRNA). Briefly, double stranded cDNA is prepared from the RNA using reverse transcriptase (RT) (e.g., Superscript II RT), DNA ligase and DNA polymerase I, all according to manufacturer's instructions (Invitrogen Life Technologies, Frederick, Md., USA). To prepare labeled cRNA, the double stranded cDNA is subjected to an in vitro transcription reaction in the presence of biotinylated nucleotides using e.g., the BioArray High Yield RNA Transcript Labeling Kit (Enzo, Diagnostics, Affymetix Santa Clara Calif.). For efficient hybridization the labeled cRNA can be fragmented by incubating the RNA in 40 mM Tris Acetate (pH 8.1), 100 mM potassium acetate and 30 mM magnesium acetate for 35 minutes at 94° C. Following hybridization, the array is washed and the hybridization signal is scanned using a confocal laser fluorescence scanner which measures fluorescence intensity emitted by the labeled cRNA bound to the probe arrays.

It will be appreciated that in order to verify detection of a specific gene, negative controls are preferably used. For example, in the Affymetrix microarray (Affymetrix®, Santa Clara, Calif.) each gene on the array is represented by a series of different oligonucleotide probes, of which, each probe pair consists of a perfect match oligonucleotide and a mismatch oligonucleotide. While the perfect match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent scanner, and the Microarray Suite software subtracts the non-specific signal resulting from the mismatch probe from the signal resulting from the perfect match probe.

As a further control, more than one probe may be used to detect a particular gene. Thus, for example, one gene may be represented by at least 2 or 3 probes which are capable of hybridizing to different positions along the gene.

It will also be apparent to one skilled in the art that the probes of the array need not bind with the entire gene. A probe designed to bind a portion of the gene of sufficient length for detection purposes (e.g., for hybridization), for example, a portion of the marker which is 7, 10, 15, 20, 25, 30, 35, 40, 45, 50, 55, 60, 65, 70, 75, 100 or more nucleotides or amino acids in length may be sufficient for detection purposes and specificity.

Polynucleotide probes can be synthesized using any known synthesis method. Preferably, synthesis is effected using on-chip lithography methodology in a manner similar to that utilized for the synthesis of Affymetrix chips (worldwidewebdotaffymetrixdotcom).

Antibody probes useful for detecting polypeptide markers can be generated using various well known techniques. For example, monoclonal antibodies which can be used per se or as a basis for antibody fragments (scFv, Fab etc) can be synthesized using isolated Hybridomas. In such an approach, a protein corresponding to a marker of the invention is isolated (e.g., by purification from a cell in which it is expressed or by transcription and translation of a nucleic acid encoding the protein in vivo or in vitro using known methods). A vertebrate, preferably a mammal such as a mouse, rat, rabbit, or sheep, is immunized using the isolated protein or protein fragment. The vertebrate may optionally (and preferably) be immunized at least one additional time with the isolated protein or protein fragment, so that the vertebrate exhibits a robust immune response to the protein or protein fragment. Splenocytes are isolated from the immunized vertebrate and fused with an immortalized cell line to form hybridomas, using any of a variety of methods well known in the art. Hybridomas formed in this manner are then screened using standard methods to identify one or more hybridomas which produce an antibody which specifically binds with the protein or protein fragment.

By analyzing the global gene expression profile of differentiating embryonic stem cells, the present inventors have found that the number of genes that are differentially expressed is indicative of the safety of an agent.

A substantial difference in gene expression is preferably of a magnitude that is statistically significant. In particularly preferred embodiments, the expression of a gene is increased or decreased relative to control samples by at least 2-, 3-, 4-, 5-, 6-, 7-, 8-, 9-, or 10-fold or more. Similarly, one skilled in the art will be well aware of the fact that a preferred detection methodology is one in which the resulting detection values are above the minimum detection limit of the methodology utilized.

The term "gene expression profile or "global gene expression profile" refers to the unbiased, determination of the expression of genes. The proportion of those genes associated with a particular function expressed as a percentage of the total genes analyzed in a global gene expression profile should mirror/reflect the percentage of the genes associated with that function in the overall genome. Thus, no particular group of genes involved in a particular function or expressed in a particular tissue is overly represented or analyzed during global gene expression profiling. Thus, in the case of the human genome for example, if about 3% of all genes in the human genome are used to define tissue specificity, then only 3% of all genes being analyzed should be ones defined as tissue specific. If only 10% of all genes in the human genome are involved in fetal development, then only 10% of all genes being analyzed should be ones involved in fetal development.

The minimum number of random genes that the present inventors conceive is sufficient to ascertain safety by performing global gene expression analysis is typically greater than about 2000. According to another embodiment, the number of random genes that the present inventors conceive is sufficient to ascertain safety by performing global gene expression analysis is typically greater than about 4000. According to another embodiment, the number of random genes that the present inventors conceive is sufficient to ascertain safety by performing global gene expression analysis is typically greater than about 5000. Thus, the present inventors conceive that the number of random genes that can be analyzed to ascertain safety by performing global gene expression analysis is about 4000, about 5000, about 6000, about 7000, about 8000, about 10,000, about 12,000, about 15,000, about 18,000, about 20,000, about 22,000, about 24,000, about 26,000, about 28,000, about 30,000, about 32,000 or about 34,000.

According to this embodiment, if the expression of only a relatively few number of genes is altered compared to the control cells, the agent may be regarded as safe. If, however, many genes are altered compared to the control cells, the agent may be regarded as being toxic. Thus, for an unbiased, random expression array which is capable of detecting expression of about 4000-30,000 genes, an agent may be qualified as being safe if less than about 1% of the genes are differentially expressed. According to another embodiment, an agent may be qualified as being safe if less than about 0.9% genes are differentially expressed. According to another embodiment, an agent may be qualified as being safe if less than about 0.8% genes are differentially expressed. According to another embodiment, an agent may be qualified as being safe if less than about 0.7% of the genes are differentially expressed. According to another embodiment, an agent may be qualified as being safe if less than about 0.6% of the genes are differentially expressed. According to another embodiment, an agent may be qualified as being safe if less than about 0.5% genes are differentially expressed. According to another embodiment, an agent may be qualified as being safe if less than about 0.4% of the genes are differentially expressed.

Thus for example in the case of a non-biased chip being able to detect about 30,000 genes, an agent may be qualified as being safe if less than about 50 genes are differentially expressed. According to another embodiment, an agent may be qualified as being safe if less than about 100 genes are differentially expressed. According to another embodiment, an agent may be qualified as being safe if less than about 150 genes are differentially expressed. According to another embodiment, an agent may be qualified as being safe if less than about 200 genes are differentially expressed. According to another embodiment, an agent may be qualified as being safe if less than about 250 genes are differentially expressed. According to another embodiment, an agent may be qualified as being safe if less than about 300 genes are differentially expressed. According to another embodiment, an agent may be qualified as being safe if less than about 350 genes are differentially expressed.

It will be appreciated that as well as the number of genes that are affected various additional factors also influence the ability to qualify the safety of an agent. Thus, for example if an agent causes a higher change in the expression levels of a certain group of genes (for example a 10 fold increase or decrease) then it will be considered less safe than a compound causing a lower change in the expression level (e.g. only a two fold change) in that same group of genes.

In addition, the function of the changed gene also bears relevance on the qualification of the safety of a particular agent. In particular, the present inventors have found that if the changed gene is involved in tissue specificity, this carries a heavier weight than if the changed gene was not involved in tissue specificity. Moreover, an overabundance of genes involved in tissue specificity of a certain tissue carries a greater weight than lower abundance of tissue specific genes that could arise by chance of a random selection of genes from the total non-biased chip. For example, if for a certain agent, 12 tissue specific genes of one particular tissue were found to be differentially expressed, while only 4 are expected to be differentially expressed by chance, this would be more indicative of toxicity than 12 tissue specific genes of three different tissues.

As used herein, the phrase "tissue specific gene" refers to a gene that is preferentially expressed in any of the following tissues—brain, heart, liver, skeletal muscle and blood.

Examples of tissue specific genes are set forth in Table 1, herein below.

TABLE 1

| Probe Set ID | Gene Symbol | SEQ ID NO: |
|---|---|---|
| 7959102 | HSPB8 | 333 |
| 7994131 | PRKCB | 1617 |
| 7987315 | ACTC1 | 928 |
| 7971461 | LCP1 | 1599 |
| 8037079 | ATP1A3 | 478 |
| 8029536 | APOC1 | 516 |

TABLE 1-continued

| Probe Set ID | Gene Symbol | SEQ ID NO: |
|---|---|---|
| 7945680 | H19 | 583 |
| 8157193 | ZNF483 | 1511 |
| 7962212 | PKP2 | 1151 |
| 8024728 | ITGB1BP3 | 1182 |
| 8077192 | APOA4 | 696 |
| 7951859 | APOA4 | 696 |
| 8100758 | — | 2500 |
| 7906919 | RGS4 | 1324 |
| 7929373 | LGI1 | 1397 |
| 8116780 | DSP | 590 |
| 8121784 | FABP7 | 320 |
| 8053654 | FABP1 | 2299 |
| 8103311 | FGA | 686 |
| 8100768 | UGT2B11 | 23 |
| 7913216 | PLA2G2A | 1923 |
| 7982084 | SNRPN//SNORD115-11 | 1049 |
| 8140686 | SEMA3D | 392 |
| 8057677 | SLC40A1 | 1426 |
| 8027837 | CD22 | 2130 |
| 8126784 | PLA2G7 | 1478 |
| 8023043 | PSTPIP2 | 1328 |
| 8026971 | IFI30 | 243 |
| 7981068 | SERPINA1 | 1483 |
| 8171359 | GPM6B | 488 |
| 8154233 | CD274 | 2074 |
| 8051762 | SLC8A1 | 953 |
| 7969574 | — | 2433 |
| 8115651 | GABRB2 | 1037 |
| 8131583 | BZW2 | 1899 |
| 8104022 | PDLIM3 | 2180 |
| 8170119 | FHL1 | 1898 |
| 7962455 | NELL2 | 1840 |
| 8112615 | ENC1 | 1501 |
| 7970954 | DCLK1 | 2192 |
| 8135774 | PTPRZ1 | 807 |
| 8004545 | ATP1B2 | 482 |
| 7954293 | PDE3A | 683 |
| 8114900 | PPP2R2B | 269 |
| 7952490 | FEZ1 | 2190 |

TABLE 1-continued

| Probe Set ID | Gene Symbol | SEQ ID NO: |
|---|---|---|
| 7989670 | RBPMS2 | 317 |
| 7982535 | C15orf41 | 1539 |
| 8144786 | SLC7A2 | 1967 |
| 7924910 | ACTA1 | 451 |
| 8045637 | KIF5C | 30 |
| 8147244 | NECAB1 | 1802 |
| 8174201 | BEX1 | 682 |
| 8087530 | CAMKV | 754 |
| 7951865 | APOA1 | 25 |
| 8077185 | APOA1 | 25 |
| 8147123 | CA3 | 1674 |
| 8086689 | MYL3 | 952 |
| 7946167 | HPX | 1893 |
| 8001531 | MT1G | 62 |
| 8111255 | CDH10 | 2136 |
| 7979658 | GPX2 | 274 |
| 8071420 | SERPIND1 | 710 |
| 7921834 | APOA2 | 19 |
| 8047926 | MAP2 | 788 |
| 8084766 | TP63 | 1368 |
| 8023528 | ALPK2 | 1146 |
| 8050619 | APOB | 872 |
| 8084648 | AHSG | 1242 |
| 8020795 | TTR | 1794 |
| 8096580 | MTTP | 1196 |
| 7934979 | ANKRD1 | 339 |
| 8128565 | POPDC3 | 1743 |
| 7982046 | SNRPN//SNORD115-20 | 1057 |
| 8128553 | BYES | 2228 |
| 8103326 | EGG | 687 |
| 8097910 | FGB | 2113 |
| 7957140 | LGR5 | 194 |
| 8087925 | TNNC1 | 1645 |
| 8082797 | TF | 1957 |
| 7982018 | SNRPN//SNORD115-6 | 1058 |
| 7982030 | SNRPN//SNORD115-12 | 1054 |
| 7982090 | SNRPN//SNORD115-42 | 1044 |
| 7982092 | SNRPN//SNORD115-11 | 1049 |
| 7982058 | SNRPN//SNORD115-26 | 1050 |
| 8169061 | PLP1 | 386 |
| 7935116 | RBP4 | 550 |
| 7919055 | HMGCS2 | 1983 |
| 8072678 | HMOX1 | 2135 |
| 8101429 | PLAC8 | 1590 |
| 8055465 | CXCR4 | 580 |
| 8046695 | ITGA4 | 663 |
| 7969330 | PCDH17 | 934 |
| 7914950 | CSF3R | 2186 |
| 8180022 | FILA-DQB1 | 2 |
| 8112478 | NAIP | 1012 |
| 7952601 | ETS1 | 1783 |
| 8007620 | GRN | 601 |
| 8001800 | CDH11 | 107 |
| 8138805 | CPVL | 751 |
| 8091385 | CP | 1498 |
| 8137264 | TMEM176A | 272 |
| 8102328 | CFI | 1348 |
| 8149551 | PSD3 | 989 |
| 8022674 | CDH2 | 1744 |
| 7991335 | ANPEP | 1261 |
| 8140752 | ABCB4 | 912 |
| 8056890 | CHN1 | 2318 |
| 8104035 | SORBS2 | 1587 |
| 7981990 | SNRPN//SNORD116-21 | 1084 |
| 8142687 | GPR37 | 258 |
| 7953532 | ENO2 | 110 |
| 7954899 | CNTN1 | 231 |
| 8101587 | MAPK10 | 1960 |
| 8053315 | LRRTM4 | 1233 |
| 8067985 | NCAM2 | 2249 |
| 8156134 | NTRK2 | 650 |
| 8073548 | SEPT3 | 1245 |
| 7919645 | SV2A | 1757 |
| 7932420 | PTPLA | 743 |
| 8060134 | KIF1A | 382 |
| 7941662 | ACTN3 | 24 |
| 8022986 | SYT4 | 1734 |

TABLE 1-continued

| Probe Set ID | Gene Symbol | SEQ ID NO: |
|---|---|---|
| 8081810 | GAP43 | 1551 |
| 8007921 | MYL4 | 507 |
| 7902043 | DNAJC6 | 552 |
| 8147030 | STMN2 | 2221 |
| 8077204 | APOC3 | 26 |
| 7955502 | SCN8A | 900 |
| 8047300 | AOX1 | 697 |
| 7932796 | SVIL | 1180 |
| 7944035 | APOC3 | 26 |
| 8013606 | VTN | 789 |
| 8025918 | CNN1 | 573 |
| 8149835 | NEFL | 1640 |
| 7972231 | SLITRK1 | 356 |
| 7956522 | KIF5A | 71 |
| 8138997 | TBX20 | 1990 |
| 8098041 | TMEM144 | 1595 |
| 8097991 | TDO2 | 1549 |
| 7922162 | SLC19A2 | 1388 |
| 7956488 | KIF5A | 422 |
| 7960919 | MFAP5 | 444 |
| 8163839 | C5 | 334 |
| 8081219 | ST3GAL6 | 257 |
| 8088491 | CADPS | 1637 |
| 8114964 | SPINK1 | 1593 |
| 7982094 | SNRPN//SNORD115-44 | 1053 |
| 8095390 | UGT2B10 | 1804 |
| 7943562 | ELMOD1 | 1548 |
| 7918768 | DENND2C | 1023 |
| 8092726 | CLDN1 | 2121 |
| 7926061 | ITIH2 | 685 |
| 7949124 | PYGM | 1323 |
| 8040430 | VSNL1 | 645 |
| 8146669 | TRIM55 | 315 |
| 7932453 | NEBL | 1634 |
| 8093278 | HGD | 2104 |
| 8906501 | ATP1A2 | 1681 |
| 8017766 | APOH | 1194 |
| 8079931 | SLC38A3 | 1253 |
| 8095395 | UGT2B7 | 1512 |
| 8123246 | SLC22A3 | 196 |
| 7982038 | SNORD115-1 | 1052 |
| 8100784 | UGT2B4 | 1170 |
| 8095628 | ALB | 1754 |
| 7951479 | SLN | 1039 |
| 7924987 | AGT | 1460 |
| 7921332 | CDSL | 1430 |
| 7957962 | SPIC | 179 |
| 7981728 | — | 2415 |
| 7981724 | — | 2440 |
| 7981730 | IGLJ3 | 9 |
| 7981732 | IGH@ | 311 |
| 7920244 | S100A8 | 2242 |
| 7981718 | IGHM | 12 |
| 8100827 | IGJ | 1500 |
| 7981740 | — | 2442 |
| 7922219 | SELL | 1997 |
| 8129637 | VNN2 | 117 |
| 8053690 | IGKC | 479 |
| 8011826 | C17orf87 | 323 |
| 8043431 | LOC652694 | 2470 |
| 7914270 | LAPTM5 | 1831 |
| 7981722 | IGHA1 | 312 |
| 7997712 | IRF8 | 560 |
| 7921667 | CD48 | 146 |
| 8043476 | LOC652493 | 2476 |
| 7903358 | VCAM1 | 2243 |
| 8043470 | — | 6 |
| 7948364 | MPEG1 | 1076 |
| 8139033 | AOAH | 2080 |
| 8014063 | EVI2B | 1128 |
| 8043449 | — | 7 |
| 8043465 | — | 2339 |
| 8043474 | LOC100130100 | 2475 |
| 7908553 | PTPRC | 940 |
| 7921873 | FCGR3A | 512 |
| 7920238 | S100A12 | 36 |
| 8043438 | — | 2472 |

TABLE 1-continued

| Probe Set ID | Gene Symbol | SEQ ID NO: |
| --- | --- | --- |
| 7995263 | — | 2338 |
| 7909371 | CR1 | 783 |
| 7903893 | CD53 | 802 |
| 8053713 | — | 2483 |
| 7898805 | C1QB | 787 |
| 8043433 | — | 157 |
| 7960794 | CD163 | 1092 |
| 8075910 | RAC2 | 222 |
| 7922773 | NCF2 | 1473 |
| 8043459 | LOC647506 | 2474 |
| 7983910 | AQP9 | 1262 |
| 7957023 | LYZ | 1375 |
| 7919800 | CTSS | 2235 |
| 8095886 | CXCL13 | 1588 |
| 8043468 | IGKC | 2336 |
| 8055980 | CYTIP | 1618 |
| 7940287 | MS4A1 | 678 |
| 8104901 | IL7R | 235 |
| 7906720 | FCER1G | 29 |
| 8089911 | HCLS1 | 1349 |
| 7923917 | FAIM3 | 1756 |
| 7981737 | — | 2441 |
| 8043981 | IL1R2 | 224 |
| 7909350 | CR2 | 1977 |
| 8057887 | STK17B | 1764 |
| 7986637 | — | 2446 |
| 8058905 | IL8RA | 237 |
| 7981601 | IGHD | 291 |
| 7898799 | C1QC | 1335 |
| 8173444 | IL2RG | 2058 |
| 8115076 | CSF1R | 1603 |
| 8038899 | FPR1 | 321 |
| 7905571 | S100A9 | 932 |
| 8030860 | FPR2 | 539 |
| 8178193 | HLA-DRA | 2163 |
| 8166730 | CYBB | 1315 |
| 8146500 | LYN | 1310 |
| 8000184 | IGSF6 | 818 |

TABLE 1-continued

| Probe Set ID | Gene Symbol | SEQ ID NO: |
| --- | --- | --- |
| 7903980 | C1orf162 | 172 |
| 7994769 | CORO1A | 2191 |
| 8118548 | HLA-DRA | 2163 |
| 8042391 | PLEK | 1246 |
| 7955908 | NCKAP1L | 1205 |
| 8061668 | IICK | 2044 |
| 7946033 | HBB | 229 |
| 7944152 | IL10RA | 1823 |
| 8036710 | GMFG | 1702 |
| 7934920 | LIPA | 1476 |
| 7953428 | CD4 | 2183 |
| 7991766 | HBA1 | 95 |
| 8048227 | IL8RB | 2012 |
| 8063115 | MMP9 | 714 |
| 7900426 | SMAP2 | 2216 |
| 8179489 | HLA-DQA1 | 520 |
| 8014891 | IKZF3 | 336 |
| 8152988 | SLA | 1561 |
| 8091523 | P2RY13 | 1557 |
| 8044049 | IL18RAP | 214 |
| 8004510 | CD68 | 804 |
| 8132819 | IKZF1 | 1123 |
| 7921625 | SLAMF6 | 2109 |
| 7898793 | C1QA | 786 |
| 8013450 | LGALS9B | 906 |
| 8116734 | LY86 | 557 |
| 8043441 | — | 2473 |
| 8179519 | HLA-DPB1 | 202 |
| 8180100 | HLA-DPA1 | 201 |
| 8001104 | — | 11 |
| 8140463 | FGL2 | 853 |
| 8178891 | HLA-DPA1 | 201 |
| 8136662 | MGAM | 1817 |
| 8005458 | LGALS9C | 907 |
| 8070826 | ITGB2 | 1462 |
| 8029136 | CD79A | 797 |
| 7945132 | FLI1 | 1536 |
| 7950307 | UCP2 | 77 |
| 8115147 | CD74 | 679 |

TABLE 1-continued

| Probe Set ID | Gene Symbol | SEQ ID NO: |
| --- | --- | --- |
| 8125530 | HLA-DMB | 2162 |
| 8157524 | TLR4 | 1660 |
| 7961532 | ARHGDIB | 574 |
| 7935337 | PIK3AP1 | 423 |
| 8133876 | CD36 | 1458 |
| 7953569 | PTPN6 | 1331 |
| 8049246 | INPP5D | 647 |
| 7948455 | MS4A6A | 185 |
| 8100798 | SULT1B1 | 1639 |
| 8180078 | HLA-DMB | 2162 |
| 8030277 | CD37 | 810 |
| 8096617 | BANK1 | 1987 |
| 8046003 | GCA | 1720 |
| 7921868 | FCGR3A | 512 |
| 8136557 | TBXAS1 | 1989 |
| 8174051 | BTK | 1728 |
| 8043436 | — | 2471 |
| 8178498 | HLA-B | 1387 |
| 7927964 | SRGN | 432 |
| 8036224 | TYROBP | 2060 |
| 7965573 | NTN4 | 828 |
| 8118594 | HLA-DPB1 | 202 |
| 8100971 | PPBP | 2112 |
| 8045563 | ARHGAP15 | 1450 |
| 7952022 | AMICA1 | 1150 |
| 7909214 | RASSF5 | 946 |
| 8177732 | HLA-A | 2011 |
| 8111739 | FYB | 396 |
| 7986293 | MCTP2 | 1895 |
| 8179103 | HLA-E | 2164 |
| 7968344 | ALOX5AP | 2291 |
| 7946579 | LYVE1 | 1186 |
| 7926451 | MRC1 | 1116 |
| 8124531 | HIST1H3I | 106 |
| 8179731 | HLA-B | 1387 |
| 7966127 | SELPLG | 2319 |
| 7956878 | IRAK3 | 1755 |
| 8176234 | CLIC2 | 655 |

TABLE 1-continued

| Probe Set ID | Gene Symbol | SEQ ID NO: |
| --- | --- | --- |
| 8153959 | DOCK8 | 1941 |
| 8117890 | HLA-E | 2164 |
| 7906786 | FCRLA | 401 |
| 7914112 | FGR | 914 |
| 8039212 | LILRB2 | 1868 |
| 8112428 | CD180 | 1352 |
| 8178489 | HLA-C//HLA-C | 523 |
| 8025103 | EMR1 | 376 |
| 8122176 | TCF21 | 1673 |
| 7973101 | RNASE6 | 1192 |
| 7899394 | C1orf38 | 1291 |
| 8115734 | LCP2 | 450 |
| 7899160 | CD52 | 676 |
| 8109843 | DOCK2 | 1649 |
| 8118111 | HCP5 | 1943 |
| 8124901 | HLA-C//HLA-C | 523 |
| 8001102 | — | 2458 |
| 8177527 | NAIP | 1013 |
| 7908409 | RGS2 | 1950 |
| 8178802 | HLA-DRB3 | 125 |
| 7960771 | CD163L1 | 755 |
| 7966089 | CMKLR1 | 1732 |
| 7983360 | B2M | 329 |
| 7915286 | PPT1 | 1760 |
| 8043360 | — | 6 |
| 8094240 | CD38 | 343 |
| 7981720 | — | 2383 |
| 8179276 | AIF1 | 1648 |
| 8172333 | CFP | 1845 |
| 8094743 | RHOH | 1129 |
| 8149137 | DEFA3 | 2097 |
| 8103494 | NPY1R | 2259 |
| 7904726 | TXNIP | 1395 |
| 8135594 | CAV1 | 2056 |
| 7956271 | HSD17B6 | 127 |
| 8084717 | ST6GAL1 | 2132 |
| 8001457 | CES1 | 680 |
| 7953603 | C1S | 1873 |
| 8141094 | PDK4 | 836 |

TABLE 1-continued

| Probe Set ID | Gene Symbol | SEQ ID NO: |
|---|---|---|
| 7922846 | FAM129A | 830 |
| 7960744 | C1R | 656 |
| 8142270 | NRCAM | 2177 |
| 8179331 | C2 | 1874 |
| 8135587 | CAV2 | 2322 |
| 8129618 | VNN1 | 1844 |
| 8032392 | MKNK2 | 1177 |
| 8118324 | C2 | 1874 |
| 8174103 | GK | 2307 |
| 7953200 | CCND2 | 1703 |
| 7979455 | RTN1 | 430 |
| 8126729 | CLIC5 | 1333 |
| 8179399 | C4A | 662 |
| 8122058 | ARG1 | 64 |
| 7926037 | PFKFB3 | 1853 |
| 8166632 | GK | 2307 |
| 7944876 | NRGN | 1420 |
| 8148059 | DEPDC6 | 1508 |
| 8162502 | FBP1 | 1299 |
| 8103789 | GPM6A | 395 |
| 8054945 | BIN1 | 154 |
| 7977397 | CRIP2 | 259 |
| 7987892 | ZFP106 | 70 |
| 8132929 | GBAS | 2272 |
| 8066214 | TGM2 | 351 |
| 7912937 | PADI2 | 1033 |
| 8099279 | ABLIM2 | 1556 |
| 7946661 | DKK3 | 651 |
| 7961230 | CSDA | 1862 |
| 7943998 | NNMT | 638 |
| 7906061 | SYT11 | 2088 |
| 8096489 | PDLIM5 | 1638 |
| 8004057 | KIF1C | 2064 |
| 7923516 | CYB5R1 | 483 |
| 8123739 | NRN1 | 316 |
| 8139270 | RASA4P | 1722 |
| 8056518 | SCN7A | 2324 |
| 7984932 | SCAMP5 | 2105 |
| 7931930 | PRKCQ | 466 |
| 8071036 | S100B | 931 |
| 8092750 | FGF12 | 2239 |
| 7922174 | F5 | 1015 |
| 7963851 | KIAA0748 | 1169 |
| 8107133 | PAM | 2079 |
| 8161520 | PGM5P2 | 1257 |
| 8133721 | HSPB1 | 1704 |
| 8049528 | LRRFIP1 | 1719 |
| 8080466 | ITIH3 | 1081 |
| 7915147 | FHL3 | 538 |
| 8141768 | RASA4 | 2142 |
| 7996219 | NDRG4 | 1578 |
| 8148501 | PTP4A3 | 96 |
| 8135069 | SERPINE1 | 1974 |
| 7926239 | OPTN | 567 |
| 8173600 | NAP1L2 | 2248 |
| 8173917 | NAP1L3 | 2244 |
| 8032834 | LRG1 | 484 |
| 8036591 | LGALS4 | 1582 |
| 7923824 | SLC41A1 | 513 |
| 7956856 | MSRB3 | 2165 |
| 7973580 | FIT1 | 1711 |
| 8033233 | TUBB4 | 145 |
| 8154962 | DNAJB5 | 2317 |
| 7983890 | GCOM1 | 2168 |
| 8042259 | MDH1 | 2218 |
| 8173551 | PHKA1 | 1381 |
| 8062971 | DBNDD2 | 2205 |
| 8046048 | CSRNP3 | 2047 |
| 8027719 | SCN1B | 1982 |
| 7983734 | TMOD2 | 1775 |
| 7901951 | PGM1 | 148 |
| 7914342 | FABP3 | 631 |
| 7957654 | AMDHD1 | 1856 |
| 8108251 | NPY6R | 2070 |
| 8113790 | MARCH3 | 1615 |
| 7997188 | HP | 1416 |
| 8024898 | FEM1A | 869 |

TABLE 1-continued

| Probe Set ID | Gene Symbol | SEQ ID NO: |
|---|---|---|
| 8038261 | GYS1 | 1913 |
| 7914557 | SYNC | 1340 |
| 8065372 | NAPE | 1622 |
| 7910164 | CABC1 | 867 |
| 7951662 | CRYAB | 20 |
| 8063177 | SLC2A10 | 350 |
| 8158059 | STXBP1 | 1884 |
| 8178298 | GABBR1 | 1344 |
| 8101874 | ADH1A | 2214 |
| 7958644 | ATP2A2 | 1307 |
| 7914075 | FCN3 | 221 |
| 8179595 | GABBR1 | 1344 |
| 7952785 | OPCML | 599 |
| 7965606 | HAL | 32 |
| 8039748 | A1BG | 1306 |
| 8072587 | SLC5A1 | 2067 |
| 7957338 | SYT1 | 1684 |
| 8046895 | FAM171B | 983 |
| 8155665 | PGM5 | 675 |
| 7964400 | STAC3 | 152 |
| 7956242 | COQ10A | 1184 |
| 8023889 | MBP | 681 |
| 8054377 | FHL2 | 394 |
| 8152703 | FBXO32 | 177 |
| 7978544 | EGLN3 | 1071 |
| 8012028 | ASGR2 | 2260 |
| 7985147 | DNAJA4 | 1563 |
| 7978586 | CFL2 | 1940 |
| 8076962 | MAPK12 | 472 |
| 8011975 | SLC13A5 | 1787 |
| 8004416 | CHRNB1 | 381 |
| 8037657 | DMPK | 1063 |
| 8154100 | VLDLR | 649 |
| 8132694 | IGFBP1 | 614 |
| 8149699 | PHYHIP | 1175 |
| 8017521 | SCN4A | 834 |
| 8029551 | APOC2 | 2301 |
| 8111892 | OXCT1 | 915 |

TABLE 1-continued

| Probe Set ID | Gene Symbol | SEQ ID NO: |
|---|---|---|
| 7937728 | TNNI2 | 1872 |
| 8166355 | CNKSR2 | 2021 |
| 8049737 | AGXT | 1398 |
| 7908459 | CFH | 1413 |
| 8007607 | RUNDC3A | 1809 |
| 7899841 | HPCA | 130 |
| 8100154 | CORIN | 239 |
| 8053984 | ANKRD23 | 795 |
| 7920472 | TPM3 | 929 |
| 8125780 | IP6K3 | 1773 |
| 8001041 | COX6A2 | 2298 |
| 7950321 | UCP3 | 1735 |
| 8161044 | TPM2 | 461 |
| 8039779 | SLC27A5 | 1813 |
| 7943711 | C11orf87 | 440 |
| 7922482 | TNR | 1267 |
| 7973084 | ANG | 1664 |
| 8054338 | CREG2 | 1731 |
| 8126760 | RCAN2 | 970 |
| 8081288 | TMEM45A | 51 |
| 8078386 | GPD1L | 2092 |
| 8168470 | COX7B | 121 |
| 8030557 | ATF5 | 2178 |
| 8140249 | GATSL2 | 1935 |
| 7958860 | RPH3A | 1789 |
| 7907370 | DNM3 | 1700 |
| 8172317 | SYN1 | 813 |
| 7937749 | TNNT3 | 1412 |
| 7942453 | PLEKHB1 | 1546 |
| 7947828 | MYBPC3 | 1144 |
| 7902495 | NEXN | 1161 |
| 8162216 | SHC3 | 2179 |
| 8048673 | SLC4A3 | 1283 |
| 7947801 | PACSIN3 | 2123 |
| 7976496 | SERPINA3 | 708 |
| 8105596 | RGS7BP | 691 |
| 8100746 | UGT2B15 | 975 |
| 8024754 | CREB3L3 | 89 |
| 8016128 | GFAP | 1609 |

TABLE 1-continued

| Probe Set ID | Gene Symbol | SEQ ID NO: |
|---|---|---|
| 8151223 | SLCO5A1 | 1878 |
| 8083779 | SERPINI1 | 1385 |
| 8006445 | CCL11 | 173 |
| 8061605 | MYLK2 | 1332 |
| 8162254 | DIRAS2 | 437 |
| 7979505 | SIX1 | 1418 |
| 7908841 | PPP1R12B | 2007 |
| 8172573 | SYP | 578 |
| 8045795 | KCNJ3 | 203 |
| 8066590 | TNNC2 | 373 |
| 8162777 | GABBR2 | 2039 |
| 7955078 | PFKM | 2005 |
| 7923528 | MYOG | 944 |
| 8045018 | PROC | 2018 |
| 8098379 | WDR17 | 2006 |
| 8163109 | C9orf4 | 957 |
| 7968734 | SLC25A15 | 1905 |
| 8115122 | CAMK2A | 1725 |
| 7910265 | OBSCN | 1157 |
| 7981078 | SERPINA11 | 1027 |
| 8159583 | GRIN1 | 2129 |
| 8014794 | CACNB1 | 370 |
| 8039353 | TNNI3 | 1183 |
| 8120654 | KCNQ5 | 1903 |
| 8023710 | CDH19 | 108 |
| 8089714 | LSAMP | 1959 |
| 7981051 | SERPINA10 | 1218 |
| 8003656 | SERPINF2 | 1036 |
| 8056877 | CHRNA1 | 1506 |
| 8088047 | MUSTN1 | 2215 |
| 8045974 | SLC4A10 | 1223 |
| 8059580 | DNER | 966 |
| 8040073 | FLJ30594 | 159 |
| 7964987 | KCNC2 | 195 |
| 7998643 | RPL3L | 112 |
| 8149877 | PNMA2 | 1255 |
| 7934384 | ZMYND17 | 664 |
| 8117178 | NRSN1 | 1490 |

TABLE 1-continued

| Probe Set ID | Gene Symbol | SEQ ID NO: |
|---|---|---|
| 8139307 | MYL7 | 497 |
| 8040960 | GCKR | 1821 |
| 8006509 | UNC45B | 725 |
| 8066407 | C20orf142 | 1028 |
| 8121672 | VGLL2 | 287 |
| 8077270 | CHL1 | 226 |
| 8123232 | SLC22A1 | 188 |
| 7997491 | HSD17B2 | 1705 |
| 7994804 | MYLPF | 1104 |
| 8006433 | CCL2 | 563 |
| 8026579 | TMEM38A | 76 |
| 8008277 | SGCA | 1677 |
| 8076644 | SULT4A1 | 800 |
| 8079107 | KBTBD5 | 427 |
| 8141560 | TFR2 | 891 |
| 8101893 | ADH1C | 694 |
| 8009343 | CACNG1 | 2222 |
| 8019243 | DYSFIP1 | 963 |
| 7950764 | DLG2 | 1769 |
| 8028084 | APLP1 | 665 |
| 7923360 | TNNI1 | 576 |
| 7923332 | TNNT2 | 465 |
| 8117748 | MOG | 2150 |
| 8027819 | HAMP | 493 |
| 7912520 | NPPB | 752 |
| 8129924 | TXLNB | 1834 |
| 8053602 | PLGLB2 | 1035 |
| 8039340 | TNNT1 | 1421 |
| 8124365 | SLC17A2 | 2085 |
| 8127872 | SNAP91 | 1808 |
| 8049610 | KLHL30 | 2042 |
| 8144917 | LPL | 1115 |
| 8013947 | CORO6 | 1952 |
| 7974270 | ATL1 | 1486 |
| 7956423 | INHBC | 105 |
| 7995739 | GNAO1 | 1311 |
| 7913593 | TCEA3 | 388 |
| 8046461 | ZAK | 745 |
| 8072039 | MYO18B | 509 |

TABLE 1-continued

| Probe Set ID | Gene Symbol | SEQ ID NO: |
|---|---|---|
| 7966621 | SDS | 283 |
| 8004309 | SLC2A4 | 753 |
| 8030677 | MYBPC2 | 1079 |
| 7926715 | GPR158 | 826 |
| 7903227 | PALMD | 1636 |
| 7933665 | MBL2 | 1399 |
| 8109383 | GRIA1 | 1346 |
| 8100109 | GABRA2 | 1345 |
| 8144322 | MYOM2 | 1231 |
| 7920082 | RORC | 469 |
| 8063129 | SLC12A5 | 1644 |
| 8001163 | MYLK3 | 1122 |
| 8081620 | TAGLN3 | 568 |
| 8028407 | RYR1 | 924 |
| 7981020 | ASB2 | 2271 |
| 8152715 | KLHL38 | 1545 |
| 8099218 | PPP2R2C | 878 |
| 8152512 | TNFRSF11B | 1153 |
| 8034263 | ELAVL3 | 480 |
| 8103544 | SPOCK3 | 821 |
| 8088020 | ITIH4 | 1994 |
| 8086419 | HHATL | 1915 |
| 8108006 | LEAP2 | 856 |
| 7918449 | KCNA2 | 2281 |
| 8047248 | PLCL1 | 1360 |
| 8044700 | DPP10 | 2093 |
| 8177709 | MOG | 2022 |
| 8132318 | ANLN | 265 |
| 8027824 | MAG | 2220 |
| 8077944 | CAND2 | 1929 |
| 8092277 | PEX5L | 47 |
| 7919929 | TMOD4 | 1238 |
| 7929653 | ANKRD2 | 352 |
| 7963880 | ITGA7 | 1832 |
| 7912361 | MASP2 | 2290 |
| 8163535 | AMBP | 1445 |
| 7979615 | SPTB | 2004 |
| 8040898 | TRIM54 | 2170 |
| 8038367 | SLC17A7 | 1815 |
| 7955533 | FLJ33996 | 158 |
| 8146703 | C8orf46 | 1625 |
| 8148029 | COLEC10 | 1953 |
| 8077833 | SLC6A1 | 1453 |
| 7935288 | OPALIN | 811 |
| 7901720 | PRKAA2 | 1293 |
| 7999364 | GRIN2A | 1631 |
| 7961422 | GRIN2B | 1347 |
| 8175696 | GABRA3 | 1244 |
| 8111998 | HCN1 | 974 |
| 7921003 | C1orf61 | 37 |
| 8157027 | NIPSNAP3B | 149 |
| 7977987 | MYH6 | 2054 |
| 7940673 | GNG3 | 1630 |
| 8057377 | CCDC141 | 2144 |
| 8137010 | CNTNAP2 | 2053 |
| 8092836 | CPN2 | 1955 |
| 7910792 | RYR2 | 921 |
| 8086222 | SCN5A | 1179 |
| 7939706 | F2 | 1379 |
| 7902977 | KIAA1107 | 1623 |
| 8059551 | SPHKAP | 1763 |
| 8027760 | FXYD1 | 219 |
| 8101952 | DDIT4L | 2201 |
| 8179011 | MOG | 2022 |
| 8080028 | DOCK3 | 2184 |
| 8055969 | ERMN | 586 |
| 8179762 | ATP6V1G2 | 2277 |
| 8160321 | SLC24A2 | 2155 |
| 8147012 | PKIA | 2303 |
| 8067652 | EEF1A2 | 205 |
| 7977273 | ADSSL1 | 362 |
| 7961626 | SLCO1A2 | 1766 |
| 7912515 | NPPA | 1922 |
| 7997289 | CNTNAP4 | 972 |
| 7983928 | LIPC | 1542 |
| 8154953 | KIAA1045 | 1171 |
| 8168291 | ITGB1BP2 | 41 |

TABLE 1-continued

| Probe Set ID | Gene Symbol | SEQ ID NO: |
|---|---|---|
| 8178115 | CFB | 1487 |
| 8044094 | TMEM182 | 1455 |
| 7923271 | CACNA1S | 895 |
| 7986195 | SV2B | 2000 |
| 7933640 | A1CF | 2211 |
| 7949719 | PC | 873 |
| 7918794 | AMPD1 | 2050 |
| 7905329 | MLLT11 | 556 |
| 8110074 | HMP19 | 299 |
| 8120468 | BAI3 | 1263 |
| 8042993 | CTNNA2 | 1969 |
| 7934755 | MAT1A | 667 |
| 8133904 | GRM3 | 442 |
| 8121814 | NKAIN2 | 835 |
| 8118345 | CFB | 1487 |
| 8130436 | — | 2372 |
| 8086457 | CYP8B1 | 1337 |
| 7999093 | SRL | 1168 |
| 7946983 | SAA2 | 2236 |
| 7929487 | CYP2C9 | 1493 |
| 8006896 | TCAP | 1693 |
| 8035095 | CYP4F11 | 1530 |
| 7909306 | C4BPB | 633 |
| 7994463 | ATP2A1 | 2143 |
| 8092661 | MASP1 | 2083 |
| 8145122 | SLC39A14 | 1656 |
| 7939237 | C11orf41 | 2173 |
| 7983228 | MAP1A | 852 |
| 8149725 | PEBP4 | 982 |
| 7982366 | SCG5 | 1798 |
| 8121152 | FUT9 | 1096 |
| 8109490 | SGCD | 1507 |
| 8083301 | TM4SF4 | 2304 |
| 8081036 | CADM2 | 2003 |
| 8151525 | PMP2 | 415 |
| 8080445 | ITIH1 | 1232 |
| 7972650 | FGF14 | 1415 |
| 7997192 | HPR | 426 |
| 7907053 | DUSP27 | 1026 |
| 8078920 | MOBP | 877 |
| 8109663 | GABRA1 | 1472 |
| 7940135 | GLYATL1 | 262 |
| 8056457 | SCN1A | 956 |
| 7900365 | MFSD2 | 1712 |
| 8048541 | DES | 551 |
| 8100097 | GABRG1 | 597 |
| 7930561 | HABP2 | 1380 |
| 8074399 | CLTCL1 | 1931 |
| 7930208 | INA | 1627 |
| 7985620 | ALPK3 | 1767 |
| 8101852 | ADH4 | 695 |
| 8098021 | GRIA2 | 1094 |
| 8048026 | CPS1 | 2312 |
| 8068620 | SH3BGR | 473 |
| 8114263 | LECT2 | 596 |
| 7972902 | ADPRHL1 | 363 |
| 8111474 | AGXT2 | 2099 |
| 8151042 | TTPA | 1999 |
| 7946977 | SAA4 | 2237 |
| 7955858 | HOXC10 | 760 |
| 8064928 | HAO1 | 66 |
| 8060963 | SNAP25 | 126 |
| 7934434 | MYOZ1 | 144 |
| 8080855 | SYNPR | 1538 |
| 8036151 | HSPB6 | 151 |
| 7927474 | C10orf71 | 1659 |
| 8084100 | USP13 | 1748 |
| 7964142 | APOF | 501 |
| 8012753 | MYH2 | 1206 |
| 7931748 | IDI2 | 150 |
| 8093137 | C3orf43 | 992 |
| 8156905 | TMEFF1 | 2210 |
| 8152291 | ABRA | 1499 |
| 8101637 | HSD17B13 | 1706 |
| 7902235 | LRRC7 | 918 |
| 7981059 | SERPINA6 | 709 |
| 8005048 | MYOCD | 1889 |

TABLE 1-continued

| Probe Set ID | Gene Symbol | SEQ ID NO: |
|---|---|---|
| 8129695 | ALDH8A1 | 2166 |
| 7947496 | SLC1A2 | 991 |
| 8098576 | SLC25A4 | 1965 |
| 8038319 | HRC | 726 |
| 7902290 | CTH | 2139 |
| 7931643 | CYP2E1 | 724 |
| 8157446 | ORM1 | 1359 |
| 8138310 | DGKB | 1543 |
| 8021741 | CNDP1 | 617 |
| 7929466 | CYP2C18 | 1528 |
| 8037949 | SULT2A1 | 1869 |
| 7908492 | CFHR4 | 2273 |
| 7957373 | MYF6 | 2108 |
| 7971922 | PCDH9 | 1848 |
| 7935679 | CPN1 | 1069 |
| 7908496 | CFHR2 | 485 |
| 7954356 | SLCO1B1 | 1877 |
| 7903214 | LPPR4 | 1988 |
| 8035083 | CYP4F2 | 82 |
| 8141052 | PON1 | 1682 |
| 7908499 | CFHR5 | 1321 |
| 7904965 | PDE4DIP | 65 |
| 7983718 | SCG3 | 1972 |
| 7916526 | C8B | 702 |
| 8109677 | GABRG2 | 1475 |
| 8145361 | NEFM | 1289 |
| 7935930 | KCNIP2 | 495 |
| 7922420 | SERPINC1 | 1939 |
| 8174304 | SERPINA7 | 2098 |
| 8094901 | GABRB1 | 1540 |
| 8094778 | UCHL1 | 1919 |
| 7908488 | CFHR1 | 997 |
| 7935169 | CYP2C8 | 861 |
| 7908481 | CFHR3 | 1998 |
| 7901732 | C8A | 1739 |
| 8112980 | EDIL3 | 252 |
| 8135821 | LMOD2 | 1178 |
| 7913907 | TRIM63 | 133 |
| 8086615 | LRRC2 | 1509 |
| 8081959 | STXBP5L | 1355 |
| 8146393 | C8orf22 | 1156 |
| 8162870 | BAAT | 1477 |
| 7906458 | APCS | 1657 |
| 8002556 | TAT | 1377 |
| 7930714 | ATRNL1 | 885 |
| 8157450 | ORM2 | 375 |
| 7982052 | PAR4 | 1407 |
| 8028963 | CYP2B6 | 139 |
| 7909318 | C4BPA | 632 |
| 8020973 | FHOD3 | 588 |
| 7907249 | FMO3 | 1945 |
| 8135405 | GPR22 | 801 |
| 8141317 | CYP3A4 | 2276 |
| 8105487 | RAB3C | 294 |
| 8155734 | C9orf61 | 1469 |
| 8046020 | SCN2A | 823 |
| 8109752 | ODZ2 | 1569 |
| 7963142 | FAIM2 | 2313 |
| 7946986 | SAA1 | 2089 |
| 7904396 | HAO2 | 543 |
| 7934442 | SYNPO2L | 1339 |
| 7923034 | B3GALT2 | 1671 |
| 7961580 | LMO3 | 387 |
| 7919028 | TBX15 | 554 |
| 8004043 | ENO3 | 2169 |
| 7921449 | CRP | 553 |
| 7907222 | PRRX1 | 577 |
| 8170215 | F9 | 1411 |
| 7926506 | CACNB2 | 1124 |
| 8127177 | KLHL31 | 1181 |
| 8156706 | TMOD1 | 1985 |
| 8058604 | MYL1 | 951 |
| 8172043 | SRPX | 2028 |
| 8089785 | POPDC2 | 170 |
| 8122150 | EYA4 | 1492 |
| 8049349 | UGT1A1 | 429 |
| 8119403 | APOBEC2 | 1883 |

TABLE 1-continued

| Probe Set ID | Gene Symbol | SEQ ID NO: |
|---|---|---|
| 8086341 | XIRP1 | 360 |
| 7963826 | PPP1R1A | 1222 |
| 8171403 | ASB11 | 2268 |
| 8083415 | AADAC | 673 |
| 7913727 | MYOM3 | 1224 |
| 7902452 | AK5 | 2267 |
| 8012726 | MYH1 | 950 |
| 7935188 | SORBS1 | 739 |
| 8098671 | F11 | 979 |
| 7934997 | PPP1R3C | 1102 |
| 7933904 | CTNNA3 | 1452 |
| 8151423 | JPH1 | 606 |
| 8112841 | HOMER1 | 438 |
| 8111757 | C9 | 1427 |
| 7904717 | HFE2 | 1410 |
| 8103812 | ASB5 | 2140 |
| 8092083 | SLC2A2 | 28 |
| 8156919 | MURC | 658 |
| 7906552 | CASQ1 | 1894 |
| 8092970 | APOD | 1604 |
| 8100131 | GABRA4 | 2280 |
| 8055711 | NEB | 1964 |
| 8106689 | CKMT2 | 1191 |
| 7978021 | MYH7 | 949 |
| 8135990 | FLNC | 1463 |
| 8084668 | FRG | 84 |
| 8095663 | AFM | 220 |
| 7943892 | NCAM1 | 986 |
| 7971444 | CPB2 | 1068 |
| 7997504 | CDH13 | 605 |
| 7901883 | ANGPTL3 | 383 |
| 8129330 | TRDN | 868 |
| 8138888 | PDE1C | 2156 |
| 8007429 | G6PC | 1014 |
| 8149521 | FGL1 | 402 |
| 7967212 | HPD | 332 |
| 8097801 | FAM160A1 | 1298 |
| 7916616 | CYP2J2 | 124 |

TABLE 1-continued

| Probe Set ID | Gene Symbol | SEQ ID NO: |
|---|---|---|
| 7982070 | SNRPN//SNORD115-32 | 1047 |
| 7968004 | SGCG | 1687 |
| 7938951 | ANO5 | 1765 |
| 8111136 | FAM134B | 735 |
| 8141066 | PON3 | 843 |
| 8033257 | C3 | 938 |
| 7993737 | ACSM2A | 1217 |
| 8088739 | LMOD3 | 1547 |
| 7947099 | CSRP3 | 1474 |
| 8081997 | FBXO40 | 1243 |
| 8108256 | MYOT | 1690 |
| 7908312 | PRG4 | 1481 |
| 8100853 | GC | 2282 |
| 7999965 | ACSM2B | 1266 |
| 7928838 | LDB3 | 1024 |
| 7912692 | HSPB7 | 1320 |
| 8022655 | AQP4 | 500 |
| 7962559 | SLC38A4 | 1785 |
| 8097086 | MYOZ2 | 1439 |
| 8117045 | RBM24 | 1799 |
| 8142435 | PPP1R3A | 1353 |
| 7927827 | MYPN | 1202 |
| 7973850 | AKAP6 | 1585 |
| 8171921 | DMD | 1908 |
| 8075659 | MB | 412 |
| 8062461 | LBP | 264 |
| 8100557 | SRD5A2L2 | 1614 |
| 8102877 | CLGN | 1580 |
| 7983650 | SLC27A2 | 1896 |
| 7969438 | LMO7 | 1792 |
| 7927694 | PHYHIPL | 1778 |
| 7917996 | LRRC39 | 1099 |
| 7993083 | A2BP1 | 1738 |
| 7957966 | MYBPC1 | 433 |
| 7965884 | PAH | 27 |
| 8123259 | PLG | 2014 |
| 8127646 | FILIP1 | 448 |
| 8037525 | CKM | 2138 |
| 8095806 | ART3 | 1544 |

TABLE 1-continued

| Probe Set ID | Gene Symbol | SEQ ID NO: |
|---|---|---|
| 7936360 | NRAP | 434 |
| 8057056 | TTN | 2059 |
| 7966379 | MYL2 | 1518 |
| 8084679 | KNG1 | 1995 |
| 8171791 | SMPX | 54 |
| 7938758 | SAA1 | 2089 |
| 7910727 | ACTN2 | 1305 |
| 8162884 | ALDOB | 1770 |
| 8046062 | XIRP2 | 2219 |
| 8117054 | CAP2 | 380 |
| 8121729 | PLN | 1559 |
| 8022045 | MYOM1 | 1098 |
| 8043381 | SMYD1 | 2199 |
| 8111864 | C6 | 1371 |
| 7918878 | CASQ2 | 1467 |
| 8046160 | KBTBD10 | 405 |
| 8063590 | PCK1 | 1423 |
| 8106556 | CMYA5 | 616 |
| 8120300 | C6orf142 | 1215 |
| 8141374 | AZGP1 | 1991 |

Thus, for example, an agent may be qualified as being safe if less than about 5% of the tissue specific genes of one particular tissue are differentially expressed. According to another embodiment, an agent may be qualified as being safe if less than about 4.5% of the tissue specific genes of a certain tissue are differentially expressed. According to another embodiment, an agent may be qualified as being safe if less than about 4% of the tissue specific genes of a certain tissue are differentially expressed. According to another embodiment, an agent may be qualified as being safe if less than about 3.5% of the tissue specific genes of a certain tissue are differentially expressed. According to another embodiment, an agent may be qualified as being safe if less than about 3% of the tissue specific genes of a certain tissue are differentially expressed. According to another embodiment, an agent may be qualified as being safe if less than about 2.5% of the tissue specific genes of a certain tissue are differentially expressed. According to another embodiment, an agent may be qualified as being safe if less than about 2% of the tissue specific genes of a certain tissue are differentially expressed.

Thus for example in the case of a non-biased chip being able to detect about 30,000 genes in general, and about 200 tissue specific genes of a certain tissue, an agent may be qualified as being safe if less than about 10 tissue specific genes are differentially expressed.

The present inventors have further found that if a gene which is found to be differentially expressed is involved in a pathway important for fetal development, then similarly to the tissue specific genes, this bears more weight than a gene not involved in fetal development on the ascertainment of safety. Such genes include, but are not limited to those belonging to pathways that are critical for correct patterning and specification of the central nervous system (e.g. Hox pathway genes, Notch pathway genes, Wnt pathway genes) and metabolic pathways, and those related to oxidative stress, and those related to growth factor signaling (e.g. EGF pathway genes, FGF pathway genes, BMP pathway genes, TGFB pathway genes), and those related to cell contact and adhesion (e.g. Integrin genes, Cadherin genes, ECM protein genes).

Examples of genes which the present inventors have set as being involved in fetal development include but are not limited to NRP2, HOXA5, ISL1, NODAL, CER1, APOA4, TTR, AFP, BMP4, MSX2, MEIS1. Additional fetal development associated genes may be found on the Gene onthology database.

Thus, for example, an agent may be qualified as being safe if no more than about 3% of those that are differentially expressed are involved in fetal development. According to another embodiment, an agent may be qualified as being safe if no more than about 3.5% of those that are differentially expressed are involved in fetal development. According to another embodiment, an agent may be qualified as being safe if no more than about 4% of those that are differentially expressed are involved in fetal development. According to another embodiment, an agent may be qualified as being safe if no more than about 4.5% of those that are differentially expressed are involved in fetal development.

Thus for example in the case of a non-biased chip being able to detect about 30,000 genes, an agent may be qualified as being safe if less than about 300 genes altogether are differentially expressed, of which no more than 12 are fetal development associated genes.

The analysis as to whether an agent is safe or not may be determined based on total number of differential genes; a combination of total number of differential genes and number of differentially expressed tissue specific genes; a combination of total number of differential genes and number of differentially expressed fetal development-associated genes; or a combination of the number of differentially expressed tissue specific genes and the number of differentially expressed fetal development-associated genes; and also a combination of the total number of differentially expressed genes, the number of differentially expressed tissue specific genes and the number of differentially expressed fetal development-associated genes.

It will be appreciated that in order to limit the number of genes being analyzed for expression, a non-random, set of genes may be selected which is biased towards either tissue specific genes or fetal development associated genes or both.

As mentioned, the percent of tissue specific genes in the human genome is about 3%. Thus, the present inventors contemplate analysis of a tissue specific biased gene set wherein about at least 6% of the genes may be defined as tissue specific, at least 12% of the genes may be defined as tissue specific, at least 20% of the genes may be defined as tissue specific, at least 25% of the genes may be defined as tissue specific, at least 30% of the genes may be defined as tissue specific, at least 35% of the genes may be defined as tissue specific, at least 40% of the genes may be defined as tissue specific, at least 45% of the genes may be defined as tissue specific, at least 50% of the genes may be defined as tissue specific, at least 55% of the genes may be defined as tissue specific, at least 60% of the genes may be defined as tissue specific, at least 65% of the genes may be defined as tissue specific, at least 70% of the genes may be defined as tissue specific, at least 75% of the genes may be defined as tissue specific, at least 80% of the genes may be defined as tissue specific, at least 85% of the genes may be defined as tissue specific. The remaining genes which are being analyzed may be a random set of genes, biased towards another function (e.g. involved in fetal development) and/or may be control genes (e.g. housekeeping genes, known not to change during differentiation of embryonic stem cells).

According to one embodiment, in a tissue specific-biased array, the number of representative genes for each tissue is similar—i.e. the percentage of heart specific genes on the array should be approximately the same as the brain specific genes, liver, skeletal muscle and blood.

According to another embodiment, the array is biased towards genes associated with a particular tissue.

As mentioned, the percent of tissue specific genes in the human genome is about 10%. Thus, the present inventors contemplate analysis of a tissue specific biased gene set wherein about at least 20% of the genes may be defined as being associated with fetal development, at least 25% of the genes may be defined as being associated with fetal development, at least 30% of the genes may be defined as being associated with fetal development, at least 35% of the genes may be defined as being associated with fetal development, at least 40% of the genes may be defined as being associated with fetal development, at least 45% of the genes may be defined as as being associated with fetal development, at least 50% of the genes may be defined as being associated with fetal development, at least 55% of the genes may be defined as being associated with fetal development, at least 60% of the genes may be defined as being associated with fetal development, at least 65% of the genes may be defined as being associated with fetal development, at least 70% of the genes may be defined as being associated with fetal development, at least 75% of the genes may be defined as being associated with fetal development, at least 80% of the genes may be defined as being associated with fetal development, at least 85% of the genes may be defined as being associated with fetal development. The remaining genes which are being analyzed may be a random set of genes, biased towards another function (e.g. involved in fetal development) and/or may be control genes (e.g. housekeeping genes, known not to change during differentiation of embryonic stem cells).

No matter how many genes are being analyzed, it is important to set a lower limit for the number of tissue specific genes or fetal development specific genes above which an agent may be qualified as being toxic. Thus, according to a particular embodiment, in order to determine toxicity of an agent, more than about 3 tissue specific genes of one particular tissue should be differentially expressed. According to another embodiment, in order to determine toxicity of an agent, more than about 5 tissue specific genes of one particular tissue should be differentially expressed. According to another embodiment, in order to determine safety of an agent, more than about 7 tissue specific genes of one particular tissue should be differentially expressed. According to another embodiment, in order to determine safety of an agent, more than about 10 tissue specific genes of one particular tissue should be differentially expressed.

Thus, according to another particular embodiment, in order to determine toxicity of an agent, more than about 20 fetal development associated genes should be differentially expressed. According to another embodiment, more than about 25 fetal development associated genes should be differentially expressed in order to determine toxicity. According to another embodiment, more than about 30 fetal development associated genes should be differentially expressed in order to determine toxicity. According to another embodiment, more than about 35 fetal development associated genes should be differentially expressed in order to determine toxicity.

It will be appreciated that by increasing the percent of tissue specific genes or fetal development associated genes that are analyzed, the total number of genes may be decreased compared to a random global array, since the significance of these particular genes is greater than a gene non involved in tissue specificity or fetal development.

Exemplary biased arrays that may be used according to this aspect of the present invention include those wherein at least 10% of the array is capable of identifying tissue specific genes and an additional 10% of the array is capable of identifying fetal development associated genes. An additional contemplated array is one in which at least 10% of the array is capable of identifying tissue specific genes and an additional 20% of the array is capable of identifying fetal development associated genes. An additional contemplated array is one in which at least 10% of the array is capable of identifying tissue specific genes and an additional 40% of the array is capable of identifying fetal development associated genes. An additional contemplated array is one in which at least 20% of the array is capable of identifying tissue specific genes and an additional 10% of the array is capable of identifying fetal development associated genes. An additional contemplated array is one in which at least 20% of the array is capable of identifying tissue specific genes and an additional 20% of the array is capable of identifying fetal development associated genes. An additional contemplated array is one in which at least 20% of the array is capable of identifying tissue specific genes and an additional 40% of the array is capable of identifying fetal development associated genes. An additional contemplated array is one in which at least 40% of the array is capable of identifying tissue specific genes and an additional 10% of the array is capable of identifying fetal development associated genes. An additional contemplated array is one in which at least 40% of the array is capable of identifying tissue specific genes and an additional 20% of the array is capable of identifying fetal development associated genes. An additional contemplated array is one in which at least 40% of the array is capable of identifying tissue specific genes and an additional 40% of the array is capable of identifying fetal development associated genes.

Following the determination of safety of a particular agent, the present invention contemplates testing that agent using additional safety tests, teratogenicity tests and other quality assurance tests known in the art. Such tests may include testing the agent in vivo (e.g. mice, rabbits, monkeys etc.). The results of such tests may be documented and relayed to the relevant parties.

In one such test, the test substance is administered to pregnant animals from implantation to one day prior to the day of scheduled kill which should be as close as possible to the normal day of delivery (usually day 21 of gestation in rats and day 29 of gestation in rabbits). It is recommended that testing be performed in one rodents species (preferred rat) and in one non-rodent species (rabbit). The animals may be divided in at least four groups containing a sufficient number of females to result in approximately 20 pregnant animals/group. At least three dose levels and a concurrent control should be used. This last group should be a sham-treated control group or a vehicle-control group if a vehicle is used in administering the test substance. It is very important to use different dose levels because embryotoxic effects (i.e all the possible adverse effects on a conceptus) are strictly dose-related and the dose levels should be spaced to produce a gradation of toxic effects. In particular, to maximize the possible adverse effects and to be sure that the conceptus will be exposed to the highest possible level, the highest dose should be chosen with the aim to induce some maternal toxicity (e.g., a minimal decrease in maternal body weight gain in comparison to control). The lowest dose level should not produce any evidence of either maternal or developmental toxicity, it should be the No Observed Adverse Effect Level (NOAEL). It is very important to find out the NOAEL because this dose could be necessary in case of risk assessment evaluation.

The test substance (or vehicle) is usually administered daily, orally by intubation. If other routes of administration are used, they must be justified. In order to verify signs of toxicity (or abortion) the pregnant animals must be observed after treatment and their conditions recorded; besides, they must be weighed at least every three days during the treatment period and on the day of scheduled kill. Immediately after killing the dams must be necropsied in order to verify pathological changes. The uteri must be removed and carefully examined in order to count the number of implantation and signs of resorptions (dead embryos). The foetuses must be examined for external abnormalities, weighed and afterwards examined for visceral and skeletal abnormalities using adequate methods.

A "Reproduction toxicity study" or "Two generation reproduction toxicity test" may also be performed following the test of the present invention. This study is designed to provide information concerning the effects of the test substance on the male and female reproductive systems (i.e., general aspects of fertility), gestation, parturition, lactation and weaning, and the growth and development of the offspring. The rat is the preferred species for testing and the test substance should be administered by oral route (mixed in the diet or water, or by intubation). One control and three test groups are typically required. The males should be treated for at least one complete spermatogenic cycle (about 70 days) before mating; the females for at least three oestrous cycle (2 weeks) before mating, during mating, pregnancy and lactation. At weaning, the treatment is continued to F1 offspring during their growth into adulthood, mating and production of an F2 generation, until the F2 generation is weaned. It will be appreciated that this test may furnish important information on number of live pups, their weight at birth, and postnatal viability and development.

The present invention also contemplates kits for ascertaining the bio-safety of an agent. The kit may comprise an array which detects expression levels of a plurality of genes, wherein a minimum number of genes is about 20 and a maximum number of genes is about 1000, wherein at least 30% of the genes are tissue specific genes (the number of representative genes for each tissue being similar) selected from the group consisting of those listed in Table 1.

According to one embodiment, the number of genes that may be analyzed on the array is about 50, about 100, about 150, about 200, about 250, about 300, about 350, about 400, about 450, or about 500.

According to yet another embodiment, at least 35% of the genes are the tissue specific genes.

According to yet another embodiment, at least 40% of the genes are the tissue specific genes.

According to yet another embodiment, at least 45% of the genes are the tissue specific genes.

According to yet another embodiment, at least 50% of the genes are the tissue specific genes.

According to still another embodiment, at least 20% of the remaining genes are genes involved in fetal development.

According to still another embodiment, at least 30% of the remaining genes are genes involved in fetal development.

According to still another embodiment, at least 40% of the remaining genes are genes involved in fetal development.

The detection arrays described herein are preferably packaged in kits identified for use in analyzing the safety of an agent. The kit can further include reagents suitable for the detection of polynucleotide hybridization or antibody binding and instructions for effecting the determination using the kit components and suitable detection hardware (e.g., detection microscope) and software (e.g., detection and analysis software). For further description of such hardware and software and detection reagents please see worldwidewebdotaffymetrixdotcom.

As used herein the term "about" refers to ±10%.

The terms "comprises", "comprising", "includes", "including", "having" and their conjugates mean "including but not limited to".

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental or calculated support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Cell culture: Human ES cells (HESCs, H9) and induced-pluripotent stem cells (HiPSCs, hTERT-BJ1 derived clone #28) [19], were cultured on Mitomycin-C treated mouse embryonic fibroblast (MEF) feeder layer (obtained from 13.5 day embryos) in 85% KnockOut DMEM medium (GIBCO-BRL), supplemented with 15% KnockOut SR (a serum free formulation) (GIBCO-BRL), 1 mM glutamine, 0.1 mM β-mercaptoethanol (Sigma), 1% nonessential amino acids stock (GIBCO-BRL), Penicillin (50 units/ml), Streptomycin (50 μg/ml) and 4 ng/ml basic fibroblast growth factor (FGF2, PeproTech-Cytolab, Rehovot, Israel). HiPSC#28 was previously derived and characterized as described by Pick et al. (2009). In brief, hTERT-BJ1 cells were infected with a combination of the human OCT4, SOX2, MYC and KLF4 genes packaged in pMXs retroviral vectors. Cells were passaged using trypsin-EDTA (Biological industries, Beit-Haemek, Israel). To obtain feeder free cultures, cells were plated on laminin (1 μg/cm$^2$, Sigma) or gelatin (0.1%, Merck) coated plates and grown with medium conditioned by MEFs (CM). Differentiation in-vitro into embryoid bodies (EBs) was performed by trypsinizing confluent cultures using 0.25% trypsin-A in DPBS solution (Biological industries, Beit-Haemek, Israel) for 15 seconds to dissociate the colonies into large clumps. Clumps were then transferred 1:1 into non-stick petri dishes and grown in regular HESC medium but without exogenous FGF2.

Drug treatments: Embryoid body media were supplemented with the various treatment compounds on the first day and changed on alternate days. Ethanol 100% (Bio-Lab, Jerusalem, Israel) was used at 0.5%, 1.5%, 2% (v/v). Thalidomide (Sigma, T144) was dissolved in DMSO at 1000× stock solution and used at a final concentration of 10 μg/ml. All-trans-Retinoic acid (Sigma, R2625) was dissolved in DMSO at 100,000× stock solution and used at a final concentration of 1 μM. Lithium chloride (J.T. Baker, NJ, USA, 2370) was dissolved in DDW and used at a final concentration of 1 mM. Caffeine (Sigma, C0750) was dissolved in DDW and used at a final concentration of 50 mg/ml.

Microarray data analysis: Following seven days in culture, embryoid bodies were harvested and RNA was extracted using RBC Bioscience (Taipei, Taiwan) total RNA extraction minikit (YRB50) according to the manufacturer's protocol. Hybridization to GeneChip Human Gene 1.0 ST expression arrays, washing and scanning were performed according to the manufacturer's protocol (Affymetrix). Arrays were analyzed using RMA probeset condensation algorithm (Expression Console, Affymetrix). Controls, RA, 0.5% ethanol, and lithium treatments were performed in triplicate. Thalidomide was tested twice and caffeine once. 1.5% and 2% ethanol were each performed once and analyzed together. All compounds were tested on H9 HESCs with the exception of RA that was tested also on HiPSCs. Adult tissue data [20] was obtained from Gene Expression Omnibus (GEO) accession GSE9819. Tissue specific genes were identified by comparing the expression of each of the five most relevant tissues to the mean expression of all other tissues (testis, brain, heart, spleen, skeletal muscle, kidney, liver, and breast). The top 200 genes by fold change for every tissue were regarded to be tissue specific genes.

Genes were considered differentially expressed when changed over two-fold. To determine significance, upregulated and downregulated genes were classified according to the aforementioned tissue specific gene lists. Significance was calculated separately for each test using a Chi-Square independence test and corrected for multiple testing (Bonferroni). Chi-Square tests were performed using the UCLA Statistics Online Computational Resource (SOCR) (http://www.socr.ucla.edu/). Functional classification and significance were performed using the DAVID online functional annotation tool (worldwidewebdotdaviddotabccdotncifcrfdotgov/) using default settings, with a minimum p-value of 0.0001. General annotations with over 2000 members were removed from the analysis.

Immunofluorescent labeling: EBs were treated for seven days with either 1.5% ethanol or 1 μM all-trans-retinoic acid (see Drug Treatment section). EBs were let to settle and perfused with 10% sucrose-PBS solution for 30 minutes at 4° C., followed by an additional step in 30% sucrose-PBS solution for 1 hr at 4° C., with gentle shaking. EBs were then frozen in Tissue-Tek OCT solution (Sakura Finetek, USA) and cut into 9 μm sections. Samples were fixed following sectioning with PBS buffered 4% formaldehyde solution for 3 minutes. Blocking was performed with PBS, 2% BSA, 0.1% Triton x-100 solution for 1 hour at room temperature. Sections were incubated overnight at 4° C. with the following primary antibodies; AFP at 1:50 dilution (SC-8399, Santa-Cruz); HOXA1 at 1:50 dilution (SC-17146, Santa-Cruz); NCAM-1 at 1:150 dilution (AF2408, R&D Systems); SOX17 at 1:400 dilution (AF1924, R&D Systems). The sections were then incubated for 1 hour with the appropriate secondary antibody (Cy-3, Jackson ImmunoResearch) at room temperature. Finally, sections were counterstained with Hoechst (B2883, Sigma) for 10 minutes at room temperature.

Example 1

Treatment with Human Teratogens Leads to Major Global Gene Expression Changes in Human Embryoid Bodies In this example, developing EBs were treated for seven days with various teratogens at concentrations corresponding to documented human serum levels [8,21]. Caffeine as a negative control was used at a concentration shown to induce malformations in mice [17]. Following treatment, gene expression was analyzed using DNA microarrays. Expression results were analyzed relative to their respective untreated controls and genes whose expression was significantly changed (over two-fold) were counted. Lithium, caffeine and 0.5% ethanol produced little or no effect. Higher doses of ethanol (1.5% and 2%), RA and thalidomide had more dramatic effects with several hundred probesets changing in their levels of expression (FIG. 1A). It will be appreciated that in the case of low dose of ethanol, technical difficulties were experienced and the present inventors believe that the high evaporation rate of ethanol may have effected the results.

The list of genes that were differentially expressed with ethanol, RA or thalidomide are provided in Table 2, herein below.

TABLE 2

| Probe Set ID | Gene Symbol | mRNA Accession GENSCAN | SEQ ID NO: |
|---|---|---|---|
| 7970392 | — | 00000042413 | 2434 |
| 8165684 | — | NC_001807 | 119 |
| 8165672 | — | NC_001807 | 119 |
| 8082673 | ACPP | NM_001099 | 1620 |
| 7979241 | BMP4 | NM_001202 | 1265 |
| 8160163 | CER1 | NM_005454 | 723 |
| 8128001 | CGA | NM_000735 | 60 |
| 8057620 | COL5A2 | NM_000393 | 796 |
| 8122365 | GPR126 | NM_020455 | 1480 |
| 7995895 | HERPUD1 | NM_014685 | 591 |
| 8016438 | HOXB2 | NM_002145 | 766 |
| 7959102 | HSPB8 | NM_014365 | 333 |
| 8105220 | ISL1 | NM_002202 | 943 |
| 8015349 | KRT19 | NM_002276 | 1073 |
| 7955613 | KRT7 | NM_005556 | 666 |
| 7971461 | LCP1 | NM_002298 | 1599 |
| 8042356 | MEIS1 | NM_002398 | 413 |
| 8110084 | MSX2 | NM_002449 | 764 |
| 7918936 | VTCN1 | NM_024626 | 863 |
| 8167560 | GAGE13 | NM_001098412 | 1136 |
| 7979357 | OTX2 | NM_021728 | 213 |
| 8161444 | — | ENST00000363455 | 2351 |
| 8043502 | — | ENST00000385959 | 2477 |
| 8100758 | — | ENST00000381100 | 2500 |
| 8165694 | — | NC_001807 | 119 |
| 7957608 | — | hsa-mir-492//hsa-mir-492 | 2428 |
| 8100310 | — | GENSCAN00000027548 | 2499 |
| 8156358 | — | ENST00000388661 | 2529 |
| 8045287 | — | ENST00000385614 | 2478 |
| 8045804 | — | ENST00000385501 | 2480 |

TABLE 2-continued

| Probe Set ID | Gene Symbol | mRNA Accession GENSCAN | SEQ ID NO: |
|---|---|---|---|
| 7951859 | APOA4 | NM_000482 | 696 |
| 7949410 | MALAT1 | AF001542 | 10 |
| 7963869 | PHC1 | NM_004426 | 637 |
| 7982084 | SNRPN//SNORD115-11 | NR_003303 | 1049 |
| 8044353 | ACOXL | NM_001105516 | 1772 |
| 7987315 | ACTC1 | NM_005159 | 928 |
| 8069676 | ADAMTS1 | NM_006988 | 505 |
| 8052882 | ADD2 | NM_017488 | 2126 |
| 8095646 | AFP | NM_001134 | 17 |
| 8174576 | AMOT | NM_133265 | 643 |
| 8095986 | ANXA3 | NM_005139 | 854 |
| 7905283 | ANXA9 | NM_003568 | 1120 |
| 8077192 | APOA4 | NM_000482 | 696 |
| 8029536 | APOC1 | NM_001645 | 516 |
| 8019964 | ARHGAP28 | NM_001010000 | 2203 |
| 7917850 | ARHGAP29 | NM_004815 | 1095 |
| 7927732 | ARID5B | NM_032199 | 2114 |
| 8059854 | ARL4C | NM_005737 | 345 |
| 8094911 | ATP10D | NM_020453 | 1830 |
| 7965359 | ATP2B1 | NM_001001323 | 470 |
| 7926875 | BAMBI | NM_012342 | 636 |
| 7928695 | C10orf58 | NM_032333 | 1145 |
| 7971590 | CAB39L | NM_030925 | 1007 |
| 8140579 | CACNA2D1 | NM_000722 | 540 |
| 8174527 | CAPN6 | NM_014289 | 2008 |
| 8107005 | CAST | NM_001750 | 881 |
| 8111271 | CDH9 | NM_016279 | 798 |
| 8149927 | CLU | NM_001831 | 403 |
| 8016646 | COL1A1 | NM_000088 | 896 |
| 8046922 | COL3A1 | NM_000090 | 888 |
| 8098204 | CPE | NM_001873 | 1325 |
| 7909164 | CTSE | NM_001910 | 2233 |
| 7990333 | CYP11A1 | NM_000781 | 1189 |
| 7988767 | CYP19A1 | NM_031226 | 1485 |
| 8111772 | DAB2 | NM_001343 | 1135 |
| 7968872 | DNAJC15 | NM_013238 | 657 |
| 7972487 | DOCK9 | NM_015296 | 1550 |
| 8116780 | DSP | NM_004415 | 590 |
| 7972713 | EFNB2 | NM_004093 | 2253 |

TABLE 2-continued

| Probe Set ID | Gene Symbol | mRNA Accession GENSCAN | SEQ ID NO: |
|---|---|---|---|
| 8096875 | ENPEP | NM_001977 | 1075 |
| 8041781 | EPAS1 | NM_001430 | 2001 |
| 8022118 | EPB41L3 | NM_012307 | 273 |
| 8059279 | EPHA4 | NM_004438 | 420 |
| 8128284 | EPHA7 | NM_004440 | 1650 |
| 8151310 | EYA1 | NM_000503 | 1400 |
| 8053654 | FABP1 | NM_001443 | 2299 |
| 8121784 | FABP7 | NM_001446 | 320 |
| 8146533 | FAM110B | NM_147189 | 748 |
| 7969192 | FAM124A | BC051771 | 247 |
| 8113800 | FBN2 | NM_001999 | 652 |
| 8103311 | FGA | NM_000508 | 686 |
| 8160168 | FREM1 | NM_144966 | 2087 |
| 7968678 | FREM2 | NM_207361 | 1020 |
| 8057506 | FRZB | NM_001463 | 2086 |
| 7950671 | GAB2 | NM_080491 | 2016 |
| 8109926 | GABRP | NM_014211 | 1606 |
| 7926105 | GATA3 | NM_001002295 | 494 |
| 8116418 | GFPT2 | NM_005110 | 1103 |
| 8175217 | GPC4 | NM_001448 | 156 |
| 7987439 | GPR176 | NM_007223 | 39 |
| 7996081 | GPR56 | NM_201524 | 1866 |
| 8106827 | GPR98 | NM_032119 | 927 |
| 8040190 | GRHL1 | NM_014552 | 335 |
| 8096440 | GRID2 | NM_001510 | 1268 |
| 8097957 | GUCY1A3 | NM_000856 | 1583 |
| 7945680 | H19 | NR_002196 | 583 |
| 8115391 | HAND1 | NM_004821 | 1613 |
| 8151457 | HEY1 | NM_012258 | 871 |
| 8103769 | HPGD | NM_000860 | 1870 |
| 8139488 | IGFBP3 | NM_001013398 | 619 |
| 8024728 | ITGB1BP3 | NM_170678 | 1182 |
| 8020384 | KIAA1772 | AK293321 | 1566 |
| 7922268 | KIFAP3 | NM_014970 | 2295 |
| 8015133 | KRT23 | NM_015515 | 225 |
| 7963567 | KRT8 | NM_002273 | 1611 |
| 7929373 | LGI1 | NM_005097 | 1397 |
| 8168517 | LPAR4 | NM_005296 | 1838 |

TABLE 2-continued

| Probe Set ID | Gene Symbol | mRNA Accession GENSCAN | SEQ ID NO: |
|---|---|---|---|
| 8097920 | LRAT | NM_004744 | 443 |
| 8088642 | LRIG1 | NM_015541 | 545 |
| 8056611 | LRP2 | NM_004525 | 1056 |
| 8064894 | LRRN4 | NM_152611 | 1459 |
| 8045664 | LYPD6B | NM_177964 | 359 |
| 8129254 | MAN1A1 | NM_005907 | 197 |
| 7969677 | MBNL2 | NM_144778 | 445 |
| 8107722 | MEGF10 | NM_032446 | 1403 |
| 7987385 | MEIS2 | NM_172316 | 215 |
| 7947156 | MUC15 | NM_001135091 | 1654 |
| 8171172 | MXRA5 | NM_015419 | 1647 |
| 7978644 | NFKBIA | NM_020529 | 1364 |
| 8069553 | NRIP1 | NM_003489 | 1718 |
| 7932985 | NRP1 | NM_003873 | 1404 |
| 7957458 | NTS | NM_006183 | 2252 |
| 7925492 | OPN3 | NM_014322 | 700 |
| 8103399 | PDGFC | NM_016205 | 2202 |
| 7953812 | PHC1 | NM_004426 | 637 |
| 8172471 | PIM2 | NM_006875 | 1692 |
| 7962212 | PKP2 | NM_004572 | 1151 |
| 7913216 | PLA2G2A | NM_000300 | 1923 |
| 8112202 | PLK2 | NM_006622 | 817 |
| 7923991 | PLXNA2 | NM_025179 | 926 |
| 8151240 | PRDM14 | NM_024504 | 385 |
| 7994131 | PRKCB | NM_002738 | 1617 |
| 7974835 | PRKCH | NM_006255 | 463 |
| 7978407 | PRKD1 | NM_002742 | 954 |
| 8143144 | PTN | NM_002825 | 397 |
| 7906919 | RGS4 | NM_001102445 | 1324 |
| 7921916 | RGS5 | NM_003617 | 2091 |
| 7933821 | RHOBTB1 | NM_014836 | 1753 |
| 8121916 | RSPO3 | NM_032784 | 712 |
| 7920297 | S100A14 | NM_020672 | 56 |
| 7920291 | S100A16 | NM_080388 | 118 |
| 8118890 | SCUBE3 | NM_152753 | 256 |
| 8140534 | SEMA3C | NM_006379 | 270 |
| 7983527 | SEMA6D | NM_153618 | 189 |
| 8123609 | SERPINB9 | NM_004155 | 1854 |
| 8059376 | SERPINE2 | NM_001136529 | 1715 |

TABLE 2-continued

| Probe Set ID | Gene Symbol | mRNA Accession GENSCAN | SEQ ID NO: |
|---|---|---|---|
| 8138689 | SKAP2 | NM_003930 | 338 |
| 7918426 | SLC16A4 | NM_004696 | 2265 |
| 8090823 | SLCO2A1 | NM_005630 | 1456 |
| 8121794 | SMPDL3A | NM_006714 | 1584 |
| 8165866 | STS | NM_000351 | 1193 |
| 8045889 | TANC1 | NM_033394 | 1875 |
| 8102912 | TBC1D9 | NM_015130 | 1097 |
| 7966690 | TBX3 | NM_016569 | 459 |
| 8079422 | TDGF1 | NM_003212 | 2073 |
| 7938035 | TRIM22 | NM_006074 | 2229 |
| 8068522 | TTC3 | NM_003316 | 486 |
| 8128111 | UBE2J1 | NM_016021 | 325 |
| 8100768 | UGT2B11 | NM_001073 | 23 |
| 8101788 | UNC5C | NM_003728 | 2172 |
| 7997336 | VAT1L | NM_020927 | 190 |
| 8170179 | VGLL1 | NM_016267 | 1936 |
| 8157193 | ZNF483 | NM_133464 | 1511 |
| 7998921 | ZSCAN10 | NM_032805 | 90 |
| 7936798 | CUZD1 | NM_022034 | 2286 |
| 8006906 | ERBB2 | NM_001005862 | 546 |
| 8142580 | FEZF1 | NM_001024613 | 1907 |
| 8150428 | SFRP1 | NM_003012 | 1958 |
| 7969830 | ZIC2 | NM_007129 | 2292 |
| 8112070 | — | ENST00000364499 | 2507 |
| 8151629 | REXO1L1 | AF495523 | 209 |
| 8065412 | CST1 | NM_001898 | 129 |
| 8097910 | FGB | NM_005141 | 2113 |
| 8165667 | — | NC_001807 | 119 |
| 8165682 | — | NC_001807 | 119 |
| 8165696 | — | NC_001807 | 119 |
| 8165705 | — | NC_001807 | 119 |
| 8019649 | — | ENST00000384483 | 2357 |
| 7969574 | — | hsa-mir-622//hsa-mir-622 | 2433 |
| 8102406 | — | hsa-mir-302b//hsa-mir-302b | 2503 |
| 8102404 | — | hsa-mir-302a//hsa-mir-302a | 2502 |
| 7970426 | — | ENST00000410436 | 2435 |
| 8137668 | — | ENST00000410382 | 2382 |
| 8017702 | — | ENST00000410341 | 2467 |

TABLE 2-continued

| Probe Set ID | Gene Symbol | mRNA Accession GENSCAN | SEQ ID NO: |
|---|---|---|---|
| 8154725 | — | ENST00000390176 | 2405 |
| 7982290 | — | ENST00000387426 | 2443 |
| 8013521 | — | ENST00000387241 | 2465 |
| 7973867 | — | ENST00000386811 | 2438 |
| 8081878 | — | ENST00000386447 | 2490 |
| 8043375 | — | ENST00000386014 | 2469 |
| 8097955 | — | ENST00000385964 | 2497 |
| 8045533 | — | ENST00000385551 | 2479 |
| 8008170 | — | ENST00000384616 | 2461 |
| 8007990 | — | ENST00000384483 | 2357 |
| 8144717 | — | ENST00000384269 | 2378 |
| 7928489 | — | ENST00000384029 | 2344 |
| 8116952 | — | ENST00000383975 | 2402 |
| 8145622 | — | ENST00000365541 | 2361 |
| 7966343 | — | ENST00000365465 | 2374 |
| 7929256 | — | ENST00000365427 | 2369 |
| 8081546 | — | ENST00000364556 | 2373 |
| 8122198 | — | ENST00000364439 | 2367 |
| 8135943 | — | ENST00000364171 | 2327 |
| 8161737 | — | ENST00000364052 | 2330 |
| 7984620 | — | ENST00000364003 | 2381 |
| 7915592 | — | ENST00000363299 | 2379 |
| 8105577 | — | ENST00000362409 | 2371 |
| 8155359 | — | ENST00000333554 | 2337 |
| 8047763 | — | AK024680 | 57 |
| 8095005 | — | AF085847 | 14 |
| 8054054 | ANKRD36B | NM_025190 | 1956 |
| 7951865 | APOA1 | NM_000039 | 25 |
| 8177460 | C20orf69 | BC118988 | 909 |
| 7904421 | HSD3B1 | NM_000862 | 939 |
| 7953675 | NANOG | NM_024865 | 1208 |
| 8179719 | POU5F1 | NM_002701 | 965 |
| 7919576 | RNU1A | NR_004421 | 1304 |
| 7981945 | SNRPN | BC043194 | 216 |
| 7982050 | SNRPN//SNORD115-11 | NR_003303 | 1049 |
| 8102789 | TERF1 | NM_017489 | 1496 |
| 8096675 | TET2 | NM_001127208 | 2297 |
| 8136807 | TRY6 | NR_001296 | 1932 |
| 8114050 | ספטמבר-08 | NM_015146 | 1167 |

TABLE 2-continued

| Probe Set ID | Gene Symbol | mRNA Accession GENSCAN | SEQ ID NO: |
|---|---|---|---|
| 7960947 | A2M | NM_000014 | 661 |
| 8142554 | AASS | NM_005763 | 1642 |
| 8101675 | ABCG2 | NM_004827 | 626 |
| 7930498 | ACSL5 | NM_016234 | 408 |
| 8002941 | ADAMTS18 | NM_199355 | 1165 |
| 8088560 | ADAMTS9 | NM_182920 | 288 |
| 7905233 | ADAMTSL4 | NM_019032 | 749 |
| 7930482 | ADRA2A | NM_000681 | 1564 |
| 7948667 | AHNAK | NM_001620 | 612 |
| 8084648 | AHSG | NM_001622 | 1242 |
| 7962183 | AK3L1 | NM_001005353 | 2134 |
| 8001410 | AKTIP | NM_001012398 | 611 |
| 8161755 | ALDH1A1 | NM_000689 | 2311 |
| 8096959 | ANK2 | NM_001148 | 1461 |
| 8138370 | ANKMY2 | NM_020319 | 2119 |
| 7934979 | ANKRD1 | NM_014391 | 339 |
| 8121095 | ANKRD6 | NM_014942 | 1214 |
| 8101260 | ANTXR2 | NM_058172 | 1867 |
| 8155849 | ANXA1 | NM_000700 | 18 |
| 7948167 | APLNR | NM_005161 | 1933 |
| 8077185 | APOA1 | NM_000039 | 25 |
| 7921834 | APOA2 | NM_001643 | 19 |
| 8050619 | APOB | NM_000384 | 872 |
| 8097717 | ARHGAP10 | NM_024605 | 504 |
| 8129458 | ARHGAP18 | NM_033515 | 354 |
| 8096160 | ARHGAP24 | NM_001025616 | 904 |
| 8158671 | ASS1 | NM_000050 | 925 |
| 8024712 | ATCAY | NM_033064 | 1482 |
| 8037079 | ATP1A3 | NM_152296 | 478 |
| 8004545 | ATP1B2 | NM_001678 | 482 |
| 7908940 | ATP2B4 | NM_001001396 | 471 |
| 8023497 | ATP8B1 | NM_005603 | 2071 |
| 7988644 | ATP8B4 | NM_024837 | 487 |
| 8046078 | B3GALT1 | NM_020981 | 2189 |
| 8084206 | B3GNT5 | NM_032047 | 825 |
| 7976560 | BDKRB2 | NM_000623 | 1361 |
| 8174201 | BEX1 | NM_018476 | 682 |
| 7987454 | BMF | NM_001003940 | 511 |

TABLE 2-continued

| Probe Set ID | Gene Symbol | mRNA Accession GENSCAN | SEQ ID NO: |
|---|---|---|---|
| 7926609 | BMI1 | NM_005180 | 2278 |
| 8060850 | BMP2 | NM_001200 | 741 |
| 8116818 | BMP6 | NM_001718 | 1082 |
| 7991080 | BNC1 | NM_001717 | 1264 |
| 7905308 | BNIPL | NM_138278 | 1897 |
| 8131583 | BZW2 | NM_014038 | 1899 |
| 7967107 | C12orf27 | NR_024345 | 1713 |
| 7975702 | C14orf115 | NM_018228 | 1198 |
| 7982535 | C15orf41 | NM_032499 | 1539 |
| 7907404 | C1orf9 | NM_014283 | 1391 |
| 8070629 | C21orf105 | BC005107 | 83 |
| 8056201 | C2orf12 | BC065192 | 372 |
| 8103415 | C4orf18 | NM_001128424 | 1517 |
| 8094550 | C4orf19 | NM_001104629 | 1273 |
| 8123678 | C6orf145 | NM_183373 | 1488 |
| 8128837 | C6orf186 | NM_001123364 | 1405 |
| 8146115 | C8orf4 | NM_020130 | 990 |
| 8155747 | C9orf135 | NM_001010940 | 584 |
| 8147132 | CA2 | NM_000067 | 1294 |
| 8147123 | CA3 | NM_005181 | 1674 |
| 8166184 | CA5B | NM_007220 | 851 |
| 7901993 | CACHD1 | NM_020925 | 897 |
| 8031076 | CACNG7 | NM_031896 | 2224 |
| 8102415 | CAMK2D | NM_172127 | 1726 |
| 8087530 | CAMKV | NM_024046 | 754 |
| 8089261 | CBLB | NM_170662 | 542 |
| 8089544 | CCDC80 | NM_199511 | 377 |
| 7942123 | CCND1 | NM_053056 | 732 |
| 8027837 | CD22 | NM_001771 | 2130 |
| 8154233 | CD274 | NM_014143 | 2074 |
| 8176360 | CD99 | NM_002414 | 295 |
| 8138489 | CDCA7L | NM_018719 | 1885 |
| 8111255 | CDH10 | NM_006727 | 2136 |
| 7996264 | CDH5 | NM_001795 | 1336 |
| 8104663 | CDH6 | NM_004932 | 99 |
| 8140955 | CDK6 | NM_001259 | 1849 |
| 7982868 | CHAC1 | NM_024111 | 1771 |
| 8132013 | CHN2 | NM_004067 | 803 |
| 8129937 | CITED2 | NM_006079 | 514 |

TABLE 2-continued

| Probe Set ID | Gene Symbol | mRNA Accession GENSCAN | SEQ ID NO: |
|---|---|---|---|
| 7969640 | CLDN10 | NM_182848 | 1902 |
| 7967255 | CLIP1 | NM_002956 | 331 |
| 8056343 | COBLL1 | NM_014900 | 628 |
| 7973797 | COCH | NM_001135058 | 1653 |
| 8082597 | COL6A6 | NM_001102608 | 1247 |
| 7985159 | CRABP1 | NM_004378 | 1527 |
| 7921099 | CRABP2 | NM_001878 | 2231 |
| 8146967 | CRISPLD1 | NM_031461 | 2174 |
| 8099172 | CRMP1 | NM_001313 | 623 |
| 8176306 | CSF2RA | NM_006140 | 1912 |
| 8156228 | CTSL1 | NM_001912 | 1679 |
| 8162652 | CTSL2 | NM_001333 | 2266 |
| 8142497 | CTTNBP2 | NM_033427 | 814 |
| 8114249 | CXCL14 | NM_004887 | 1666 |
| 8102135 | CXXC4 | NM_025212 | 81 |
| 7929322 | CYP26A1 | NM_000783 | 1494 |
| 8121685 | DCBLD1 | NM_173674 | 218 |
| 7970954 | DCLK1 | NM_004734 | 2192 |
| 7965410 | DCN | NM_001920 | 460 |
| 7912537 | DHRS3 | NM_004753 | 639 |
| 7976858 | DIO3 | NM_001362 | 1133 |
| 7947512 | DKFZP586H2123 | NM_015430 | 502 |
| 7927631 | DKK1 | NM_012242 | 607 |
| 8016609 | DLX3 | NM_005220 | 341 |
| 8141140 | DLX5 | NM_005221 | 761 |
| 7932512 | DNAJC1 | NM_022365 | 884 |
| 8061746 | DNMT3B | NM_006892 | 234 |
| 8001564 | DOK4 | NM_018110 | 1534 |
| 8056222 | DPP4 | NM_001935 | 449 |
| 8089448 | DPPA4 | NM_018189 | 1111 |
| 8114920 | DPYSL3 | NM_001387 | 424 |
| 8040725 | DPYSL5 | NM_020134 | 1442 |
| 8022711 | DSC2 | NM_024422 | 1484 |
| 7965335 | DUSP6 | NM_001946 | 406 |
| 8052355 | EFEMP1 | NM_004105 | 782 |
| 7905929 | EFNA1 | NM_004428 | 281 |
| 7982620 | EIF2AK4 | NM_001013703 | 648 |
| 7908793 | ELF3 | NM_001114309 | 1343 |

TABLE 2-continued

| Probe Set ID | Gene Symbol | mRNA Accession GENSCAN | SEQ ID NO: |
|---|---|---|---|
| 7999387 | EMP2 | NM_001424 | 1626 |
| 8112615 | ENC1 | NM_003633 | 1501 |
| 8149793 | ENTPD4 | NM_004901 | 1529 |
| 8085946 | EOMES | NM_005442 | 174 |
| 8084524 | EPHB3 | NM_004443 | 286 |
| 7961524 | ERP27 | NM_152321 | 1727 |
| 7912157 | ERRFI1 | NM_018948 | 1701 |
| 8139840 | ERV3 | NM_001007253 | 2131 |
| 8140909 | ERVWE1 | NM_014590 | 475 |
| 8138289 | ETV1 | NM_004956 | 1934 |
| 8015806 | ETV4 | NM_001079675 | 1008 |
| 7951545 | EXPH5 | NM_015065 | 1820 |
| 8147019 | FAM164A | AF151820 | 34 |
| 8127778 | FAM46A | NM_017633 | 987 |
| 7914015 | FAM46B | NM_052943 | 1695 |
| 8050427 | FAM49A | NM_030797 | 2048 |
| 8120335 | FAM83B | NM_001010872 | 604 |
| 7952490 | FEZ1 | NM_005103 | 2190 |
| 8097256 | FGF2 | NM_002006 | 1197 |
| 8103326 | FGG | NM_021870 | 687 |
| 7963328 | FIGNL2 | NM_001013690 | 2247 |
| 8030964 | FLJ45949 | AK127846 | 310 |
| 7976073 | FLRT2 | NM_013231 | 618 |
| 8065071 | FLRT3 | NM_198391 | 2161 |
| 7970763 | FLT1 | NM_002019 | 1901 |
| 8058765 | FN1 | NM_212482 | 455 |
| 7975779 | FOS | NM_005252 | 1942 |
| 8088745 | FRMD4B | NM_015123 | 1173 |
| 7917954 | FRRS1 | NM_001013660 | 1125 |
| 8105302 | FST | NM_006350 | 2320 |
| 7986092 | FURIN | NM_002569 | 135 |
| 8115651 | GABRB2 | NM_021911 | 1037 |
| 7986822 | GABRB3 | NM_000814 | 2157 |
| 7942064 | GAL | NM_015973 | 790 |
| 8090469 | GATA2 | NM_032638 | 1864 |
| 8127130 | GCM1 | NM_003643 | 1749 |
| 8155930 | GCNT1 | NM_001490 | 1131 |
| 7960828 | GDF3 | NM_020634 | 55 |
| 8151906 | GDF6 | NM_001001557 | 1449 |

TABLE 2-continued

| Probe Set ID | Gene Symbol | mRNA Accession GENSCAN | SEQ ID NO: |
|---|---|---|---|
| 8168163 | GDPD2 | NM_017711 | 2038 |
| 8151032 | GGH | NM_003878 | 1746 |
| 8086028 | GLB1 | NM_000404 | 1011 |
| 7945296 | GLB1L3 | NM_001080407 | 1319 |
| 8139212 | GLI3 | NM_000168 | 1601 |
| 8080964 | GLT8D4 | BC127733 | 994 |
| 8091954 | GOLIM4 | NM_014498 | 1220 |
| 7969613 | GPC6 | NM_005708 | 1816 |
| 8171359 | GPM6B | NM_001001995 | 488 |
| 7916862 | GPR177 | NM_024911 | 2160 |
| 7954065 | GPRC5A | NM_003979 | 644 |
| 7999909 | GPRC5B | NM_016235 | 46 |
| 7979658 | GPX2 | NM_002083 | 274 |
| 8081758 | GRAMD1C | NM_017577 | 1441 |
| 8107673 | GRAMD3 | NM_023927 | 1890 |
| 8147697 | GRHL2 | NM_024915 | 1390 |
| 7943530 | GRIA4 | NM_000829 | 1317 |
| 8166202 | GRPR | NM_005314 | 608 |
| 8127065 | GSTA2 | NM_000846 | 1742 |
| 7930304 | GSTO1 | NM_004832 | 2151 |
| 8114225 | H2AFY | NM_004893 | 138 |
| 7928107 | H2AFY2 | NM_018649 | 849 |
| 8112971 | HAPLN1 | NM_001884 | 1535 |
| 8152617 | HAS2 | NM_005328 | 1376 |
| 8123929 | HERV-FRD | NM_207582 | 1970 |
| 8146285 | HGSNAT | NM_152419 | 1176 |
| 8152938 | HHLA1 | AF110315 | 15 |
| 8124492 | HIST1H2BK | NM_080593 | 2167 |
| 7919055 | HMGCS2 | NM_005518 | 1983 |
| 8138708 | HOXA1 | NM_005522 | 767 |
| 8138718 | HOXA2 | NM_006735 | 328 |
| 8138721 | HOXA3 | NM_153631 | 757 |
| 8138735 | HOXA5 | NM_019102 | 2288 |
| 8016433 | HOXB1 | NM_002144 | 758 |
| 8016444 | HOXB3 | NM_002146 | 765 |
| 8016457 | HOXB5 | NM_002147 | 775 |
| 8016463 | HOXB6 | NM_018952 | 778 |
| 7955887 | HOXC5 | NM_018953 | 198 |

TABLE 2-continued

| Probe Set ID | Gene Symbol | mRNA Accession GENSCAN | SEQ ID NO: |
|---|---|---|---|
| 7946167 | HPX | NM_000613 | 1893 |
| 8101648 | HSD17B11 | NM_016245 | 1107 |
| 7913566 | HTR1D | NM_000864 | 1432 |
| 8040103 | ID2 | NM_002166 | 290 |
| 8146092 | IDO1 | NM_002164 | 2279 |
| 7906400 | IFI16 | NM_005531 | 920 |
| 8026971 | IFI30 | NM_006332 | 243 |
| 7914127 | IFI6 | NM_002038 | 842 |
| 7989770 | IGDCC3 | NM_004884 | 1093 |
| 7937772 | IGF2 | AK074614 | 183 |
| 8058670 | IKZF2 | NM_016260 | 1010 |
| 8112139 | IL6ST | NM_002184 | 2148 |
| 8106354 | IQGAP2 | NM_006633 | 961 |
| 7907104 | IQWD1 | NM_018442 | 2213 |
| 8001449 | IRX3 | NM_024336 | 1887 |
| 8046380 | ITGA6 | NM_000210 | 1016 |
| 8056184 | ITGB6 | NM_000888 | 53 |
| 8116998 | JARID2 | NM_004973 | 69 |
| 8171248 | KAL1 | NM_000216 | 1017 |
| 8078227 | KAT2B | NM_003884 | 1226 |
| 8009502 | KCNJ2 | NM_000891 | 166 |
| 7951535 | KDELC2 | NM_153705 | 1188 |
| 8100393 | KDR | NM_002253 | 1598 |
| 8143534 | KEL | NM_000420 | 114 |
| 7988581 | KIAA0256 | BC033001 | 297 |
| 7988970 | KIAA1370 | NM_019600 | 1213 |
| 8045637 | KIF5C | NM_004522 | 30 |
| 7965322 | KITLG | NM_000899 | 2141 |
| 8168622 | KLHL4 | NM_019117 | 1751 |
| 8099524 | LDB2 | NM_001130834 | 1600 |
| 7971838 | LECT1 | NM_007015 | 595 |
| 8102232 | LEF1 | NM_016269 | 1984 |
| 7957140 | LGR5 | NM_003667 | 194 |
| 7966631 | LHX5 | NM_022363 | 251 |
| 8111677 | LIFR | NM_002310 | 1479 |
| 7963187 | LIMA1 | NM_001113546 | 1327 |
| 8021169 | LIPG | NM_006033 | 624 |
| 8113278 | LIX1 | NM_153234 | 1351 |
| 8100362 | LNX1 | NM_001126328 | 1424 |

TABLE 2-continued

| Probe Set ID | Gene Symbol | mRNA Accession GENSCAN | SEQ ID NO: |
|---|---|---|---|
| 8028742 | LOC148003 | XM_086001 | 1367 |
| 8047272 | LOC26010 | NM_015535 | 1216 |
| 7977270 | LOC388022 | AK131040 | 304 |
| 8161460 | LOC389725//AL953854.2//CNTNAP3 | ENST00000377514 | 2532 |
| 7993296 | LOC440338 | AK299610 | 1573 |
| 8168873 | LOC653354 | ENST00000372828 | 2414 |
| 8113709 | LOX | NM_002317 | 2103 |
| 7917276 | LPAR3 | NM_012152 | 1408 |
| 7965403 | LUM | NM_002345 | 609 |
| 8045674 | LYPD6 | NM_194317 | 2198 |
| 7904106 | MAGI3 | NM_152900 | 1225 |
| 7904340 | MAN1A2 | NM_006699 | 447 |
| 8121144 | MANEA | NM_024641 | 390 |
| 7961365 | MANSC1 | NM_018050 | 260 |
| 8166925 | MAOA | NM_000240 | 282 |
| 8047926 | MAP2 | NM_002374 | 788 |
| 8175177 | MBNL3 | NM_018388 | 2027 |
| 8044391 | MERTK | NM_006343 | 660 |
| 8135601 | MET | NM_001127500 | 1466 |
| 7955441 | METTL7A | NM_014033 | 794 |
| 8118116 | MICB | NM_005931 | 1358 |
| 7910134 | MIXL1 | NM_031944 | 86 |
| 8062123 | MMP24 | NM_006690 | 704 |
| 8160088 | MPDZ | NM_003829 | 1154 |
| 7947274 | MPPED2 | NM_001584 | 1857 |
| 7947093 | MRGPRX1 | NM_147199 | 1041 |
| 8001531 | MT1G | NM_005950 | 62 |
| 8096580 | MTTP | NM_000253 | 1196 |
| 8122202 | MYB | NM_001130173 | 1562 |
| 8122860 | MYCT1 | NM_025107 | 1234 |
| 8023267 | MYO5B | NM_001080467 | 1924 |
| 7935058 | MYOF | NM_013451 | 1745 |
| 8083978 | NAALADL2 | NM_207015 | 1066 |
| 7987365 | NANOG | NM_024865 | 1208 |
| 8147244 | NECAB1 | NM_022351 | 1802 |
| 8123936 | NEDD9 | NM_006403 | 1747 |
| 7962455 | NELL2 | NM_006159 | 1840 |
| 8096635 | NFKB1 | NM_003998 | 1973 |

TABLE 2-continued

| Probe Set ID | Gene Symbol | mRNA Accession GENSCAN | SEQ ID NO: |
|---|---|---|---|
| 7934156 | NODAL | NM_018055 | 1828 |
| 8134463 | NPTX2 | NM_002523 | 1847 |
| 8002303 | NQO1 | NM_000903 | 688 |
| 7986329 | NR2F2 | NM_021005 | 1843 |
| 8169115 | NRK | NM_198465 | 1004 |
| 7938687 | NUCB2 | NM_005013 | 959 |
| 8055478 | NXPH2 | NM_007226 | 1810 |
| 8047161 | OBFC2A | NM_001031716 | 1721 |
| 7917433 | ODF2L | NM_020729 | 2115 |
| 7950701 | ODZ4 | NM_001098816 | 1372 |
| 7938225 | OLFML1 | NM_198474 | 2041 |
| 7982688 | PAK6 | NM_020168 | 1523 |
| 7981943 | PAR5 | NR_022008 | 1406 |
| 7938528 | PARVA | NM_018222 | 2246 |
| 8097449 | PCDH10 | NM_032961 | 97 |
| 7930454 | PDCD4 | NM_145341 | 2227 |
| 7954293 | PDE3A | NM_000921 | 683 |
| 8175860 | PDZD4 | NM_032512 | 446 |
| 7904843 | PDZK1 | NM_002614 | 2255 |
| 7897378 | PER3 | NM_016831 | 50 |
| 7980233 | PGF | NM_002632 | 2325 |
| 7932530 | PIP4K2A | NM_005028 | 1240 |
| 8006005 | PIPOX | NM_016518 | 602 |
| 8126784 | PLA2G7 | NM_005084 | 1478 |
| 7929388 | PLCE1 | NM_016341 | 984 |
| 7923635 | PLEKHA6 | NM_014935 | 327 |
| 8169061 | PLP1 | NM_000533 | 386 |
| 8021470 | PMAIP1 | NM_021127 | 1163 |
| 8012896 | PMP22 | NM_000304 | 191 |
| 8106820 | POLR3G | NM_006467 | 955 |
| 8178470 | POU5F1 | NM_002701 | 965 |
| 8148315 | POU5F1P1 | NR_002304 | 1859 |
| 8031999 | PPAP2C | NM_003712 | 238 |
| 7938231 | PPFIBP2 | NM_003621 | 1393 |
| 8114900 | PPP2R2B | NM_004576 | 269 |
| 8102468 | PRSS12 | NM_003619 | 2147 |
| 7989073 | PRTG | NM_173814 | 1860 |
| 8023043 | PSTPIP2 | NM_024430 | 1328 |

TABLE 2-continued

| Probe Set ID | Gene Symbol | mRNA Accession GENSCAN | SEQ ID NO: |
|---|---|---|---|
| 8161632 | PTAR1 | NM_001099666 | 1204 |
| 8019988 | PTPRM | NM_001105244 | 1277 |
| 8135774 | PTPRZ1 | NM_002851 | 807 |
| 7921773 | PVRL4 | NM_030916 | 1824 |
| 7906079 | RAB25 | NM_020387 | 981 |
| 8020110 | RAB31 | NM_006868 | 1386 |
| 8078286 | RARB | NM_000965 | 1607 |
| 7987405 | RASGRP1 | NM_005739 | 1521 |
| 8091078 | RBP1 | NM_002899 | 1605 |
| 7935116 | RBP4 | NM_006744 | 550 |
| 7989670 | RBPMS2 | NM_194272 | 317 |
| 8141950 | RELN | NM_005045 | 1850 |
| 8173503 | RGAG4 | NM_001024455 | 2101 |
| 8106986 | RHOBTB3 | NM_014899 | 945 |
| 7910387 | RHOU | NM_021205 | 2305 |
| 8061247 | RIN2 | NM_018993 | 318 |
| 8055688 | RND3 | NM_005168 | 575 |
| 8169174 | RNF128 | NM_024539 | 326 |
| 8018652 | RNF157 | NM_052916 | 1827 |
| 7901969 | ROR1 | NM_005012 | 1091 |
| 8171762 | RPS6KA3 | NM_004586 | 564 |
| 7920128 | S100A11 | NM_005620 | 35 |
| 8001387 | SALL1 | NM_002968 | 996 |
| 8066117 | SAMHD1 | NM_015474 | 2068 |
| 8085716 | SATB1 | NM_002971 | 2193 |
| 8108995 | SCGB3A2 | NM_054023 | 2055 |
| 8140668 | SEMA3A | NM_006080 | 864 |
| 8140686 | SEMA3D | NM_152754 | 392 |
| 7981068 | SERPINA1 | NM_001002236 | 1483 |
| 8071420 | SERPIND1 | NM_000185 | 710 |
| 7940028 | SERPING1 | NM_000062 | 711 |
| 8052669 | SERTAD2 | NM_014755 | 1652 |
| 8041582 | SGK493 | NM_138370 | 1670 |
| 8144880 | SH2D4A | NM_022071 | 2075 |
| 8094870 | SHISA3 | NM_001080505 | 1029 |
| 8143110 | SLC13A4 | NM_012450 | 267 |
| 8121515 | SLC16A10 | NM_018593 | 1800 |
| 8017843 | SLC16A6 | NM_004694 | 2076 |
| 8107798 | SLC27A6 | NM_001017372 | 629 |

TABLE 2-continued

| Probe Set ID | Gene Symbol | mRNA Accession GENSCAN | SEQ ID NO: |
|---|---|---|---|
| 8129666 | SLC2A12 | NM_145176 | 831 |
| 7988426 | SLC30A4 | NM_013309 | 526 |
| 8094441 | SLC34A2 | NM_006424 | 899 |
| 7956229 | SLC39A5 | NM_001135195 | 1658 |
| 8057677 | SLC40A1 | NM_014585 | 1426 |
| 8144786 | SLC7A2 | NM_003046 | 1967 |
| 7977786 | SLC7A7 | NM_003982 | 1417 |
| 8051762 | SLC8A1 | NM_021097 | 953 |
| 8006531 | SLFN5 | NM_144975 | 1118 |
| 7975390 | SMOC1 | NM_001034852 | 2302 |
| 8001748 | SNORA50 | NR_002980 | 809 |
| 7951036 | SNORD5 | NR_003033 | 839 |
| 7982092 | SNRPN//SNORD115-11 | NR_003303 | 1049 |
| 7982030 | SNRPN//SNORD115-12 | NR_003304 | 1054 |
| 7982046 | SNRPN//SNORD115-20 | NR_003312 | 1057 |
| 7982058 | SNRPN//SNORD115-26 | NR_003343 | 1050 |
| 7982090 | SNRPN//SNORD115-42 | NR_003357 | 1044 |
| 7982018 | SNRPN//SNORD115-6 | NR_003298 | 1058 |
| 7981949 | SNRPN//SNORD116-1 | NR_003316 | 1045 |
| 7981984 | SNRPN//SNORD116-18 | NR_003333 | 1083 |
| 7981960 | SNRPN//SNORD116-6 | NR_003321 | 1055 |
| 7918323 | SORT1 | NM_002959 | 2310 |
| 8084165 | SOX2 | NM_003106 | 2300 |
| 7961798 | SOX5 | NM_152989 | 245 |
| 8016382 | SP6 | NM_199262 | 399 |
| 8083071 | SPSB4 | NM_080862 | 122 |
| 8046726 | SSFA2 | NM_001130445 | 1565 |
| 8153021 | ST3GAL1 | NM_003033 | 1729 |
| 7929012 | STAMBPL1 | NM_020799 | 530 |
| 8149825 | STC1 | NM_003155 | 603 |
| 8163896 | STOM | NM_004099 | 330 |
| 8146863 | SULF1 | NM_001128205 | 1505 |
| 8163202 | SVEP1 | NM_153366 | 1162 |
| 7947147 | SVIP | NM_148893 | 1252 |
| 7917322 | SYDE2 | NM_032184 | 1166 |
| 8156321 | SYK | NM_003177 | 2077 |
| 8075616 | SYN3 | NM_003490 | 1683 |
| 7962226 | SYT10 | NM_198992 | 2197 |

TABLE 2-continued

| Probe Set ID | Gene Symbol | mRNA Accession GENSCAN | SEQ ID NO: |
|---|---|---|---|
| 8130703 | T | NM_003181 | 128 |
| 7916584 | TACSTD2 | NM_002353 | 1341 |
| 7944082 | TAGLN | NM_001001522 | 468 |
| 8169385 | TDGF3 | NR_002718 | 819 |
| 8146914 | TERF1 | NM_017489 | 1496 |
| 8135576 | TES | NM_015641 | 2294 |
| 8123864 | TFAP2A | NM_003220 | 879 |
| 8063536 | TFAP2C | NM_003222 | 353 |
| 8057599 | TFPI | NM_006287 | 860 |
| 8130867 | THBS2 | NM_003247 | 365 |
| 7899627 | TINAGL1 | NM_022164 | 1707 |
| 8091411 | TM4SF1 | NM_014220 | 625 |
| 7955063 | TMEM106C | NM_024056 | 1788 |
| 8103226 | TMEM154 | NM_152680 | 2200 |
| 7914592 | TMEM54 | NM_033504 | 293 |
| 7903162 | TMEM56 | NM_152487 | 1628 |
| 7983157 | TMEM62 | NM_024956 | 531 |
| 8004691 | TMEM88 | NM_203411 | 409 |
| 7944164 | TMPRSS4 | NM_019894 | 1119 |
| 8163637 | TNC | NM_002160 | 1209 |
| 8122265 | TNFAIP3 | NM_006290 | 210 |
| 7968015 | TNFRSF19 | NM_148957 | 2293 |
| 8163618 | TNFSF15 | NM_005118 | 2284 |
| 8001394 | TOX3 | NM_001080430 | 1881 |
| 8151890 | TP53INP1 | NM_033285 | 1678 |
| 8084766 | TP63 | NM_003722 | 1368 |
| 8121838 | TPD52L1 | NM_001003395 | 508 |
| 8117321 | TRIM38 | NM_006355 | 200 |
| 8143499 | TRPV6 | NM_018646 | 143 |
| 8020795 | TTR | NM_000371 | 1794 |
| 8026490 | UCA1 | DQ249310 | 742 |
| 8035318 | UNC13A | NM_001080421 | 2037 |
| 7952451 | UNQ565 | BC040288 | 208 |
| 7944341 | UPK2 | NM_006760 | 1979 |
| 7984132 | USP3 | NM_006537 | 555 |
| 7965565 | USP44 | NM_032147 | 875 |
| 8043197 | VAMP8 | NM_003761 | 2133 |
| 8106743 | VCAN | NM_004385 | 1951 |
| 8128818 | WASF1 | NM_003931 | 670 |

TABLE 2-continued

| Probe Set ID | Gene Symbol | mRNA Accession GENSCAN | SEQ ID NO: |
|---|---|---|---|
| 8088180 | WNT5A | NM_003392 | 371 |
| 8108287 | WNT8A | NM_058244 | 791 |
| 8008819 | YPEL2 | NM_001005404 | 570 |
| 8023871 | ZADH2 | NM_175907 | 1829 |
| 7980344 | ZDHHC22 | NM_174976 | 1114 |
| 8055624 | ZEB2 | NM_014795 | 2043 |
| 8002692 | ZFHX3 | NM_006885 | 998 |
| 8147837 | ZFPM2 | NM_012082 | 1851 |
| 8170200 | ZIC3 | NM_003413 | 1554 |
| 8099364 | ZNF518B | NM_053042 | 593 |
| 8022612 | ZNF521 | NM_015461 | 1786 |
| 8038981 | ZNF611 | NM_030972 | 1917 |
| 8039025 | ZNF702P | NR_003578 | 1172 |
| 8145829 | ZNF703 | NM_025069 | 79 |
| 8151496 | ZNF704 | NM_001033723 | 2154 |
| 7901497 | ZYG11A | AY271826 | 277 |
| 7972567 | ZIC5 | NM_033132 | 1006 |
| 8045088 | — | ENST00000363562 | 2366 |
| 8151625 | REXO1L1 | AF495523 | 209 |
| 8094134 | DUB4//DUB4 | AY533200 | 418 |
| 8165692 | — | NC_001807 | 119 |
| 8165656 | — | NC_001807 | 119 |
| 8165680 | — | NC_001807 | 119 |
| 8165709 | — | NC_001807 | 119 |
| 8165707 | — | NC_001807 | 119 |
| 8002342 | — | ENST00000387168 | 2459 |
| 7985569 | — | ENST00000386569 | 2444 |
| 7974255 | — | ENST00000364619 | 2389 |
| 8090637 | — | ENST00000321828 | 2493 |
| 8105935 | — | AK296222 | 1571 |
| 8112519 | — | AK296222 | 1571 |
| 8105987 | — | AK296222 | 1571 |
| 7896754 | — | AK290103 | 1297 |
| 8141843 | — | uc003vad.1 | 2521 |
| 8145685 | — | L17325 | 4 |
| 8102728 | — | GENSCAN00000041881 | 2504 |
| 7909142 | — | EU137727 | 1301 |
| 8135929 | — | ENST00000411257 | 2417 |

TABLE 2-continued

| Probe Set ID | Gene Symbol | mRNA Accession GENSCAN | SEQ ID NO: |
|---|---|---|---|
| 8094717 | — | ENST00000411246 | 2494 |
| 7926979 | — | ENST00000411115 | 2391 |
| 7905127 | — | ENST00000410896 | 2421 |
| 8161693 | — | ENST00000410867 | 2533 |
| 8110668 | — | ENST00000410601 | 2396 |
| 7997700 | — | ENST00000410584 | 2455 |
| 8078603 | — | ENST00000410276 | 2400 |
| 8173607 | — | ENST00000410263 | 2540 |
| 8098326 | — | ENST00000410173 | 2498 |
| 8127423 | — | ENST00000408661 | 2512 |
| 8116651 | — | ENST00000408316 | 2408 |
| 8138487 | — | ENST00000406252 | 2518 |
| 7967870 | — | ENST00000404119 | 2431 |
| 7915563 | — | ENST00000402946 | 2423 |
| 8129039 | — | ENST00000398296 | 2513 |
| 7919854 | — | ENST00000391210 | 2353 |
| 8008644 | — | ENST00000391167 | 2345 |
| 7986442 | — | ENST00000391004 | 2331 |
| 8132690 | — | ENST00000390855 | 2399 |
| 7944970 | — | ENST00000388707 | 2427 |
| 8151432 | — | ENST00000388687 | 2526 |
| 8146788 | — | ENST00000388485 | 2523 |
| 8096457 | — | ENST00000388444 | 2495 |
| 8173156 | — | ENST00000388375 | 2539 |
| 8088952 | — | ENST00000388353 | 2492 |
| 8133038 | — | ENST00000388343 | 2515 |
| 8008965 | — | ENST00000388323 | 2462 |
| 8112881 | — | ENST00000388321 | 2508 |
| 7989193 | — | ENST00000388282 | 2448 |
| 8139767 | — | ENST00000388117 | 2519 |
| 8100941 | — | ENST00000388112 | 2501 |
| 7901746 | — | ENST00000387999 | 2420 |
| 8031867 | — | ENST00000387967 | 2468 |
| 8154868 | — | ENST00000387953 | 2527 |
| 7987572 | — | ENST00000387750 | 2447 |
| 8166264 | — | ENST00000387726 | 2536 |
| 8117565 | — | ENST00000387717 | 2511 |
| 8144951 | — | ENST00000387614 | 2522 |
| 8131813 | — | ENST00000387559 | 2514 |

TABLE 2-continued

| Probe Set ID | Gene Symbol | mRNA Accession GENSCAN | SEQ ID NO: |
|---|---|---|---|
| 7995350 | — | ENST00000387385 | 2453 |
| 7963137 | — | ENST00000387378 | 2430 |
| 7941563 | — | ENST00000387367 | 2426 |
| 8149273 | — | ENST00000387366 | 2525 |
| 7995330 | — | ENST00000387329 | 2452 |
| 8013523 | — | ENST00000387253 | 2466 |
| 8085714 | — | ENST00000387170 | 2491 |
| 8000690 | — | ENST00000387168 | 2457 |
| 8013354 | — | ENST00000387105 | 2464 |
| 7979412 | — | ENST00000387089 | 2439 |
| 7899484 | — | ENST00000387056 | 2419 |
| 8077526 | — | ENST00000387004 | 2489 |
| 7999884 | — | ENST00000386991 | 2456 |
| 7970973 | — | ENST00000386783 | 2437 |
| 7992893 | — | ENST00000386778 | 2450 |
| 8011112 | — | ENST00000386729 | 2463 |
| 7970565 | — | ENST00000386673 | 2436 |
| 7967898 | — | ENST00000386647 | 2432 |
| 7990963 | — | ENST00000386569 | 2449 |
| 8168644 | — | ENST00000386562 | 2537 |
| 8162529 | — | ENST00000386448 | 2534 |
| 8107204 | — | ENST00000386442 | 2505 |
| 8134374 | — | ENST00000386220 | 2516 |
| 7985999 | — | ENST00000386201 | 2445 |
| 8108180 | — | ENST00000386126 | 2506 |
| 8114211 | — | ENST00000386114 | 2509 |
| 8174975 | — | ENST00000385990 | 2543 |
| 8147990 | — | ENST00000385963 | 2524 |
| 8054354 | — | ENST00000385923 | 2484 |
| 7919761 | — | ENST00000385919 | 2425 |
| 8158684 | — | ENST00000385827 | 2530 |
| 8055202 | — | ENST00000385681 | 2485 |
| 8136654 | — | ENST00000385604 | 2517 |
| 8045846 | — | ENST00000385489 | 2481 |
| 7909839 | — | ENST00000385445 | 2422 |
| 8058340 | — | ENST00000385403 | 2486 |
| 8047557 | — | ENST00000385394 | 2482 |
| 8058516 | — | ENST00000385377 | 2487 |

TABLE 2-continued

| Probe Set ID | Gene Symbol | mRNA Accession GENSCAN | SEQ ID NO: |
|---|---|---|---|
| 8058664 | — | ENST00000385364 | 2488 |
| 7982248 | — | ENST00000384701 | 2375 |
| 7987025 | — | ENST00000384699 | 2347 |
| 8102787 | — | ENST00000384592 | 2358 |
| 8016429 | — | ENST00000384576 | 2328 |
| 7919405 | — | ENST00000384499 | 2354 |
| 7984213 | — | ENST00000384494 | 2364 |
| 7919392 | — | ENST00000384487 | 2424 |
| 8169634 | — | ENST00000384446 | 2398 |
| 7993846 | — | ENST00000384315 | 2343 |
| 8016412 | — | ENST00000384227 | 2384 |
| 8112894 | — | ENST00000384047 | 2360 |
| 8078260 | — | ENST00000384001 | 2349 |
| 8093126 | — | ENST00000383917 | 2329 |
| 7915612 | — | ENST00000365574 | 2380 |
| 7965675 | — | ENST00000365498 | 2412 |
| 8068014 | — | ENST00000365469 | 2413 |
| 8050350 | — | ENST00000365378 | 2348 |
| 8021372 | — | ENST00000365289 | 2332 |
| 8161440 | — | ENST00000365217 | 2531 |
| 8056045 | — | ENST00000365159 | 2410 |
| 8168079 | — | ENST00000364816 | 2377 |
| 7945829 | — | ENST00000364746 | 2407 |
| 8054870 | — | ENST00000364714 | 2394 |
| 8125123 | — | ENST00000364685 | 2365 |
| 8012218 | — | ENST00000364619 | 2389 |
| 8117018 | — | ENST00000364497 | 2411 |
| 7934297 | — | ENST00000364177 | 2404 |
| 7963263 | — | ENST00000364083 | 2362 |
| 7996260 | — | ENST00000364041 | 2454 |
| 8016519 | — | ENST00000364033 | 2393 |
| 7942912 | — | ENST00000364007 | 2386 |
| 8095214 | — | ENST00000363871 | 2356 |
| 7922400 | — | ENST00000363840 | 2350 |
| 8166948 | — | ENST00000363832 | 2333 |
| 7950370 | — | ENST00000363779 | 2359 |
| 8128886 | — | ENST00000363652 | 2334 |
| 8015737 | — | ENST00000363640 | 2387 |
| 8155246 | — | ENST00000363632 | 2392 |

TABLE 2-continued

| Probe Set ID | Gene Symbol | mRNA Accession GENSCAN | SEQ ID NO: |
|---|---|---|---|
| 7999362 | — | ENST00000363598 | 2370 |
| 7944867 | — | ENST00000363408 | 2341 |
| 7973054 | — | ENST00000363355 | 2340 |
| 8042970 | — | ENST00000363158 | 2401 |
| 7965478 | — | ENST00000363141 | 2352 |
| 7995306 | — | ENST00000363132 | 2451 |
| 7965429 | — | ENST00000363025 | 2416 |
| 8040630 | — | ENST00000363002 | 2368 |
| 7984257 | — | ENST00000362698 | 2395 |
| 8108422 | — | ENST00000362675 | 2390 |
| 8157231 | — | ENST00000362655 | 2397 |
| 8107857 | — | ENST00000362585 | 2388 |
| 8003087 | — | ENST00000362480 | 2406 |
| 7944525 | — | ENST00000362347 | 2376 |
| 7933043 | — | ENST00000362330 | 2342 |
| 8095402 | — | ENST00000359217 | 2385 |
| 8115443 | — | ENST00000354652 | 2510 |
| 8174195 | — | ENST00000348857 | 2541 |
| 8168674 | — | ENST00000341395 | 2538 |
| 8097011 | — | ENST00000341244 | 2496 |
| 8155354 | — | ENST00000340909 | 2528 |
| 8163714 | — | ENST00000332944 | 2535 |
| 8174281 | — | ENST00000332317 | 2542 |
| 8084064 | — | ENST00000320415 | 2335 |
| 8139879 | — | ENST00000304821 | 2520 |
| 8023526 | — | ENST00000303758 | 2403 |
| 7974471 | — | ENST00000254302 | 2346 |
| 8148964 | — | BC131690 | 1065 |
| 8116653 | — | BC131577 | 1121 |
| 8060736 | — | BC008667 | 91 |
| 8088636 | — | AY358705 | 322 |
| 8041170 | — | AM413034 | 1005 |
| 7970989 | — | AK301863 | 1568 |
| 7909990 | — | AK290103 | 1297 |
| 8100308 | — | AK125574 | 307 |
| 8134429 | — | AK096576 | 165 |
| 8131967 | — | AK056230 | 111 |
| 8110666 | — | AK026811 | 58 |

TABLE 2-continued

| Probe Set ID | Gene Symbol | mRNA Accession GENSCAN | SEQ ID NO: |
|---|---|---|---|
| 7967025 | — | AF258551 | 61 |
| 8053834 | ANKRD36B | NM_025190 | 1956 |
| 8043697 | ANKRD36B | NM_025190 | 1956 |
| 7944035 | APOC3 | NM_000040 | 26 |
| 8142098 | ATXN7L1 | NM_020725 | 1316 |
| 7998117 | C20orf69 | BC118988 | 909 |
| 7927095 | C20orf69 | BC118988 | 909 |
| 8097064 | C20orf69 | BC118988 | 909 |
| 8038292 | CGB5 | NM_033043 | 100 |
| 8155460 | CNTNAP3 | NM_033655 | 985 |
| 7906878 | DDR2 | NM_001014796 | 622 |
| 8155376 | FAM74A4 | BC121813 | 911 |
| 8161467 | FAM74A4 | BC121813 | 911 |
| 8155388 | FAM74A4 | BC121813 | 911 |
| 8144388 | FAM90A1 | NM_018088 | 1112 |
| 8144448 | FAM90A1 | NM_018088 | 1112 |
| 8144444 | FAM90A1 | NM_018088 | 1112 |
| 8149204 | FAM90A1 | NM_018088 | 1112 |
| 7919584 | HIST2H2BF | NM_001024599 | 1910 |
| 8179322 | HSPA1A | NM_005345 | 1552 |
| 8179324 | HSPA1B | NM_005346 | 1350 |
| 7956488 | KIF5A | NM_004984 | 422 |
| 8000676 | LOC23117 | NM_130464 | 2066 |
| 8000131 | LOC23117 | NM_130464 | 2066 |
| 8022320 | LOC440350 | NM_001018122 | 1109 |
| 8000222 | LOC595101 | NR_002453 | 750 |
| 8000687 | LOC641298 | AK300040 | 1576 |
| 8002333 | LOC641298 | AK300040 | 1576 |
| 8000823 | LOC641298 | AK300040 | 1576 |
| 8000156 | LOC641298 | AK300040 | 1576 |
| 8144699 | LRLE1//LRLE1 | AY461701 | 344 |
| 7997239 | NPIP | AK294177 | 1567 |
| 8000501 | NPIP | AK294177 | 1567 |
| 8000537 | NPIP | AK294177 | 1567 |
| 8074577 | PI4KAP2 | NR_003700 | 1237 |
| 8089015 | PROS1 | NM_000313 | 1846 |
| 7941707 | RBM14 | NM_006328 | 1616 |
| 8180144 | RGL2 | NM_004761 | 1963 |
| 7978568 | RNU1A | NR_004421 | 1304 |

TABLE 2-continued

| Probe Set ID | Gene Symbol | mRNA Accession GENSCAN | SEQ ID NO: |
|---|---|---|---|
| 8021181 | SCARNA17 | NR_003003 | 833 |
| 7943158 | SCARNA9 | NR_002569 | 729 |
| 8086752 | SNORD13 | NR_003041 | 845 |
| 7938366 | WEE1 | BX641032 | 301 |
| 8121130 | — | AF074983 | 13 |
| 8073548 | ספטמבר-03 | NM_019106 | 1245 |
| 8174692 | ספטמבר-06 | NM_145799 | 1251 |
| 7897960 | AADACL3 | NM_001103170 | 1256 |
| 8103706 | AADAT | NM_016228 | 284 |
| 8140752 | ABCB4 | NM_000443 | 912 |
| 7903119 | ABCD3 | NM_002858 | 1382 |
| 8034974 | ABHD9 | NM_024794 | 1774 |
| 7975607 | ACOT4 | NM_152331 | 1434 |
| 8018558 | ACOX1 | NM_004035 | 2125 |
| 8008321 | ACSF2 | NM_025149 | 1236 |
| 8048733 | ACSL3 | NM_004457 | 407 |
| 8062041 | ACSS2 | NM_018677 | 1937 |
| 7924910 | ACTA1 | NM_001100 | 451 |
| 8042788 | ACTG2 | NM_001615 | 641 |
| 7941662 | ACTN3 | NM_001104 | 24 |
| 8066431 | ADA | NM_000022 | 452 |
| 8050190 | ADAM17 | NM_003183 | 706 |
| 8115490 | ADAM19 | NM_033274 | 2146 |
| 8047788 | ADAM23 | NM_003812 | 707 |
| 8145293 | ADAM28 | NM_014265 | 858 |
| 8100870 | ADAMTS3 | NM_014243 | 2326 |
| 8104394 | ADCY2 | NM_020546 | 941 |
| 8160297 | ADFP | NM_001122 | 2309 |
| 7938390 | ADM | NM_001124 | 16 |
| 8099259 | AFAP1 | NM_198595 | 1042 |
| 7924987 | AGT | NM_000029 | 1460 |
| 8122807 | AKAP12 | NM_005100 | 1643 |
| 8136336 | AKR1B10 | NM_020299 | 1842 |
| 7931832 | AKR1C2 | NM_001354 | 421 |
| 7925929 | AKR1C3 | NM_003739 | 199 |
| 8136459 | AKR1D1 | NM_005989 | 2145 |
| 8095628 | ALB | NM_000477 | 1754 |
| 8081431 | ALCAM | NM_001627 | 671 |

TABLE 2-continued

| Probe Set ID | Gene Symbol | mRNA Accession GENSCAN | SEQ ID NO: |
|---|---|---|---|
| 8155327 | ALDH1B1 | NM_000692 | 207 |
| 8023528 | ALPK2 | NM_052947 | 1146 |
| 7898693 | ALPL | NM_000478 | 2081 |
| 8049128 | ALPPL2 | NM_031313 | 1260 |
| 7957452 | ALX1 | NM_006982 | 1219 |
| 7918416 | ALX3 | NM_006492 | 922 |
| 8161415 | ANKRD20B | NR_003366 | 1141 |
| 7934898 | ANKRD22 | NM_144590 | 1210 |
| 8053801 | ANKRD36B | NM_025190 | 1956 |
| 7954997 | ANO6 | NM_001025356 | 1768 |
| 7991335 | ANPEP | NM_001150 | 1261 |
| 7989335 | ANXA2 | NM_001002857 | 506 |
| 8154836 | ANXA2P2 | NR_003573 | 1159 |
| 8042468 | ANXA4 | NM_001153 | 1362 |
| 8047300 | AOX1 | NM_001159 | 697 |
| 8034084 | AP1M2 | NM_005498 | 1807 |
| 8017210 | AP1S2 | AK299921 | 1574 |
| 8077204 | APOC3 | NM_000040 | 26 |
| 8017766 | APOH | NM_000042 | 1194 |
| 8160670 | AQP3 | NM_004925 | 169 |
| 8144315 | ARHGEF10 | BC026965 | 171 |
| 7950473 | ARRB1 | NM_004041 | 2269 |
| 7986350 | ARRDC4 | NM_183376 | 1522 |
| 8149534 | ASAH1 | NM_004315 | 1468 |
| 8152867 | ASAP1 | NM_018482 | 436 |
| 7906819 | ATF6 | NM_007348 | 579 |
| 7993167 | ATF7IP2 | NM_024997 | 346 |
| 8077858 | ATG7 | NM_001136031 | 1826 |
| 7937314 | ATHL1 | NM_025092 | 1437 |
| 7968062 | ATP12A | NM_001676 | 2128 |
| 7906501 | ATP1A2 | NM_000702 | 1681 |
| 7968270 | ATP5EP2//ATP5EP2 | NR_002162 | 490 |
| 8143221 | ATP6V0A4 | NM_020632 | 776 |
| 8147145 | ATP6V0D2 | NM_152565 | 181 |
| 8040249 | ATP6V1C2 | NM_001039362 | 784 |
| 8176276 | ATRX | NM_000489 | 1072 |
| 8142096 | ATXN7L1 | NM_020725 | 1316 |
| 8133233 | AUTS2 | NM_015570 | 1438 |
| 8042211 | B3GNT2 | NM_006577 | 815 |

TABLE 2-continued

| Probe Set ID | Gene Symbol | mRNA Accession GENSCAN | SEQ ID NO: |
|---|---|---|---|
| 8160637 | B4GALT1 | NM_001497 | 1533 |
| 8125766 | BAK1 | NM_001188 | 883 |
| 8029489 | BCAM | NM_005581 | 610 |
| 7961829 | BCAT1 | NM_005504 | 2100 |
| 8038202 | BCAT2 | NM_001190 | 1966 |
| 8077441 | BHLHE40 | NM_003670 | 1624 |
| 7927681 | BICC1 | NM_001080512 | 1031 |
| 8127193 | BMP5 | NM_021073 | 204 |
| 8132250 | BMPER | NM_133468 | 1629 |
| 8047538 | BMPR2 | NM_001204 | 1495 |
| 8160260 | BNC2 | NM_017637 | 846 |
| 7937079 | BNIP3 | NM_004052 | 45 |
| 8081686 | BOC | NM_033254 | 342 |
| 8153678 | BOP1 | NM_015201 | 366 |
| 7922095 | BRP44 | NM_015415 | 2308 |
| 8035304 | BST2 | NM_004335 | 43 |
| 7908917 | BTG2 | NM_006763 | 236 |
| 8117458 | BTN3A1 | NM_007048 | 1833 |
| 8128553 | BVES | NM_147147 | 2228 |
| 7936419 | C10orf118 | NM_018017 | 319 |
| 7971486 | C13orf18 | NM_025113 | 1235 |
| 7979483 | C14orf39 | NM_174978 | 1520 |
| 7981273 | C14orf65 | AK123840 | 305 |
| 7990027 | C15orf28 | BC136847 | 1447 |
| 8001178 | C16orf87 | BC056676 | 313 |
| 8018264 | C17orf28 | NM_030630 | 1457 |
| 8022310 | C18orf58 | AK092226 | 160 |
| 7907396 | C1orf105 | BC038410 | 187 |
| 7925561 | C1orf199 | AK095297 | 163 |
| 7905147 | C1orf54 | BC017761 | 116 |
| 7897119 | C1orf93 | BC022547 | 123 |
| 8060940 | C20orf103 | NM_012261 | 2245 |
| 7911329 | C20orf69 | BC118988 | 909 |
| 8067932 | C21orf34 | NM_001005732 | 541 |
| 8102518 | C4orf3 | NM_001001701 | 1212 |
| 8163839 | C5 | NM_001735 | 334 |
| 8107194 | C5orf30 | BC009203 | 289 |
| 8123951 | C6orf105 | BC007011 | 85 |

TABLE 2-continued

| Probe Set ID | Gene Symbol | mRNA Accession GENSCAN | SEQ ID NO: |
|---|---|---|---|
| 8121002 | C6orf162 | NM_001042493 | 886 |
| 8121911 | C6orf173 | NM_001012507 | 1737 |
| 8129392 | C6orf174 | NM_001012279 | 1930 |
| 8135902 | C7orf54 | NM_014411 | 731 |
| 8149315 | C8orf15 | BC132953 | 1038 |
| 8144712 | C8orf79 | NM_001099677 | 1190 |
| 8038126 | CA11 | NM_001217 | 621 |
| 7905131 | CA14 | NM_012113 | 40 |
| 7951807 | CADM1 | NM_014333 | 1149 |
| 8088491 | CADPS | NM_003716 | 1637 |
| 8151730 | CALB1 | NM_004929 | 38 |
| 7963721 | CALCOCO1 | NM_020898 | 1777 |
| 7909425 | CAMK1G | NM_020439 | 379 |
| 7909967 | CAPN2 | NM_001748 | 1274 |
| 8102311 | CASP6 | NM_001226 | 705 |
| 7912347 | CASZ1 | NM_001079843 | 1019 |
| 8001329 | CBLN1 | NM_004352 | 2082 |
| 8023575 | CCBE1 | NM_133459 | 2057 |
| 8131871 | CCDC126 | NM_138771 | 829 |
| 8052269 | CCDC88A | NM_001135597 | 1667 |
| 7967486 | CCDC92 | NM_025140 | 80 |
| 7938090 | CCKBR | NM_176875 | 279 |
| 8095870 | CCNG2 | NM_004354 | 1428 |
| 8089299 | CD47 | NM_001777 | 672 |
| 7909332 | CD55 | NM_001114752 | 1363 |
| 7953291 | CD9 | NM_001769 | 2261 |
| 8142878 | CDC26 | AF503918 | 140 |
| 7919888 | CDC42SE1 | NM_001038707 | 768 |
| 8001800 | CDH11 | NM_001797 | 107 |
| 8022674 | CDH2 | NM_001792 | 1744 |
| 7996819 | CDH3 | NM_001793 | 1471 |
| 8175531 | CDR1 | NM_004065 | 411 |
| 8096130 | CDS1 | NM_001263 | 1579 |
| 8051528 | CEBPZ | NM_005760 | 400 |
| 8102328 | CFI | NM_000204 | 1348 |
| 8038280 | CGB | NM_000737 | 102 |
| 8038288 | CGB1 | NM_033377 | 103 |
| 8030181 | CGB2 | NM_033378 | 104 |
| 8030187 | CGB5 | NM_033043 | 100 |

TABLE 2-continued

| Probe Set ID | Gene Symbol | mRNA Accession GENSCAN | SEQ ID NO: |
|---|---|---|---|
| 8038299 | CGB7 | NM_033142 | 101 |
| 7905406 | CGN | NM_020770 | 1429 |
| 7983867 | CGNL1 | NM_032866 | 571 |
| 8154785 | CHMP5 | NM_016410 | 2195 |
| 8056890 | CHN1 | NM_001822 | 2318 |
| 8022666 | CHST9 | NM_031422 | 2002 |
| 7996891 | CIRH1A | NM_032830 | 1419 |
| 7983256 | CKMT1A | NM_001015001 | 654 |
| 8092726 | CLDN1 | NM_021101 | 2121 |
| 8083887 | CLDN11 | NM_005602 | 1602 |
| 8082928 | CLDN18 | NM_001002026 | 600 |
| 8133360 | CLDN4 | NM_001305 | 300 |
| 8069795 | CLDN8 | NM_199328 | 2124 |
| 7961111 | CLEC1A | NM_016511 | 324 |
| 8058127 | CLK1 | NM_004071 | 1926 |
| 8021727 | CNDP2 | NM_018235 | 2019 |
| 8025918 | CNN1 | NM_001299 | 573 |
| 8043657 | CNNM4 | NM_020184 | 844 |
| 8128043 | CNR1 | NM_016083 | 1906 |
| 7954899 | CNTN1 | NM_001843 | 231 |
| 8077323 | CNTN4 | NM_175607 | 2262 |
| 8161288 | CNTNAP3 | NM_033655 | 985 |
| 8127563 | COL12A1 | NM_004370 | 822 |
| 8148070 | COL14A1 | NM_021110 | 549 |
| 7962703 | COL2A1 | NM_001844 | 902 |
| 8059905 | COL6A3 | NM_004369 | 1515 |
| 8021946 | COLEC12 | NM_130386 | 1621 |
| 8091385 | CP | NM_000096 | 1498 |
| 7964834 | CPM | NM_001874 | 1733 |
| 7949971 | CPT1A | NM_001876 | 1465 |
| 8138805 | CPVL | NM_019029 | 751 |
| 7936835 | CPXM2 | NM_198148 | 1836 |
| 7922051 | CREG1 | NM_003851 | 534 |
| 8151092 | CRH | NM_000756 | 2078 |
| 8106418 | CRHBP | NM_001882 | 453 |
| 8041447 | CRIM1 | NM_016441 | 2217 |
| 8126905 | CRISP3 | NM_006061 | 2149 |
| 8133938 | CROT | NM_021151 | 1811 |

TABLE 2-continued

| Probe Set ID | Gene Symbol | mRNA Accession GENSCAN | SEQ ID NO: |
|---|---|---|---|
| 7970455 | CRYL1 | NM_015974 | 947 |
| 7914950 | CSF3R | NM_156039 | 2186 |
| 7923378 | CSRP1 | NM_004078 | 1812 |
| 8103389 | CTSO | NM_001334 | 340 |
| 8067279 | CTSZ | NM_001336 | 1680 |
| 7926127 | CUGBP2 | NM_001025077 | 1090 |
| 8055465 | CXCR4 | NM_001008540 | 580 |
| 8049471 | CXCR7 | NM_020311 | 930 |
| 8023855 | CYB5A | NM_148923 | 2257 |
| 7946292 | CYB5R2 | NM_016229 | 855 |
| 8176709 | CYorf15B | NM_032576 | 1796 |
| 8051583 | CYP1B1 | NM_000104 | 1503 |
| 8067140 | CYP24A1 | NM_000782 | 1526 |
| 8052947 | CYP26B1 | NM_019885 | 275 |
| 8028991 | CYP2S1 | NM_030622 | 518 |
| 8026424 | CYP4F22 | NM_173483 | 1295 |
| 7901272 | CYP4X1 | NM_178033 | 244 |
| 7902687 | CYR61 | NM_001554 | 1635 |
| 8069668 | CYYR1 | NM_052954 | 431 |
| 7971950 | DACH1 | NM_080759 | 1975 |
| 7974689 | DACT1 | NM_016651 | 999 |
| 8079753 | DAG1 | NM_004393 | 2084 |
| 7955464 | DAZAP2 | NM_014764 | 1714 |
| 8044804 | DBI | NM_020548 | 2095 |
| 8097753 | DCLK2 | NM_001040260 | 2194 |
| 8019357 | DCXR | NM_016286 | 2187 |
| 7939738 | DDB2 | NM_000107 | 1318 |
| 8145922 | DDHD2 | NM_015214 | 1954 |
| 7964460 | DDIT3 | NM_004083 | 2185 |
| 7906900 | DDR2 | AY423733 | 389 |
| 8160559 | DDX58 | NM_014314 | 733 |
| 7918768 | DENND2C | NM_198459 | 1023 |
| 8154531 | DENND4C | NM_017925 | 848 |
| 8138602 | DFNA5 | NM_004403 | 978 |
| 7936949 | DHX32 | NM_018180 | 137 |
| 7971653 | DLEU2 | NR_002612 | 756 |
| 8135480 | DNAJB9 | NM_012328 | 2223 |
| 7974190 | DNAJC19 | BC009702 | 109 |
| 7902043 | DNAJC6 | NM_014787 | 552 |

TABLE 2-continued

| Probe Set ID | Gene Symbol | mRNA Accession GENSCAN | SEQ ID NO: |
|---|---|---|---|
| 8068422 | DOPEY2 | NM_005128 | 428 |
| 8089438 | DPPA2 | NM_138815 | 1921 |
| 7953665 | DPPA3 | NM_199286 | 519 |
| 8127522 | DPPA5 | NM_001025290 | 2234 |
| 8145470 | DPYSL2 | NM_001386 | 503 |
| 8022692 | DSC3 | NM_024423 | 1142 |
| 8068512 | DSCR6 | NM_018962 | 1698 |
| 8023727 | DSEL | NM_032160 | 598 |
| 8113691 | DTWD2 | NM_173666 | 1619 |
| 8172035 | DYNLT3 | NM_006520 | 1717 |
| 8059748 | ECEL1 | NM_004826 | 1280 |
| 8097692 | EDNRA | NM_001957 | 1981 |
| 7965436 | EEA1 | NM_003566 | 890 |
| 8113433 | EFNA5 | NM_001962 | 1541 |
| 8016099 | EFTUD2 | NM_004247 | 1761 |
| 8105013 | EGFLAM | NM_152403 | 2314 |
| 7963575 | EIF4B | AF119854 | 48 |
| 7971197 | ELF1 | NM_172373 | 1855 |
| 8175039 | ELF4 | NM_001421 | 1431 |
| 8139057 | ELMO1 | NM_014800 | 2316 |
| 7943562 | ELMOD1 | NM_018712 | 1548 |
| 7915504 | ELOVL1 | NM_022821 | 398 |
| 8123920 | ELOVL2 | NM_017770 | 1271 |
| 8102342 | ELOVL6 | NM_024090 | 1597 |
| 7953532 | ENO2 | NM_001975 | 110 |
| 8147883 | ENY2 | NM_020189 | 2175 |
| 7898809 | EPHB2 | NM_017449 | 903 |
| 7961546 | EPS8 | NM_004447 | 1736 |
| 7971296 | EPSTI1 | NM_001002264 | 492 |
| 7952601 | ETS1 | NM_005238 | 1783 |
| 7921228 | ETV3 | NM_005240 | 134 |
| 8091972 | EVI1 | NM_001105078 | 1949 |
| 8130505 | EZR | NM_003379 | 1309 |
| 7970241 | F10 | NM_000504 | 793 |
| 8106403 | F2RL1 | NM_005242 | 1758 |
| 8010915 | FAM101B | NM_182705 | 969 |
| 8060370 | FAM110A | NM_031424 | 874 |
| 8094609 | FAM114A1 | BC040452 | 211 |

TABLE 2-continued

| Probe Set ID | Gene Symbol | mRNA Accession GENSCAN | SEQ ID NO: |
|---|---|---|---|
| 8055978 | FAM133B | BC057771 | 314 |
| 8105607 | FAM159B | ENST00000389074 | 2355 |
| 8088671 | FAM19A4 | NM_182522 | 536 |
| 8017867 | FAM20A | NM_017565 | 1927 |
| 8003357 | FAM38A | D87071 | 8 |
| 8155345 | FAM74A1//FAM74A3 | ENST00000355345 | 2363 |
| 8161407 | FAM74A4 | BC121813 | 911 |
| 8144440 | FAM90A1 | NM_018088 | 1112 |
| 7931281 | FANK1 | NM_145235 | 1143 |
| 7954631 | FAR2 | NM_018099 | 261 |
| 8097288 | FAT4 | NM_024582 | 1329 |
| 7988467 | FBN1 | NM_000138 | 2024 |
| 8108205 | FBXL21 | NM_012159 | 2033 |
| 8106141 | FCHO2 | NM_138782 | 1886 |
| 8064904 | FERMT1 | NM_017671 | 977 |
| 8051427 | FEZ2 | NM_005102 | 894 |
| 8078066 | FGD5 | NM_152536 | 1537 |
| 8150318 | FGFR1 | NM_023110 | 870 |
| 8170119 | FHL1 | NM_001449 | 1898 |
| 7939365 | FJX1 | NM_014344 | 1589 |
| 8125919 | FKBP5 | NM_004117 | 1865 |
| 8105144 | FLJ10246 | AK001108 | 42 |
| 7961440 | FLJ22662 | NM_024829 | 889 |
| 8144228 | FLJ36840 | AK094159 | 161 |
| 8054517 | FLJ38359 | AK095678 | 164 |
| 8131042 | FLJ44124 | XR_041001 | 1365 |
| 7909628 | FLVCR1 | NM_014053 | 2270 |
| 8170326 | FMR1 | NM_002024 | 2127 |
| 7914580 | FNDC5 | NM_153756 | 2046 |
| 8168205 | FOXO4 | NM_005938 | 2032 |
| 7902308 | FPGT | NM_003838 | 2225 |
| 8129071 | FRK | NM_002031 | 266 |
| 7975136 | FUT8 | NM_178155 | 2321 |
| 8027748 | FXYD3 | NM_021910 | 1694 |
| 8145611 | FZD3 | NM_017412 | 2230 |
| 7950885 | FZD4 | NM_012193 | 178 |
| 8058498 | FZD5 | NM_003468 | 905 |
| 8047487 | FZD7 | NM_003507 | 21 |
| 8007561 | G6PC3 | NM_138387 | 1978 |

TABLE 2-continued

| Probe Set ID | Gene Symbol | mRNA Accession GENSCAN | SEQ ID NO: |
|---|---|---|---|
| 8046283 | GAD1 | NM_000817 | 589 |
| 8137448 | GALNT11 | NM_022087 | 1201 |
| 8056408 | GALNT3 | NM_004482 | 1195 |
| 8031622 | GALP | NM_033106 | 1861 |
| 8081810 | GAP43 | NM_001130064 | 1551 |
| 8020455 | GATA6 | NM_005257 | 361 |
| 7988414 | GATM | NM_001482 | 1062 |
| 8094361 | GBA3 | NM_020973 | 1519 |
| 8088958 | GBE1 | NM_000158 | 1497 |
| 8164833 | GBGT1 | NM_021996 | 1227 |
| 7917779 | GCLM | NM_002061 | 535 |
| 8027002 | GDF15 | NM_004864 | 1203 |
| 7936494 | GFRA1 | NM_005264 | 1858 |
| 8121749 | GJA1 | NM_000165 | 1034 |
| 8044933 | GLI2 | NM_005270 | 1516 |
| 8155192 | GLIPR2 | NM_022343 | 167 |
| 8159900 | GLIS3 | NM_152629 | 882 |
| 8115355 | GLRA1 | NM_000171 | 1879 |
| 7964183 | GLS2 | NM_013267 | 136 |
| 7965941 | GLT8D2 | NM_031302 | 1106 |
| 7962349 | GLT8D3 | NM_173601 | 1199 |
| 7916843 | GNG12 | NM_018841 | 2158 |
| 7974341 | GNG2 | NM_053064 | 1022 |
| 7925250 | GNG4 | NM_001098721 | 1164 |
| 8174509 | GNG5//GNG5 | BT006823 | 250 |
| 7965812 | GNPTAB | NM_024312 | 2102 |
| 8071274 | GP1BB | L20860 | 5 |
| 8175234 | GPC3 | NM_004484 | 1962 |
| 7967318 | GPR109A | NM_177551 | 378 |
| 8056837 | GPR155 | NM_001033045 | 721 |
| 8157727 | GPR21 | NM_005294 | 33 |
| 8142687 | GPR37 | NM_005302 | 258 |
| 8171624 | GPR64 | NM_001079858 | 2117 |
| 8105348 | GPX8 | NM_001008397 | 1525 |
| 7990138 | GRAMD2 | NM_001012642 | 1791 |
| 8139656 | GRB10 | NM_001001555 | 1782 |
| 8006940 | GRB7 | NM_001030002 | 698 |
| 7925452 | GREM2 | NM_022469 | 689 |

TABLE 2-continued

| Probe Set ID | Gene Symbol | mRNA Accession GENSCAN | SEQ ID NO: |
|---|---|---|---|
| 7898916 | GRHL3 | NM_198173 | 2182 |
| 8007620 | GRN | NM_002087 | 601 |
| 8127072 | GSTA1 | NM_145740 | 1741 |
| 8136849 | GSTK1 | NM_015917 | 1790 |
| 8085370 | GSTM1L | NR_003112 | 910 |
| 8123038 | GTF2H5 | NM_207118 | 1871 |
| 8121502 | GTF3C6 | NM_138408 | 1801 |
| 7951437 | GUCY1A2 | NM_000855 | 22 |
| 7939620 | GYLTL1B | NM_152312 | 964 |
| 8156610 | HABP4 | NM_014282 | 1284 |
| 7930559 | hCG_1776259 | AK027209 | 59 |
| 7961390 | HEBP1 | NM_015987 | 2152 |
| 8122317 | HEBP2 | NM_014320 | 391 |
| 7929145 | HECTD2 | NM_182765 | 1514 |
| 8057898 | HECW2 | NM_020760 | 548 |
| 7897280 | HES3 | NM_001024598 | 2045 |
| 8088285 | HESX1 | NM_003865 | 1394 |
| 8093278 | HGD | NM_000187 | 2104 |
| 7929282 | HHEX | NM_002729 | 1064 |
| 8097628 | HHIP | NM_022475 | 2285 |
| 8124380 | HIST1H1A | NM_005325 | 968 |
| 7919606 | HIST2H2BF | NM_001024599 | 1910 |
| 7919627 | HIST2H4A | NM_003548 | 242 |
| 8129953 | HIVEP2 | NM_006734 | 893 |
| 8180022 | HLA-DQB1 | M60028 | 2 |
| 8091354 | HLTF | NM_003071 | 993 |
| 7908204 | HMCN1 | NM_031935 | 1001 |
| 7956867 | HMGA2 | NM_003483 | 634 |
| 8111941 | HMGCS1 | NM_001098272 | 1134 |
| 8072678 | HMOX1 | NM_002133 | 2135 |
| 7991034 | HOMER2 | NM_199330 | 439 |
| 8138728 | HOXA4 | NM_002141 | 1148 |
| 8138745 | HOXA7 | NM_006896 | 762 |
| 8016487 | HOXB13 | NM_006361 | 759 |
| 8016452 | HOXB4 | NM_024015 | 774 |
| 8016476 | HOXB9 | NM_024017 | 777 |
| 7955873 | HOXC6 | NM_004503 | 824 |
| 7955869 | HOXC8 | NM_022658 | 425 |
| 8046555 | HOXD4 | NM_014621 | 186 |

TABLE 2-continued

| Probe Set ID | Gene Symbol | mRNA Accession GENSCAN | SEQ ID NO: |
|---|---|---|---|
| 7901087 | HPDL | NM_032756 | 491 |
| 8175195 | HS6ST2 | NM_001077188 | 973 |
| 7904414 | HSD3B1 | M27137 | 1 |
| 8118310 | HSPA1A | NM_005345 | 1552 |
| 8118314 | HSPA1B | NM_005346 | 1350 |
| 7975076 | HSPA2 | NM_021979 | 1126 |
| 7938880 | HTATIP2 | NM_001098520 | 1152 |
| 8120983 | HTR1E | NM_000865 | 1669 |
| 8068180 | HUNK | NM_014586 | 44 |
| 8061564 | ID1 | NM_181353 | 254 |
| 8117120 | ID4 | NM_001546 | 131 |
| 7991374 | IDH2 | NM_002168 | 227 |
| 7985134 | IDH3A | NM_005530 | 228 |
| 7929065 | IFIT1 | NM_001548 | 976 |
| 7937335 | IFITM1 | NM_003641 | 1174 |
| 8135514 | IFRD1 | NM_001550 | 2204 |
| 8013581 | IFT20 | NM_174887 | 298 |
| 8058857 | IGFBP5 | NM_000599 | 1396 |
| 8175121 | IGSF1 | NM_001555 | 2034 |
| 7918913 | IGSF3 | NM_001542 | 559 |
| 8059067 | IHH | NM_002181 | 2052 |
| 8068254 | IL10RB | NM_000628 | 192 |
| 8043995 | IL1R1 | NM_000877 | 223 |
| 8084794 | IL1RAP | NM_002182 | 2009 |
| 7922018 | ILDR2 | AF503509 | 278 |
| 8150908 | IMPAD1 | NM_017813 | 1269 |
| 7901804 | INADL | NM_176877 | 916 |
| 8058415 | INO80D | NM_017759 | 1139 |
| 7945688 | INS-IGF2 | NR_003512 | 2206 |
| 8059878 | IQCA1 | NM_024726 | 358 |
| 8174444 | IRS4 | NM_003604 | 1863 |
| 8107814 | ISOC1 | NM_016048 | 866 |
| 8035465 | ISYNA1 | NM_016368 | 2030 |
| 8046695 | ITGA4 | NM_000885 | 663 |
| 8078619 | ITGA9 | NM_002207 | 521 |
| 7926061 | ITIH2 | NM_002216 | 685 |
| 7916747 | JAK1 | NM_002227 | 865 |
| 8114938 | JAKMIP2 | NM_014790 | 414 |

TABLE 2-continued

| Probe Set ID | Gene Symbol | mRNA Accession GENSCAN | SEQ ID NO: |
|---|---|---|---|
| 7933877 | JMJD1C | NM_004241 | 677 |
| 8015412 | JUP | NM_002230 | 1730 |
| 7916654 | KANK4 | NM_181712 | 1229 |
| 8083546 | KCNAB1 | NM_003471 | 1276 |
| 8051785 | KCNG3 | NM_133329 | 2226 |
| 8009493 | KCNJ16 | NM_170742 | 206 |
| 7934570 | KCNMA1 | NM_001014797 | 1911 |
| 8152369 | KCNV1 | NM_014379 | 230 |
| 8127370 | KHDRBS2 | NM_152688 | 1491 |
| 8011293 | KIAA0664 | NM_015229 | 785 |
| 8020037 | KIAA0802 | BC040542 | 212 |
| 7926679 | KIAA1217 | NM_019590 | 1147 |
| 8122279 | KIAA1244 | NM_020340 | 1986 |
| 7936529 | KIAA1598 | NM_001127211 | 1433 |
| 8150036 | KIF13B | NM_015254 | 1254 |
| 8060134 | KIF1A | NM_004321 | 382 |
| 7962274 | KIF21A | NM_017641 | 2062 |
| 7956522 | KIF5A | AF063608 | 71 |
| 8040211 | KLF11 | NM_003597 | 368 |
| 7969414 | KLF5 | NM_001730 | 527 |
| 8167912 | KLF8 | NM_007250 | 1892 |
| 8038683 | KLK6 | NM_002774 | 613 |
| 8013465 | KRT16 | NM_005557 | 1313 |
| 7955637 | KRT18 | NM_199187 | 367 |
| 7945648 | KRTAP5-2 | NM_001004325 | 517 |
| 8045539 | KYNU | NM_003937 | 713 |
| 7901860 | L1TD1 | NM_019079 | 1968 |
| 8121949 | LAMA2 | NM_000426 | 1018 |
| 8142194 | LAMB1 | NM_002291 | 1354 |
| 8174779 | LAMP2 | NM_013995 | 1373 |
| 8092348 | LAMP3 | NM_014398 | 1249 |
| 8050548 | LAPTM4A | NM_014713 | 1608 |
| 8086125 | LBA1 | NM_014831 | 1961 |
| 7899753 | LCK | NM_005356 | 919 |
| 7924682 | LEFTY2 | NM_003240 | 2049 |
| 8099685 | LGI2 | NM_018176 | 1596 |
| 7999468 | LITAF | NM_004862 | 1708 |
| 8127425 | LMBRD1 | NM_018368 | 1993 |
| 8077490 | LMCD1 | NM_014583 | 92 |

TABLE 2-continued

| Probe Set ID | Gene Symbol | mRNA Accession GENSCAN | SEQ ID NO: |
|---|---|---|---|
| 7923386 | LMOD1 | NM_012134 | 913 |
| 8010978 | LOC100130876 | AK130278 | 302 |
| 7994026 | LOC100132247 | NM_001135865 | 1686 |
| 8119423 | LOC221442 | AK126092 | 309 |
| 8000205 | LOC23117 | NM_130464 | 2066 |
| 8004955 | LOC284033 | AK095052 | 162 |
| 7938368 | LOC387753 | XM_001724792 | 1366 |
| 8071042 | LOC389832 | AK124122 | 306 |
| 8008110 | LOC404266 | ENST00000376699 | 2460 |
| 8162183 | LOC440173 | AK299239 | 1572 |
| 8000636 | LOC440350 | NM_001018122 | 1109 |
| 7919596 | LOC440570//LOC440570 | AK125737 | 308 |
| 8052598 | LOC51057 | NM_015910 | 2275 |
| 7963280 | LOC57228 | NM_001033873 | 728 |
| 7994006 | LOC595101 | NR_002453 | 750 |
| 8000638 | LOC641298 | AK300040 | 1576 |
| 7909422 | LOC642587 | NM_001104548 | 1258 |
| 8086538 | LOC644714 | BC047037 | 232 |
| 7983132 | LOC645106 | AK122666 | 303 |
| 7985221 | LOC646934 | XR_018310 | 1916 |
| 7960896 | LOC650293 | NM_001040071 | 805 |
| 8049963 | LOC728323 | AK298283 | 1575 |
| 7898353 | LOC729574//LOC729587 | ENST00000344958 | 2418 |
| 7952339 | LOC85389 | NR_001453 | 1946 |
| 7952335 | LOC85391 | NR_003125 | 1947 |
| 8106722 | LOC92270 | NM_001017971 | 640 |
| 7995697 | LPCAT2 | NM_017839 | 1839 |
| 7924107 | LPGAT1 | NM_014873 | 1646 |
| 8095303 | LPHN3 | NM_015236 | 1314 |
| 8149248 | LRLE1//LRLE1 | AY461701 | 344 |
| 7973352 | LRP10 | NM_014045 | 592 |
| 7916282 | LRP8 | NM_004631 | 615 |
| 8120279 | LRRC1 | NM_018214 | 850 |
| 8147079 | LRRCC1 | NM_033402 | 2072 |
| 8135488 | LRRN3 | NM_001099660 | 1200 |
| 8053315 | LRRTM4 | NM_024993 | 1233 |
| 8148572 | LY6E | NM_002346 | 1435 |
| 8097773 | MAB21L2 | NM_006439 | 1592 |

TABLE 2-continued

| Probe Set ID | Gene Symbol | mRNA Accession GENSCAN | SEQ ID NO: |
|---|---|---|---|
| 8167656 | MAGED1 | NM_001005333 | 529 |
| 8043504 | MAL | NM_002371 | 74 |
| 7941272 | MALAT1 | NR_002819 | 1663 |
| 8054479 | MALL | NM_005434 | 1716 |
| 8155754 | MAMDC2 | NM_153267 | 1841 |
| 7951133 | MAML2 | NM_032427 | 276 |
| 8102862 | MAML3 | NM_018717 | 1300 |
| 8102006 | MANBA | NM_005908 | 769 |
| 8106098 | MAP1B | NM_005909 | 1207 |
| 8129804 | MAP3K5 | NM_005923 | 155 |
| 8171901 | MAP3K7IP3 | NM_152787 | 859 |
| 8101587 | MAPK10 | NM_138980 | 1960 |
| 8101925 | MAPKSP1 | NM_021970 | 1661 |
| 8092328 | MCCC1 | NM_020166 | 980 |
| 8119466 | MDFI | NM_005586 | 1436 |
| 7978801 | MDGA2 | NM_001113498 | 2159 |
| 8083360 | MED12L | NM_053002 | 2106 |
| 8015821 | MEOX1 | NM_004527 | 763 |
| 8120088 | MEP1A | NM_005588 | 1187 |
| 7960919 | MFAP5 | NM_003480 | 444 |
| 7991234 | MFGE8 | NM_005928 | 1356 |
| 8083656 | MFSD1 | NM_022736 | 2010 |
| 8047078 | MFSD6 | NM_017694 | 1113 |
| 8054135 | MGAT4A | NM_012214 | 747 |
| 8093332 | MGC26356 | BC046475 | 233 |
| 8097513 | MGST2 | NM_002413 | 2289 |
| 8160332 | MLLT3 | NM_004529 | 1230 |
| 8083494 | MME | NM_007288 | 967 |
| 8071758 | MMP11 | NM_005940 | 585 |
| 8151684 | MMP16 | AL136588 | 78 |
| 7995681 | MMP2 | NM_004530 | 1489 |
| 8160521 | MOBKL2B | NM_024761 | 2264 |
| 8174322 | MORC4 | NM_024657 | 2036 |
| 7967193 | MORN3 | NM_173855 | 2015 |
| 8175288 | MOSPD1 | NM_019556 | 52 |
| 8129573 | MOXD1 | NM_015529 | 995 |
| 8176174 | MPP1 | NM_002436 | 1996 |
| 8015868 | MPP2 | NM_005374 | 528 |
| 8131927 | MPP6 | NM_016447 | 147 |

TABLE 2-continued

| Probe Set ID | Gene Symbol | mRNA Accession GENSCAN | SEQ ID NO: |
|---|---|---|---|
| 7907092 | MPZL1 | NM_003953 | 1882 |
| 8120961 | MRAP2 | NM_138409 | 1241 |
| 8117194 | MRS2 | NM_020662 | 827 |
| 8093852 | MSX1 | NM_002448 | 1002 |
| 8042830 | MTHFD2 | NM_001040409 | 847 |
| 7970655 | MTMR6 | NM_004685 | 1088 |
| 8149485 | MTMR7 | NM_004686 | 1876 |
| 8149500 | MTUS1 | NM_001001924 | 1632 |
| 8148317 | MYC | NM_002467 | 1914 |
| 8086689 | MYL3 | NM_000258 | 952 |
| 8007921 | MYL4 | NM_001002841 | 507 |
| 8047127 | MYO1B | NM_001130158 | 1560 |
| 7989277 | MYO1E | NM_004998 | 561 |
| 8120783 | MYO6 | NM_004999 | 816 |
| 7916592 | MYSM1 | NM_001085487 | 2315 |
| 7943051 | NAALAD2 | NM_005467 | 1308 |
| 8047086 | NAB1 | NM_005966 | 572 |
| 8112478 | NAIP | NM_022892 | 1012 |
| 7953689 | NANOGP1 | AY455283 | 417 |
| 8067985 | NCAM2 | NM_004540 | 2249 |
| 8153002 | NDRG1 | NM_001135242 | 1662 |
| 8160587 | NDUFB6 | NM_002493 | 2250 |
| 7932453 | NEBL | NM_006393 | 1634 |
| 7989094 | NEDD4 | NM_006154 | 933 |
| 8072229 | NEFH | NM_021076 | 1612 |
| 8149835 | NEFL | NM_006158 | 1640 |
| 7908543 | NEK7 | NM_133494 | 1752 |
| 7909603 | NENF | NM_013349 | 1806 |
| 7979133 | NID2 | NM_007361 | 1110 |
| 7979044 | NIN | NM_020921 | 1138 |
| 7914326 | NKAIN1 | NM_024522 | 2118 |
| 8067602 | NKAIN4 | NM_152864 | 1891 |
| 8083968 | NLGN1 | NM_014932 | 253 |
| 8039280 | NLRP7 | NM_001127255 | 1446 |
| 8105153 | NNT | NM_012343 | 1032 |
| 8090737 | NPHP3 | NM_153240 | 2274 |
| 7994559 | NPIP | AK294177 | 1567 |
| 8096704 | NPNT | NM_001033047 | 2107 |

TABLE 2-continued

| Probe Set ID | Gene Symbol | mRNA Accession GENSCAN | SEQ ID NO: |
|---|---|---|---|
| 8164087 | NR6A1 | NM_033334 | 532 |
| 8047738 | NRP2 | NM_201266 | 393 |
| 8052091 | NRXN1 | NM_004801 | 1672 |
| 7976012 | NRXN3 | NM_004796 | 1281 |
| 8156134 | NTRK2 | NM_006180 | 650 |
| 7933537 | OGDHL | NM_018245 | 1814 |
| 7904158 | OLFML3 | NM_020190 | 496 |
| 8129872 | OLIG3 | NM_175747 | 255 |
| 8050497 | OSR1 | NM_145260 | 722 |
| 7941401 | OVOL1 | NM_004561 | 349 |
| 7961026 | OVOS | ENST00000334227 | 2429 |
| 7953873 | OVOS2 | NM_001080502 | 1030 |
| 8147848 | OXR1 | NM_181354 | 1558 |
| 7971565 | P2RY5 | NM_005767 | 1928 |
| 7934278 | P4HA1 | NM_000917 | 1759 |
| 8005473 | PAIP1 | NM_006451 | 1668 |
| 7907572 | PAPPA2 | NM_020318 | 962 |
| 7928944 | PAPSS2 | NM_004670 | 635 |
| 7947338 | PAX6 | NM_000280 | 1470 |
| 7906954 | PBX1 | NM_002585 | 2306 |
| 8168657 | PCDH11X | NM_032967 | 2017 |
| 8176400 | PCDH11Y | NM_032971 | 98 |
| 7969330 | PCDH17 | NM_001040429 | 934 |
| 8102792 | PCDH18 | NM_019035 | 1250 |
| 8173933 | PCDH19 | NM_001105243 | 1278 |
| 8108724 | PCDHB10 | NM_018930 | 522 |
| 8108716 | PCDHB16 | NM_020957 | 88 |
| 7972888 | PCID2 | BC008975 | 94 |
| 7973530 | PCK2 | NM_004563 | 653 |
| 8134869 | PCOLCE | NM_002593 | 1282 |
| 8091243 | PCOLCE2 | NM_013363 | 2116 |
| 8008598 | PCTP | NM_001102402 | 2207 |
| 7955943 | PDE1B | NM_000924 | 1980 |
| 8095080 | PDGFRA | NM_006206 | 1401 |
| 8104022 | PDLIM3 | NM_014476 | 2180 |
| 7954926 | PDZRN4 | NM_013377 | 1108 |
| 8134339 | PEG10 | NM_015068 | 837 |
| 8011692 | PELP1 | NM_014389 | 1221 |
| 8129880 | PERP | NM_022121 | 1822 |

TABLE 2-continued

| Probe Set ID | Gene Symbol | mRNA Accession GENSCAN | SEQ ID NO: |
|---|---|---|---|
| 8057959 | PGAP1 | NM_024989 | 630 |
| 7914648 | PHC2 | NM_198040 | 936 |
| 8081590 | PHLDB2 | NM_001134439 | 1633 |
| 8074748 | PI4KAP2 | NR_003700 | 1237 |
| 7921526 | PIGM | NM_145167 | 887 |
| 8075483 | PIK3IP1 | NM_052880 | 1688 |
| 8105778 | PIK3R1 | NM_181523 | 271 |
| 7915787 | PIK3R3 | NM_003629 | 1342 |
| 7943240 | PIWIL4 | NM_152431 | 1818 |
| 8026315 | PKN1 | NM_213560 | 456 |
| 8101429 | PLAC8 | NM_016619 | 1590 |
| 8129985 | PLAGL1 | NM_006718 | 1040 |
| 8078187 | PLCL2 | NM_015184 | 1797 |
| 8092134 | PLD1 | NM_002662 | 1555 |
| 8122756 | PLEKHG1 | NM_001029884 | 690 |
| 8167449 | PLP2 | NM_002668 | 2040 |
| 8066619 | PLTP | NM_006227 | 280 |
| 8073633 | PNPLA3 | NM_025225 | 115 |
| 8008064 | PNPO | NM_018129 | 1675 |
| 8044473 | POLR1B | NM_019014 | 1723 |
| 8141076 | PON2 | NM_000305 | 659 |
| 8128565 | POPDC3 | NM_022361 | 1743 |
| 7971077 | POSTN | NM_006475 | 1696 |
| 7960878 | POU5F1P3//POU5F1P3 | AF268617 | 73 |
| 7906017 | POU5F1P4 | AF268613 | 72 |
| 7999253 | PPL | NM_002705 | 1000 |
| 8121257 | PRDM1 | NM_001198 | 1402 |
| 7908924 | PRELP | NM_002725 | 384 |
| 8146794 | PREX2 | NM_024870 | 462 |
| 7962375 | PRICKLE1 | NM_153026 | 1825 |
| 8009301 | PRKCA | NM_002737 | 457 |
| 8041763 | PRKCE | NM_005400 | 458 |
| 8111490 | PRLR | NM_000949 | 2287 |
| 7924817 | PRO2012 | BC019830 | 120 |
| 8089011 | PROS1 | M15036 | 3 |
| 8136795 | PRSS1 | NM_002769 | 2208 |
| 8136790 | PRSS2 | NM_002770 | 141 |
| 7942957 | PRSS23 | NM_007173 | 1025 |

TABLE 2-continued

| Probe Set ID | Gene Symbol | mRNA Accession GENSCAN | SEQ ID NO: |
|---|---|---|---|
| 8120932 | PRSS35 | NM_153362 | 2023 |
| 8001007 | PRSS8 | NM_002773 | 1070 |
| 8149551 | PSD3 | NM_015310 | 989 |
| 8160238 | PSIP1 | NM_033222 | 1510 |
| 7932420 | PTPLA | NM_014241 | 743 |
| 8096176 | PTPN13 | NM_080683 | 1586 |
| 8160040 | PTPRD | NM_002839 | 2035 |
| 7900792 | PTPRF | NM_002840 | 880 |
| 7899562 | PTPRU | NM_133178 | 2181 |
| 7943882 | PTS | NM_000317 | 1322 |
| 8081548 | PVRL3 | NM_015480 | 68 |
| 7979085 | PYGL | NM_002863 | 1948 |
| 7949124 | PYGM | NM_005609 | 1323 |
| 7994609 | QPRT | NM_014298 | 416 |
| 8150225 | RAB11FIP1 | NM_001002814 | 2051 |
| 7950899 | RAB38 | NM_022337 | 2196 |
| 8035398 | RAB3A | NM_002866 | 1699 |
| 8044919 | RALB | NM_002881 | 474 |
| 8020100 | RALBP1 | NM_006788 | 441 |
| 8175169 | RAP2C | NM_021183 | 268 |
| 8143772 | RARRES2 | NM_002889 | 1776 |
| 7972946 | RASA3 | NM_007368 | 337 |
| 8101304 | RASGEF1B | NM_152545 | 180 |
| 8095043 | RASL11B | NM_023940 | 292 |
| 8064790 | RASSF2 | NM_014737 | 1370 |
| 7941702 | RBM14 | NM_006328 | 1616 |
| 8099967 | RBM47 | NM_001098634 | 1158 |
| 7964757 | RBMS1 | BC051889 | 248 |
| 7939120 | RCN1 | NM_002901 | 1819 |
| 7973629 | REC8 | NM_001048205 | 948 |
| 8053551 | REEP1 | NM_022912 | 1378 |
| 8024323 | REEP6 | NM_138393 | 132 |
| 7927120 | RET | NM_020975 | 1067 |
| 8151609 | REXO1L1 | NM_172239 | 2026 |
| 8058063 | RFTN2 | NM_144629 | 1454 |
| 8121649 | RFX6 | NM_173560 | 2188 |
| 7908125 | RGL1 | NM_015149 | 820 |
| 8125687 | RGL2 | NM_004761 | 1963 |
| 7908397 | RGS13 | NM_002927 | 2241 |

TABLE 2-continued

| Probe Set ID | Gene Symbol | mRNA Accession GENSCAN | SEQ ID NO: |
|---|---|---|---|
| 7918593 | RHOC | NM_175744 | 908 |
| 8110437 | RMND5B | NM_022762 | 296 |
| 7977615 | RNASE1 | NM_198232 | 2254 |
| 7962884 | RND1 | NM_014470 | 2094 |
| 8053576 | RNF103 | NM_005667 | 2212 |
| 8020806 | RNF125 | NM_017831 | 942 |
| 8116980 | RNF182 | NM_152737 | 1971 |
| 8016994 | RNF43 | NM_017763 | 1357 |
| 7903404 | RNPC3 | AK289844 | 1296 |
| 7899502 | RNU11 | NR_004407 | 1303 |
| 7919349 | RNU1A | NR_004421 | 1304 |
| 8019802 | RNU2-1 | NR_002716 | 1880 |
| 7897801 | RNU5E | NR_002754 | 1105 |
| 8162283 | ROR2 | NM_004560 | 2251 |
| 8167006 | RP2 | NM_006915 | 1384 |
| 7977507 | RPPH1 | NR_002312 | 646 |
| 8128123 | RRAGD | NM_021244 | 1740 |
| 8068902 | RRP1B | NM_015056 | 988 |
| 8095545 | RUFY3 | NM_001037442 | 1594 |
| 8088820 | RYBP | NM_012234 | 2137 |
| 7920123 | S100A10 | NM_002966 | 937 |
| 7977761 | SALL2 | NM_005407 | 476 |
| 8067087 | SALL4 | NM_020436 | 1422 |
| 8166469 | SAT1 | NM_002970 | 1920 |
| 8021183 | SCARNA17 | NR_003003 | 833 |
| 8091778 | SCARNA7 | NR_003001 | 812 |
| 7943160 | SCARNA9 | NR_002569 | 729 |
| 7955502 | SCN8A | NM_014191 | 900 |
| 7994058 | SCNN1G | NM_001039 | 1160 |
| 8076586 | SCUBE1 | NM_173050 | 1021 |
| 7957806 | SCYL2 | NM_017988 | 515 |
| 7922250 | SCYL3 | NM_181093 | 1392 |
| 8066513 | SDC4 | NM_002999 | 2256 |
| 8146550 | SDCBP | NM_005625 | 565 |
| 8110932 | SEMA5A | NM_003966 | 1127 |
| 8113666 | SEMA6A | NM_020796 | 1117 |
| 8111915 | SEPP1 | NM_005410 | 627 |
| 8102848 | SETD7 | NM_030648 | 746 |

TABLE 2-continued

| Probe Set ID | Gene Symbol | mRNA Accession GENSCAN | SEQ ID NO: |
|---|---|---|---|
| 8103254 | SFRP2 | NM_003013 | 524 |
| 8100318 | SGCB | NM_000232 | 1691 |
| 8129677 | SGK1 | NM_005627 | 1312 |
| 7979574 | SGPP1 | NM_030791 | 357 |
| 8120833 | SH3BGRL2 | NM_031469 | 1101 |
| 8085556 | SH3BP5 | NM_004844 | 876 |
| 8164521 | SH3GLB2 | NM_020145 | 193 |
| 7970676 | SHISA2 | NM_001007538 | 562 |
| 7963970 | SILV | NM_006928 | 2258 |
| 8041759 | SIX3 | NM_005413 | 1992 |
| 8107769 | SLC12A2 | NM_001046 | 347 |
| 8082012 | SLC15A2 | NM_021082 | 1888 |
| 7922162 | SLC19A2 | NM_006996 | 1388 |
| 8104930 | SLC1A3 | NM_004172 | 1374 |
| 8123246 | SLC22A3 | NM_021977 | 196 |
| 8107920 | SLC22A5 | NM_003060 | 1330 |
| 8016018 | SLC25A39 | NM_016016 | 1779 |
| 7960865 | SLC2A3 | NM_006931 | 1795 |
| 8051050 | SLC30A3 | NM_003459 | 525 |
| 8121031 | SLC35A1 | NM_006416 | 1581 |
| 7916808 | SLC35D1 | NM_015139 | 1918 |
| 8162586 | SLC35D2 | NM_007001 | 1837 |
| 7951485 | SLC35F2 | NM_017515 | 1852 |
| 8079931 | SLC38A3 | NM_006841 | 1253 |
| 8018082 | SLC39A11 | NM_139177 | 1900 |
| 7973135 | SLC39A2 | NM_014579 | 2069 |
| 8101992 | SLC39A8 | NM_022154 | 594 |
| 7948249 | SLC43A1 | NM_003627 | 2209 |
| 8025672 | SLC44A2 | NM_020428 | 1835 |
| 8064613 | SLC4A11 | NM_032034 | 2065 |
| 8095585 | SLC4A4 | NM_001098484 | 1641 |
| 7970810 | SLC7A1 | NM_003045 | 1689 |
| 8173414 | SLC7A3 | NM_032803 | 2122 |
| 8003298 | SLC7A5 | NM_003486 | 699 |
| 8000167 | SLC7A5P1 | NR_002593 | 738 |
| 8009685 | SLC9A3R1 | NM_004252 | 1780 |
| 8014233 | SLFN11 | NM_001104587 | 1272 |
| 8014248 | SLFN13 | NM_144682 | 1781 |
| 8094301 | SLIT2 | NM_004787 | 31 |

TABLE 2-continued

| Probe Set ID | Gene Symbol | mRNA Accession GENSCAN | SEQ ID NO: |
|---|---|---|---|
| 7972231 | SLITRK1 | NM_052910 | 356 |
| 7951479 | SLN | NM_003063 | 1039 |
| 7984353 | SMAD6 | NM_005585 | 1904 |
| 8154059 | SMARCA2 | NM_003070 | 467 |
| 7938100 | SMPD1 | NM_000543 | 2153 |
| 7899407 | SMPDL3B | NM_014474 | 582 |
| 7909689 | SMYD2 | NM_020197 | 1448 |
| 8150698 | SNAI2 | NM_003068 | 2283 |
| 7951032 | SNORA1 | NR_003026 | 832 |
| 7925182 | SNORA14B | NR_002956 | 808 |
| 8122144 | SNORA33 | NR_002436 | 692 |
| 8084708 | SNORA4 | NR_002588 | 737 |
| 7899480 | SNORA73A | NR_002907 | 1665 |
| 8108420 | SNORA74A | NR_002915 | 780 |
| 7951034 | SNORA8 | NR_002920 | 781 |
| 7982038 | SNORD115-1 | NR_001291 | 1052 |
| 8124940 | SNORD117 | NR_003140 | 917 |
| 8145793 | SNORD13 | NR_003041 | 845 |
| 8010078 | SNORD1C | NR_004397 | 1302 |
| 7948910 | SNORD25 | NR_002565 | 718 |
| 7948908 | SNORD26 | NR_002564 | 720 |
| 7948906 | SNORD27 | NR_002563 | 717 |
| 7948904 | SNORD28 | NR_002562 | 719 |
| 7948902 | SNORD29 | NR_002559 | 716 |
| 7948900 | SNORD30 | NR_002561 | 715 |
| 8030362 | SNORD33 | NR_000020 | 176 |
| 8013329 | SNORD3A | NR_006880 | 1338 |
| 8034512 | SNORD41 | NR_002751 | 773 |
| 7922410 | SNORD44 | NR_002750 | 1784 |
| 7922402 | SNORD47 | NR_002746 | 772 |
| 8118322 | SNORD52 | NR_002742 | 1944 |
| 8041168 | SNORD53 | NR_002741 | 771 |
| 8150877 | SNORD54 | NR_002437 | 693 |
| 8023259 | SNORD58A | NR_002571 | 734 |
| 7951030 | SNORD6 | NR_003036 | 840 |
| 7998722 | SNORD60 | NR_002736 | 770 |
| 8158864 | SNORD62A | NR_002914 | 779 |
| 7997940 | SNORD68 | NR_002450 | 703 |

TABLE 2-continued

| Probe Set ID | Gene Symbol | mRNA Accession GENSCAN | SEQ ID NO: |
|---|---|---|---|
| 7922418 | SNORD74 | NR_002579 | 740 |
| 7922416 | SNORD75 | NR_003941 | 1287 |
| 7922408 | SNORD78 | NR_003944 | 1288 |
| 7922406 | SNORD79 | NR_003939 | 1285 |
| 7922404 | SNORD80 | NR_003940 | 1286 |
| 8116532 | SNORD95 | NR_002591 | 736 |
| 8160033 | SNRPE//SNRPE//SNRPE | ENST00000338402 | 2409 |
| 7981919 | SNRPN | NM_022807 | 240 |
| 7982098 | SNRPN//SNORD109A | NR_001295 | 246 |
| 7982094 | SNRPN//SNORD115-44 | NR_003359 | 1053 |
| 7981976 | SNRPN//SNORD116-14 | NR_003329 | 1086 |
| 7981951 | SNRPN//SNORD116-2 | NR_003317 | 1048 |
| 7981990 | SNRPN//SNORD116-21 | NR_003335 | 1084 |
| 7981992 | SNRPN//SNORD116-22 | NR_003336 | 1085 |
| 7981994 | SNRPN//SNORD116-23 | NR_003337 | 1087 |
| 7982002 | SNRPN//SNORD116-27 | NR_003341 | 1080 |
| 7982004 | SNRPN//SNORD116-28 | NR_003361 | 1061 |
| 7982006 | SNRPN//SNORD116-29 | NR_003360 | 1059 |
| 7981955 | SNRPN//SNORD116-4 | NR_003319 | 1046 |
| 7981962 | SNRPN//SNORD116-5 | NR_003320 | 1051 |
| 7981964 | SNRPN//SNORD116-8 | NR_003323 | 1060 |
| 8152606 | SNTB1 | NM_021021 | 1676 |
| 8127943 | SNX14 | NM_153816 | 1228 |
| 8107613 | SNX2 | NM_003100 | 184 |
| 7907702 | SOAT1 | NM_003101 | 481 |
| 7955702 | SOAT2 | NM_003578 | 1043 |
| 7957551 | SOCS2 | NM_003877 | 153 |
| 8018864 | SOCS3 | NM_003955 | 419 |
| 8104035 | SORBS2 | NM_021069 | 1587 |
| 8051670 | SOS1 | NM_005633 | 1369 |
| 7972291 | SOX21 | NM_007084 | 435 |
| 7955217 | SPATS2 | NM_023071 | 1155 |
| 8114964 | SPINK1 | NM_003122 | 1593 |
| 8003875 | SPNS2 | NM_001124758 | 1414 |
| 7938608 | SPON1 | NM_006108 | 892 |
| 8096301 | SPP1 | NM_001040058 | 806 |
| 8114797 | SPRY4 | NM_030964 | 1464 |
| 8060997 | SPTLC3 | NM_018327 | 1009 |
| 8110569 | SQSTM1 | NM_003900 | 1451 |

TABLE 2-continued

| Probe Set ID | Gene Symbol | mRNA Accession GENSCAN | SEQ ID NO: |
|---|---|---|---|
| 8003722 | SRR | NM_021947 | 67 |
| 8064375 | SRXN1 | NM_080725 | 168 |
| 7945204 | ST14 | NM_021978 | 744 |
| 7990815 | ST20 | NM_001100880 | 2238 |
| 8081219 | ST3GAL6 | NM_006100 | 257 |
| 8135638 | ST7 | NM_018412 | 537 |
| 8113358 | ST8SIA4 | NM_005668 | 1610 |
| 8032789 | STAP2 | NM_017720 | 620 |
| 7970924 | STARD13 | NM_178006 | 1685 |
| 7964119 | STAT2 | NM_005419 | 2063 |
| 8015607 | STAT3 | NM_139276 | 454 |
| 8147030 | STMN2 | NM_007029 | 2221 |
| 7990309 | STRA6 | NM_022369 | 1762 |
| 8078360 | STT3B | NM_178862 | 249 |
| 8156861 | STX17 | NM_017919 | 1270 |
| 8100808 | SULT1E1 | NM_005420 | 241 |
| 8163383 | SUSD1 | NM_022486 | 464 |
| 7919645 | SV2A | NM_014849 | 1757 |
| 7932796 | SVIL | NM_021738 | 1180 |
| 8097080 | SYNPO2 | NM_133477 | 1531 |
| 7947590 | SYT13 | NM_020826 | 1443 |
| 8022986 | SYT4 | NM_020783 | 1734 |
| 7918716 | SYT6 | NM_205848 | 901 |
| 8166747 | SYTL5 | NM_138780 | 1938 |
| 8145954 | TACC1 | NM_006283 | 1389 |
| 8009075 | TANC2 | NM_025185 | 1292 |
| 8180061 | TAP1 | NM_000593 | 533 |
| 8136641 | TAS2R3 | NM_016943 | 668 |
| 8136645 | TAS2R4 | NM_016944 | 49 |
| 8136647 | TAS2R5 | NM_018980 | 669 |
| 8094574 | TBC1D1 | NM_015173 | 499 |
| 8019031 | TBC1D16 | NM_019020 | 285 |
| 8112767 | TBCA | NM_004607 | 838 |
| 8139468 | TBRG4 | NM_004749 | 355 |
| 8138997 | TBX20 | NM_001077653 | 1990 |
| 7966668 | TBX5 | NM_181486 | 263 |
| 8072360 | TCN2 | NM_000355 | 2111 |
| 8097991 | TDO2 | NM_005651 | 1549 |

TABLE 2-continued

| Probe Set ID | Gene Symbol | mRNA Accession GENSCAN | SEQ ID NO: |
|---|---|---|---|
| 7938544 | TEAD1 | NM_021961 | 2120 |
| 8125887 | TEAD3 | NM_003214 | 1132 |
| 8154692 | TEK | NM_000459 | 1409 |
| 8096669 | TET2 | NM_017628 | 2296 |
| 8150138 | TEX15 | NM_031271 | 1077 |
| 8082797 | TF | NM_001063 | 1957 |
| 8120194 | TFAP2B | NM_003221 | 1003 |
| 8078350 | TGFBR2 | NM_001024847 | 1078 |
| 7982597 | THBS1 | NM_003246 | 364 |
| 8085797 | THRB | NM_001128176 | 1504 |
| 8077513 | THUMPD3 | NM_015453 | 1334 |
| 7952268 | THY1 | NM_006288 | 1793 |
| 8072626 | TIMP3 | NM_000362 | 727 |
| 8085360 | TIMP4 | NM_003256 | 2263 |
| 8018849 | TK1 | NM_003258 | 1326 |
| 8091402 | TM4SF18 | NM_138786 | 2110 |
| 7993638 | TMC5 | NM_001105248 | 1279 |
| 7993588 | TMC7 | NM_024847 | 1909 |
| 7921987 | TMCO1 | NM_019026 | 1440 |
| 7954985 | TMEM117 | NM_032256 | 87 |
| 7959807 | TMEM132B | NM_052907 | 792 |
| 7959827 | TMEM132C | NM_001136103 | 2025 |
| 7942964 | TMEM135 | NM_022918 | 2020 |
| 8098041 | TMEM144 | NM_018342 | 1595 |
| 8142407 | TMEM168 | NM_022484 | 857 |
| 8137264 | TMEM176A | NM_018487 | 272 |
| 8044844 | TMEM177 | NM_001105198 | 1275 |
| 8057732 | TMEM194B | AK302425 | 1570 |
| 8127637 | TMEM30A | NM_018247 | 1805 |
| 7951987 | TMPRSS13 | NM_001077263 | 2323 |
| 8070467 | TMPRSS2 | NM_005656 | 1655 |
| 8174189 | TMSB15A | NM_021992 | 701 |
| 7957417 | TMTC2 | NM_152588 | 182 |
| 8087925 | TNNC1 | NM_003280 | 1645 |
| 8139500 | TNS3 | NM_022748 | 2232 |
| 8013159 | TOM1L2 | NM_001082968 | 1074 |
| 8066461 | TOMM34 | NM_006809 | 374 |
| 8150962 | TOX | NM_014729 | 510 |
| 7984079 | TPM1 | NM_000366 | 642 |

TABLE 2-continued

| Probe Set ID | Gene Symbol | mRNA Accession GENSCAN | SEQ ID NO: |
|---|---|---|---|
| 8053036 | TPRKB | NM_016058 | 1651 |
| 7909545 | TRAF5 | NM_145759 | 730 |
| 8148304 | TRIB1 | NM_025195 | 369 |
| 8097841 | TRIM2 | NM_015271 | 1553 |
| 7946089 | TRIM5 | NM_033034 | 2029 |
| 8146669 | TRIM55 | NM_033058 | 315 |
| 8104107 | TRIML2 | NM_173553 | 217 |
| 7971104 | TRPC4 | NM_016179 | 1697 |
| 7951178 | TRPC6 | NM_004621 | 1383 |
| 8161654 | TRPM3 | NM_206946 | 1211 |
| 8005171 | TRPV2 | NM_016113 | 2176 |
| 8136801 | TRY6 | NR_001296 | 1932 |
| 8021768 | TSHZ1 | NM_005786 | 799 |
| 7928705 | TSPAN14 | NM_030927 | 1513 |
| 7928046 | TSPAN15 | NM_012339 | 547 |
| 7939559 | TSPAN18 | NM_130783 | 2031 |
| 8173941 | TSPAN6 | NM_003270 | 142 |
| 8167763 | TSPYL2 | NM_022117 | 1976 |
| 7917199 | TTLL7 | NM_024686 | 841 |
| 8123644 | TUBB2A | NM_001069 | 674 |
| 7905428 | TUFT1 | NM_020127 | 1425 |
| 7982938 | TYRO3 | NM_006293 | 2090 |
| 8159554 | UAP1L1 | NM_207309 | 1444 |
| 8018708 | UBE2O | NM_022066 | 1524 |
| 7906662 | UFC1 | NM_016406 | 1239 |
| 8100760 | UGT2A3 | NM_024743 | 1532 |
| 8095390 | UGT2B10 | NM_001075 | 1804 |
| 8095404 | UGT2B28 | NM_053039 | 113 |
| 8100784 | UGT2B4 | NM_021139 | 1170 |
| 8095395 | UGT2B7 | NM_001074 | 1512 |
| 8111524 | UGT3A2 | NM_174914 | 2013 |
| 8097017 | UGT8 | NM_001128174 | 1502 |
| 8165703 | UIMC1 | AF284753 | 75 |
| 8123388 | UNC93A | NM_018974 | 1803 |
| 8168416 | USMG5 | BC072683 | 477 |
| 8067903 | USP25 | NM_013396 | 489 |
| 8167601 | USP27X | AY672104 | 566 |
| 8017212 | USP32 | NM_032582 | 410 |

TABLE 2-continued

| Probe Set ID | Gene Symbol | mRNA Accession GENSCAN | SEQ ID NO: |
|---|---|---|---|
| 8059801 | USP40 | NM_018218 | 958 |
| 8097098 | USP53 | NM_019050 | 1140 |
| 8122464 | UTRN | NM_007124 | 898 |
| 7909642 | VASH2 | NM_024749 | 1710 |
| 7928444 | VCL | NM_014000 | 498 |
| 8088979 | VGLL3 | NM_016206 | 569 |
| 8048319 | VIL1 | NM_007127 | 1577 |
| 7926368 | VIM | NM_003380 | 1925 |
| 8053562 | VPS24 | NM_016079 | 2171 |
| 8052626 | VPS54 | NM_016516 | 544 |
| 8040430 | VSNL1 | NM_003385 | 645 |
| 8013606 | VTN | NM_000638 | 789 |
| 8169022 | WBP5 | NM_016303 | 558 |
| 8133258 | WBSCR17 | NM_022479 | 175 |
| 7965343 | WDR51B | NM_172240 | 2240 |
| 8143941 | WDR86 | NM_198285 | 1259 |
| 7938364 | WEE1 | BX641032 | 301 |
| 8056860 | WIPF1 | NM_003387 | 971 |
| 8142471 | WNT2 | NM_003391 | 1591 |
| 8005765 | WSB1 | NM_015626 | 587 |
| 8165947 | WWC3 | NM_015691 | 1248 |
| 8083092 | ZBTB38 | NM_001080412 | 1130 |
| 7908978 | ZC3H11A | NM_014827 | 935 |
| 8047784 | ZDBF2 | NM_020923 | 1185 |
| 8160151 | ZDHHC21 | NM_178566 | 2096 |
| 8147000 | ZFHX4 | NM_024721 | 2061 |
| 8028652 | ZFP36 | NM_003407 | 1100 |
| 8083233 | ZIC1 | NM_003412 | 684 |
| 7928558 | ZMIZ1 | NM_020338 | 1750 |
| 8139832 | ZNF117 | NM_015852 | 1089 |
| 7925691 | ZNF124 | NM_003431 | 404 |
| 7899870 | ZNF362 | NM_152493 | 348 |
| 7975645 | ZNF410 | NM_021188 | 63 |
| 7913582 | ZNF436 | NM_001077195 | 960 |
| 8038998 | ZNF468 | NM_199132 | 581 |

TABLE 2-continued

| Probe Set ID | Gene Symbol | mRNA Accession GENSCAN | SEQ ID NO: |
|---|---|---|---|
| 7934553 | ZNF503 | NM_032772 | 1724 |
| 8039687 | ZNF552 | NM_024762 | 862 |
| 8031837 | ZNF587 | AF294842 | 93 |
| 8079598 | ZNF589 | NM_016089 | 1137 |
| 8019541 | ZNF750 | NM_024702 | 923 |
| 8038967 | ZNF83 | NM_001105549 | 1290 |
| 8105506 | ZSWIM6 | NM_020928 | 1709 |

To determine specific developmental effects, sets of tissue specific genes were generated by cross comparison of microarrays from eight adult somatic tissues [20] (see Materials and Methods). The changed genes were then classified into the tissue specific gene sets from the five most relevant tissues. The fold enrichment of tissue specific genes was analyzed separately for the up- and down-regulated genes. Significance was calculated using Chi-Square independence tests and corrected for multiple testing (FIG. 1B).

Treatment with RA had a dramatic effect on tissue specific gene expression. Brain specific genes were found to be enriched in genes both upregulated and downregulated by RA (2.6 and 13.2 fold, $p=0.03$ and $p<1*10^{-15}$, respectively). Also downregulated were heart specific genes (5.3, $p=1*10^{-5}$). These results correspond to the major known malformations in infants induced by RA in the central nervous system and heart [13]. In EBs treated with high doses of ethanol there was significant enrichment in upregulated liver (6.5, $p<1*10^{-15}$) and heart (3.5, $p=1*10^{-4}$) specific genes, congruent with the known teratogenic phenotype, there was also downregulation of brain specific genes (6.4, $p=1*10^{-5}$). Thalidomide caused upregulation of brain and liver-specific genes (12.5 and 17 fold, $p<1*10^{-15}$ and $p<1*10^{-15}$, respectively) as well as downregulation of liver specific genes (4.4 fold, $p=0.015$).

Example 2

Functional Analysis of Retinoic Acid, Thalidomide, and Ethanol Affected Genes

To further characterize the molecular events induced by ethanol, RA and thalidomide, Gene Ontology based functional annotation was performed [22] (FIG. 2). Of the categories enriched in genes upregulated by RA are the homeobox protein genes (14.1 fold above expected frequency). Hox genes of the Homeobox gene family are key regulators of many developmental processes and are known to be directly regulated by RA signaling [23]. Hox genes have been shown to be expressed in vertebrates along the dorsal axis in a spatially and temporally regulated manner, such that the 3' located genes are expressed earlier and in the anterior regions, while the 5' located genes are expressed later on and in the posterior parts of the embryo. In the present analysis it has been shown that the anterior HoxA and HoxB genes are specifically upregulated by RA treatment both in HESC and HiPSC EBs (FIG. 3A). In the ethanol treated EBs the most significantly upregulated functional group were liver protein genes (9.3 fold) (FIG. 2). These include several apolipoprotein and fibrinogen genes (FIG. 3B) as well as the early hepatic markers alpha-fetoprotein (AFP) and transthyretin. Later adult hepatic markers such as albumin and the alcohol dehydrogenase genes were not upregulated. Thalidomide caused significant upregulation of genes responsible for metabolism of xenobiotics (11.5 fold) and downregulation of oxidative stress response genes (15.8 fold). This observation fits with previous reports connecting thalidomide activity with reactive oxygen species induced DNA damage. Additionally affected were several developmental related gene groups such as nervous system development genes (2.5 fold) and transforming growth factor beta genes (29.6 fold) (FIG. 2).

Example 3

Retinoic Acid and Ethanol Alter Differentiation of Treated EBs as Predicted by Gene Expression Profiling In order to validate the microarray results and characterize the observed effects at the cellular level, immunofluorescent labeling was performed on the treated EBs. Using this method two major cellular effects previously highlighted by mRNA expression analysis were examined. Specifically, the protein levels of the fetal liver specific gene AFP and the earlier endodermal marker SOX17 were examined to assess the effects of ethanol treatment. The effect of RA treatment on neural differentiation was determined using antibodies for the HOXA1 protein and the neuronal specific protein NCAM1.

Ethanol treatment clearly caused elevation of AFP staining, as was expected from the dramatic increase in mRNA levels shown by the microarray analysis. Interestingly, there was also dramatic increase in SOX17 staining (FIGS. 4A-D). This would suggest that ethanol acts to increase differentiation of HESCs into the endodermal lineage, a subpopulation of which continues to differentiate into AFP-expressing early hepatic-like cells. The most dramatic effect of RA treatment was in the significant overexpression of the Hox genes (FIG. 3), and the misexpression of brain specific genes (FIG. 2), such that there was both significant up- and down-regulation of these genes. HOXA1 in particular was highly overexpressed at the mRNA level (13.6 fold, P-value=0.0003). Indeed, at the protein level a similar increase in HOXA1 abundance can be seen, together with NCAM1 (FIGS. 4E-H), indicating significant effects of RA on neuronal differentiation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

References

Other References are Cited in the Application

1. OECD. OECD Guidelines for the testing of chemicals. No. 414: Prenatal developmental toxicity study (Organization for Economic Co-operation and Development). 2001.
2. Newman L M, Johnson E M, Staples R E. Assessment of the effectiveness of animal developmental toxicity testing for human safety. *Reprod Toxicol.* 1993; 7, 359-90.
3. Collins T F, Welsh J J, Black T N, et al. A study of the teratogenic potential of caffeine ingested in drinking-water. *Food Chem Toxicol.* 1983; 21, 763-77.
4. Kimmel C A, Wilson J G, Schumacher H J. Studies on metabolism and identification of the causative agent in aspirin teratogenesis in rats. *Teratology.* 1971; 4, 15-24.
5. Schuldiner M, Yanuka O, Itskovitz-Eldor J, et al. Effects of eight growth factors on the differentiation of cells derived from human embryonic stem cells. *Proc Natl Acad Sci USA.* 2000; 97, 11307-12.
6. Dvash T, Mayshar Y, Dan H, et al. Temporal gene expression during differentiation of human embryonic stem cells and embryoid bodies. *Hum Reprod.* 2004; 19, 2875-83.
7. Genschow E, Spielmann H, Scholz G, et al. Validation of the embryonic stem cell test in the international ECVAM validation study on three in vitro embryotoxicity tests. *Altern Lab Anim.* 2004; 32, 209-44.
8. Schmidt M M, Guan K, Wobus A M. Lithium influences differentiation and tissue-specific gene expression of mouse embryonic stem (ES) cells in vitro. *Int J Dev Biol.* 2001; 45, 421-9.
9. Rohwedel J, Guan K, Wobus A M. Induction of cellular differentiation by retinoic acid in vitro. *Cells Tissues Organs.* 1999; 165, 190-202.
10. Adler S, Lindqvist J, Uddenberg K, et al. Testing potential developmental toxicants with a cytotoxicity assay based on human embryonic stem cells. *Altern Lab Anim.* 2008; 36, 129-40.
11. Mehta A, Konala V B, Khanna A, et al. Assessment of drug induced developmental toxicity using human embryonic stem cells. *Cell Biol Int.* 2008; 32, 1412-24.
12. Flora S J, Mehta A. Monoisoamyl dimercaptosuccinic acid abrogates arsenic-induced developmental toxicity in human embryonic stem cell-derived embryoid bodies: comparison with in vivo studies. *Biochem Pharmacol.* 2009; 78, 1340-9.
13. Lammer E J, Chen D T, Hoar R M, et al. Retinoic acid embryopathy. *N Engl J. Med.* 1985; 313, 837-41.
14. Szabo K T. Teratogenic effect of lithium carbonate in the foetal mouse. *Nature.* 1970; 225, 73-5.
15. Cohen L S, Friedman J M, Jefferson J W, et al. A reevaluation of risk of in utero exposure to lithium. *Jama.* 1994; 271, 146-50.
16. Parman T, Wiley M J, Wells P G. Free radical-mediated oxidative DNA damage in the mechanism of thalidomide teratogenicity. *Nat Med.* 1999; 5, 582-5.
17. Nehlig A, Debry G. Potential teratogenic and neurodevelopmental consequences of coffee and caffeine exposure: a review on human and animal data. *Neurotoxicol Teratol.* 1994; 16, 531-43.
18. Thomson J A, Itskovitz-Eldor J, Shapiro S S, et al. Embryonic stem cell lines derived from human blastocysts. *Science.* 1998; 282, 1145-7.
19. Pick M, Stelzer Y, Bar-Nur O, et al. Clone- and gene-specific aberrations of parental imprinting in human induced pluripotent stem cells. *Stem Cells.* 2009; 27, 2686-90.
20. Pradervand S, Paillusson A, Thomas J, et al. Affymetrix Whole-Transcript Human Gene 1.0 ST array is highly concordant with standard 3' expression arrays. *Biotechniques.* 2008; 44, 759-62.
21. Almond-Roesler B, Blume-Peytavi U, Bisson S, et al. Monitoring of isotretinoin therapy by measuring the plasma levels of isotretinoin and 4-oxo-isotretinoin. A useful tool for management of severe acne. *Dermatology.* 1998; 196, 176-81.
22. Huang D W, Sherman B T, Lempicki R A. Systematic and integrative analysis of large gene lists using DAVID bioinformatics resources. *Nat Protoc.* 2009; 4, 44-57.
23. Marshall H, Studer M, Popperl H, et al. A conserved retinoic acid response element required for early expression of the homeobox gene Hoxb-1. *Nature.* 1994; 370, 567-71.
24. Yelin R, Schyr R B, Kot H, et al. Ethanol exposure affects gene expression in the embryonic organizer and reduces retinoic acid levels. *Dev Biol.* 2005; 279, 193-204.
25. Jacobson S J, Jones K, Johnson K, et al. Prospective multicentre study of pregnancy outcome after lithium exposure during first trimester. *Lancet.* 1992; 339, 530-3.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08945847B2). An electronic copy of the "Sequence Listing" will also be available from the USPTO upon request and payment of the fee set forth in 37 CFR 1.19(b)(3).

What is claimed is:

1. A method of ascertaining the bio-safety of an agent, the method comprising:
    (a) generating embryoid bodies from human pluripotent stem cells:
    (b) contacting the agent with said embryoid bodies concomitant with said generating or following said generating;
    (c) analyzing a level of gene expression of more than 4000 random, non-biased genes in said embryoid bodies; and
    (d) when said agent is qualified as being safe, testing said agent on an animal model to ascertain biosafety,
    wherein said agent is qualified as being safe if at least one of the following qualification parameters are fulfilled:
    (i) less than 1% of said random, unbiased genes are differentially expressed;
    (ii) no more than 4% of said random, unbiased genes that are differentially expressed are involved in fetal development; or
    (iii) less than 5% of the tissue specific genes of a tissue of said random, unbiased genes are differentially expressed.

2. The method of claim 1, wherein said human pluripotent stem cells comprise human embryonic stem cells.

3. The method of claim 1, wherein said agent is qualified as being safe when said qualification parameter (i) is fulfilled.

4. The method of claim 1, wherein said tissue is selected from the group consisting of heart, blood, liver, skeletal muscle and brain.

5. The method of claim 1, wherein said agent is qualified as being safe when both said qualification parameter (i) and said qualification parameter (ii) is fulfilled.

6. The method of claim 1, wherein said agent is qualified as being safe when both said qualification parameter (i) and said qualification parameter (iii) is fulfilled.

7. The method of claim 1, wherein said agent is qualified as being safe when both said qualification parameter (ii) and said qualification parameter (iii) is fulfilled.

8. The method of claim 1, wherein said agent is qualified as being safe when each of said qualification parameter (i), said qualification parameter (ii) and said qualification parameter (iii) is fulfilled.

9. The method of claim 1, wherein said analyzing gene expression is effected by quantifying a level of a protein product of the genes in said embryoid bodies.

10. The method of claim 9, wherein quantifying a level of said protein is effected by using an antibody.

11. The method of claim 1, wherein said analyzing gene expression is effected by detecting the presence in said embryoid bodies of transcribed polynucleotides of said genes or portions thereof.

12. The method of claim 11, wherein said transcribed polynucleotides are mRNA.

13. The method of claim 11, wherein said transcribed polynucleotides or portions thereof are detected via labeled probes which specifically hybridize with said transcribed polynucleotides or portions thereof.

14. The method of claim 13, wherein said labeled probes are conjugated to a solid support.

15. The method of claim 14, wherein the solid support is selected from the group consisting of a nylon membrane, glass slide, glass beads and a silicon chip.

16. The method of claim 1, further comprising documenting results of said testing.

17. The method of claim 1, wherein said agent is selected from the group consisting of a pharmaceutical agent, a food additive, an industrial chemical, a cosmetic agent and a pesticide.

18. A method of ascertaining the bio-safety of an agent, the method comprising:
    (a) contacting the agent with differentiating human pluripotent stem cells;
    (b) extracting RNA from said differentiating human pluripotent stem cells; and
    (c) analyzing a level of expression of genes using said RNA and an array which detects expression levels of between 20-1000 genes, wherein at least 30% of said 20-1000 genes are tissue specific genes, wherein a difference in expression below a predetermined number of said 20-1000 genes as compared to control differentiating human pluripotent stem cells that have not been contacted with said agent is indicative of an agent being safe.

19. The method of claim 18, wherein at least an additional 30% of said 20-1000 genes are genes involved in fetal development.

* * * * *